United States Patent
Kandimalla et al.

(10) Patent No.: US 7,709,617 B2
(45) Date of Patent: May 4, 2010

(54) SYNERGISTIC STIMULATION OF THE IMMUNE SYSTEM USING IMMUNOSTIMULATORY OLIGONUCLEOTIDES AND/OR IMMUNOMER COMPOUNDS IN CONJUNCTION WITH CYTOKINES AND/OR CHEMOTHERAPEUTIC AGENTS OR RADIATION THERAPY

(75) Inventors: Ekambar R. Kandimalla, Southboro, MA (US); Sudhir Agrawal, Shrewsbury, MA (US)

(73) Assignee: Idera Pharmaceuticals, Inc., Cambridge, MA (US)

( * ) Notice: Subject to any disclaimer, the term of this patent is extended or adjusted under 35 U.S.C. 154(b) by 28 days.

(21) Appl. No.: 11/173,983

(22) Filed: Jul. 1, 2005

(65) Prior Publication Data
US 2006/0217328 A1 Sep. 28, 2006

Related U.S. Application Data

(63) Continuation of application No. 10/892,550, filed on Jul. 15, 2004.

(60) Provisional application No. 60/487,529, filed on Jul. 15, 2003.

(51) Int. Cl.
C07H 21/04 (2006.01)
C07H 21/00 (2006.01)
A61K 31/7088 (2006.01)
A61K 31/7115 (2006.01)

(52) U.S. Cl. .................. 536/23.1; 536/22.1; 536/24.5; 536/25.6; 514/44 R

(58) Field of Classification Search ................ None
See application file for complete search history.

(56) References Cited

U.S. PATENT DOCUMENTS

| | | | |
|---|---|---|---|
| 5,366,878 | A | 11/1994 | Pederson et al. |
| 5,635,377 | A | 6/1997 | Pederson et al. |
| 5,652,355 | A | 7/1997 | Metelev et al. |
| 5,912,332 | A | 6/1999 | Agrawal et al. |
| 6,218,371 | B1 | 4/2001 | Krieg et al. |
| 6,346,614 | B1 | 2/2002 | Metelev et al. |
| 6,426,334 | B1 | 7/2002 | Agrawal et al. |
| 6,429,199 | B1 | 8/2002 | Krieg et al. |
| 6,476,000 | B1 | 11/2002 | Agrawal |

FOREIGN PATENT DOCUMENTS

| | | |
|---|---|---|
| WO | WO 98/49288 | 11/1998 |
| WO | WO 01/12804 | 2/2001 |
| WO | PCT/US01/13682 | 8/2001 |
| WO | WO 01/55370 | 8/2001 |
| WO | PCT/US0130137 | 4/2002 |

OTHER PUBLICATIONS

Hartmann et al., 2003, Eu. J. Immunol.33: 1633-1641.*
Kandimalla et al., 2003, Nucleic Acids Res. 31:2393-2400.*
Kuramoto et al., Jpn. J. Cancer Res. 83:1128-1131 (1992).
Krieg et al., Nature 371:546-549 (1995).
Liang et al., J. Clin. Invest., 98(5):1119-1129 (1996).
Moldoveanu et al., Vaccine, 16(11/12):1216-1224 (1998).
McCluskie et al., J. Immunol., 161:4463-4466 (1998).
Zhao et al., Biochem. Pharmacol., 51:173-182 (1996).
Zhao et al., Biochem. Pharmacol., 52:1537-1544 (1996).
Zhao et al., Antisense Nuc. Acid Drug Dev., 7:495-502 (1997).
Zhao et al., Bioorg. Med. Chem. Lett., 9:3453-3458 (1999).
Zhao et al., Bioorg. Med. Chem. Lett., 10:1051-1054 (2000).
Yu et al., Bioorg. Med. Chem. Lett., 10:2585-2588 (2000).
Yu et al., Bioorg. Med. Chem. Lett., 11:2263-2267 (2001).
Kandimalla et al., Bioorg. Med. Chem., 9:807-813 (2001).
Decker et al., Experimental Hematology, 28:558-565 (2000).
Remington's Pharmaceutical Sciences, 18th Edition, ed. A. Gennaro, Mack Publishing 1990.
Remington: The Science and Practice of Pharmacy, 20th Edition, ed. A.L. Gennaro, Lippincott Williams & Wilkins Pub. Co., (ISBN: 0683306472).
Noronha et al., Biochem. 39(4):7050-7062 (2000).

* cited by examiner

*Primary Examiner*—Michael Burkhart
(74) *Attorney, Agent, or Firm*—Preti Flaherty; Wayne A. Keown

(57) ABSTRACT

The invention provides optimized methods and compositions for enhancing the immune response caused by immunostimulatory compounds used for the treatment of disease such as, but not limited to, treatment of cancer, autoimmune disorders, asthma, respiratory allergies, food allergies and infectious diseases in a patient. The optimized methods according to the invention provide synergy between the therapeutic effects of immunostimulatory oligonucleotides and immunomer compounds in accordance with the invention, and the therapeutic effect of cytokine immunotherapy and/or chemotherapeutic agents and/or radiation.

7 Claims, 19 Drawing Sheets

Linkers for linear synthesis

Linear Synthesis of Immunomers

Parallel Synthesis of Immunomers

IL-12 Production with oligos in BALB/c splenocyte assay (24 hs)

```
                            SEQUENCE LISTING

<160> NUMBER OF SEQ ID NOS: 165

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gagaacgctc gacctt                                                       16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gagaacgctc gacctt                                                       16

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagaacgctc gacctt                                                       16

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctatctgacg ttctctgt                                                     18

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tgacgttctc tgt                                                          13

<210> SEQ ID NO 6
<211> LENGTH: 13
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 6
tgacgttctc tgt                                                          13

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctatctgacg ttctctgt                                                     18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctatctgacg ttctctgt                                                     18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 50HdC

<400> SEQUENCE: 9
ctatctgang ttctctgt                                                     18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 7-deaza-dG

<400> SEQUENCE: 10
ctatctgacn ttctctgt                                                     18

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (5)
<223> OTHER INFORMATION: 5OHdC

<400> SEQUENCE: 11
ctgangttct ctgt                                                        14

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 12
ctgacnttct ctgt                                                        14

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctgacgttct ctgt                                                        14

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctgacgttct ctgt                                                        14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 5OHdC

<400> SEQUENCE: 15
ctgangttct ctgt                                                        14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG
```

```
<400> SEQUENCE: 16
ctgacnttct ctgt                                                           14

<210> SEQ ID NO 17
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 1',2'-dideoxyriboside

<400> SEQUENCE: 17
nntgacgttc tctgt                                                          15

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside

<400> SEQUENCE: 18
nnntgacgtt ctctgt                                                         16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (7)
<223> OTHER INFORMATION: 5OHdC

<400> SEQUENCE: 19
nnntgangtt ctctgt                                                         16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (8)
<223> OTHER INFORMATION: 7-deaza-dG

<400> SEQUENCE: 20
```

-continued nnntgacntt ctctgt                                                  16

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tctgacgttc t                                                       11

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside

<400> SEQUENCE: 22
nnntctgacg ttct                                                    14

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (9)
<223> OTHER INFORMATION: 7-deaza-dG

<400> SEQUENCE: 23
nnntctgang ttct                                                    14

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: 1',2'-dideoxyriboside
<220> FEATURE:
<221> NAME/KEY: modified_base
<222> LOCATION: (10)
<223> OTHER INFORMATION: 7-deaza-dG

<400> SEQUENCE: 24
nnntctgacn ttct                                                    14

<210> SEQ ID NO 25
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 25
ctatctgtcg ttctctgt                                                    18

<210> SEQ ID NO 26
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 26
tctgtcnttc t                                                           11

<210> SEQ ID NO 27
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG

<400> SEQUENCE: 27
tctgtcnttc t                                                           11

<210> SEQ ID NO 28
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraC
<220> FEATURE:
<221> NAME/KEY: modified_base
<222> LOCATION: (7)
<223> OTHER INFORMATION: AraG

<400> SEQUENCE: 28
tctgtnnttc t                                                           11

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: 1',2'-dideoxyriboside
<220> FEATURE:
<221> NAME/KEY: modified_base
<222> LOCATION: (9)
<223> OTHER INFORMATION: 7-deaza-dG
```

```
<400> SEQUENCE: 29
nntctgtcnt tct                                                              13

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraG
<220> FEATURE:
<221> NAME/KEY: misc_feature
<222> LOCATION: (1)..(14)
<223> OTHER INFORMATION: phosphodiester linkage

<400> SEQUENCE: 30
ctgtcnttct ctgt                                                             14

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: AraC
<220> FEATURE:
<221> NAME/KEY: modified_base
<222> LOCATION: (6)
<223> OTHER INFORMATION: AraG
<220> FEATURE:
<221> NAME/KEY: misc_feature
<222> LOCATION: (1)..(14)
<223> OTHER INFORMATION: phosphodiester linkage

<400> SEQUENCE: 31
ctgtnnttct ctgt                                                             14

<210> SEQ ID NO 32
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 32
tctgacnttc t                                                                11

<210> SEQ ID NO 33
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
```

```
<223> OTHER INFORMATION: 1',2'-dideoxyriboside
<220> FEATURE:
<221> NAME/KEY: modified_base
<222> LOCATION: (9)
<223> OTHER INFORMATION: 7-deaza-dG

<400> SEQUENCE: 33
nntctgacnt tct                                                              13

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: AraG

<400> SEQUENCE: 34
tctgacnttc t                                                                11

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraC
<220> FEATURE:
<221> NAME/KEY: modified_base
<222> LOCATION: (7)
<223> OTHER INFORMATION: AraG

<400> SEQUENCE: 35
tctgannttc t                                                                11

<210> SEQ ID NO 36
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: AraC
<220> FEATURE:
<221> NAME/KEY: misc_feature
<222> LOCATION: (1)..(14)
<223> OTHER INFORMATION: phosphodiester linkage

<400> SEQUENCE: 36
ctgangttct ctgt                                                             14

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (6)
<223> OTHER INFORMATION: AraG
<220> FEATURE:
<221> NAME/KEY: misc_feature
<222> LOCATION: (1)..(14)
<223> OTHER INFORMATION: phosphodiester linkage

<400> SEQUENCE: 37
ctgacnttct ctgt                                                    14

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: AraC
<220> FEATURE:
<221> NAME/KEY: modified_base
<222> LOCATION: (6)
<223> OTHER INFORMATION: AraG
<220> FEATURE:
<221> NAME/KEY: misc_feature
<222> LOCATION: (1)..(14)
<223> OTHER INFORMATION: phosphodiester linkage

<400> SEQUENCE: 38
ctgannttct ctgt                                                    14

<210> SEQ ID NO 39
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39 ctat                                                                4

<210> SEQ ID NO 40
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40 cta                                                                 3

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: AraG

<400> SEQUENCE: 41
ctgtcnttct c                                                       11
```

<210> SEQ ID NO 42
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 42 tcntcnttg                                                                9

<210> SEQ ID NO 43
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 7-deaza-dG
<220> FEATURE:
<221> NAME/KEY: modified_base
<222> LOCATION: (6)
<223> OTHER INFORMATION: 7-deaza-dG

<400> SEQUENCE: 43
tcntcnttct g                                                            11

<210> SEQ ID NO 44
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44 tcgttg                                                                   6

<210> SEQ ID NO 45
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 tcgtt                                                                    5

<210> SEQ ID NO 46
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)

```
<223> OTHER INFORMATION: phosphorothioate linkage

<400> SEQUENCE: 46 agagag                                                                6

<210> SEQ ID NO 47
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: phosphodiester linkage

<400> SEQUENCE: 47 agagag                                                                6

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 48
tctgtcnttc t                                                         11

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphorothioate linkage

<400> SEQUENCE: 49
cagagctctg                                                           10

<210> SEQ ID NO 50
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: 2'-O-methylribonucleotide
<220> FEATURE:
<221> NAME/KEY: misc_feature
<222> LOCATION: (1)..(10)
<223> OTHER INFORMATION: phosphorothioate linkage

<400> SEQUENCE: 50
cagagcucug                                                           10
```

```
<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ctcactttcg ttctctgt                                                     18

<210> SEQ ID NO 52
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphorothioate linkage

<400> SEQUENCE: 52 ttgtgctt                                                                 8

<210> SEQ ID NO 53
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(2)
<223> OTHER INFORMATION: phosphorothioate linkage
<220> FEATURE:
<221> NAME/KEY: misc_feature
<222> LOCATION: (3)..(12)
<223> OTHER INFORMATION: phosphodiester linkage

<400> SEQUENCE: 53
ggcatcgatg cc                                                           12

<210> SEQ ID NO 54
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(6)
<223> OTHER INFORMATION: phosphodiester linkage

<400> SEQUENCE: 54 gagctc                                                                   6

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: phosphodiester linkage
```

```
<400> SEQUENCE: 55
gacagagctc tgtc                                                           14

<210> SEQ ID NO 56
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-O-methylribonucleotide
<220> FEATURE:
<221> NAME/KEY: modified_base
<222> LOCATION: (6)
<223> OTHER INFORMATION: 2'-O-methylribonucleotide
<220> FEATURE:
<221> NAME/KEY: misc_feature
<222> LOCATION: (1)..(8)
<223> OTHER INFORMATION: phosphorothioate linkage

<400> SEQUENCE: 56 tcgtcgtt                                                                   8

<210> SEQ ID NO 57
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 57
tctttngttc t                                                              11

<210> SEQ ID NO 58
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 58
tctttcnttc t                                                              11

<210> SEQ ID NO 59
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 5OHdC

<400> SEQUENCE: 59
``` ttngttct                                                                8

<210> SEQ ID NO 60
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: 7-deaza-dG

<400> SEQUENCE: 60 ttcnttct                                                                8

<210> SEQ ID NO 61
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 61
tctgtngttc t                                                           11

<210> SEQ ID NO 62
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 62
tctgtcnttc t                                                           11

<210> SEQ ID NO 63
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 5OHdC

<400> SEQUENCE: 63 gtngttct                                                                8

<210> SEQ ID NO 64
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<221> NAME/KEY: modified_base
<222> LOCATION: (4)
<223> OTHER INFORMATION: 7-deaza-dG

<400> SEQUENCE: 64 gtcnttct                                                                8

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 5OHdC

<400> SEQUENCE: 65
ctatctgang ttctctgt                                                    18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 7-deaza-dG

<400> SEQUENCE: 66
ctatctgacn ttctctgt                                                    18

<210> SEQ ID NO 67
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 5OHdC

<400> SEQUENCE: 67
ctgangttct ctgt                                                        14

<210> SEQ ID NO 68
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 7-deaza-dG

<400> SEQUENCE: 68
ctgacnttct ctgt                                                        14

<210> SEQ ID NO 69
<211> LENGTH: 11
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC

<400> SEQUENCE: 69
tctgangttc t                                                          11

<210> SEQ ID NO 70
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG

<400> SEQUENCE: 70
tctgacnttc t                                                          11

<210> SEQ ID NO 71
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 5OHdC

<400> SEQUENCE: 71 gangttct                                                               8

<210> SEQ ID NO 72
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: 7-deaza-dG

<400> SEQUENCE: 72 gacnttct                                                               8

<210> SEQ ID NO 73
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ctgacgttct                                                            10
```

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: phosphodiester linkage

<400> SEQUENCE: 74
gctgacagag ctctgtcagc                                              20

<210> SEQ ID NO 75
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: 2'-O-methylribonucleotide
<220> FEATURE:
<221> NAME/KEY: misc_feature
<222> LOCATION: (1)..(10)
<223> OTHER INFORMATION: phosphodiester linkage

<400> SEQUENCE: 75
cagagcucug                                                         10

<210> SEQ ID NO 76
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(9)
<223> OTHER INFORMATION: phosphorothioate linkage

<400> SEQUENCE: 76 tcgtcgttg                                                           9

<210> SEQ ID NO 77
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: phosphodiester linkage

<400> SEQUENCE: 77
tgcatcgatg ca                                                      12

<210> SEQ ID NO 78
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: misc_feature
<222> LOCATION: (1)..(12)
<223> OTHER INFORMATION: phosphodiester linkage

<400> SEQUENCE: 78
acgtagctac gt                                                              12

<210> SEQ ID NO 79
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: phosphorothioate linkage

<400> SEQUENCE: 79
tgcatcgatg ca                                                              12

<210> SEQ ID NO 80
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: phosphorothioate linkage

<400> SEQUENCE: 80
acgtagctac gt                                                              12

<210> SEQ ID NO 81
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(9)
<223> OTHER INFORMATION: phosphodiester linkage

<400> SEQUENCE: 81 tcgtcgttg                                                                   9

<210> SEQ ID NO 82
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphodiester linkage

<400> SEQUENCE: 82 tcgtcgtt                                                                    8

<210> SEQ ID NO 83
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphodiester linkage

<400> SEQUENCE: 83
cagagctctg                                                               10

<210> SEQ ID NO 84
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ctgacgttct ctgt                                                          14

<210> SEQ ID NO 85
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ctgacgttct ctgt                                                          14

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ctatctgacg ttctctgt                                                      18

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: 7-deaza-dG
<220> FEATURE:
<221> NAME/KEY: modified_base
<222> LOCATION: (18)
<223> OTHER INFORMATION: 7-deaza-dG

<400> SEQUENCE: 87
tctgacnttc ttctgacntt ct                                                 22

<210> SEQ ID NO 88
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 88
tctgacgttc ttctgacgtt ct                                              22

<210> SEQ ID NO 89
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
ctgacgttct ctgtctgacg ttctctgt                                        28

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)
<223> OTHER INFORMATION: 5OHdC
<220> FEATURE:
<221> NAME/KEY: modified_base
<222> LOCATION: (17)
<223> OTHER INFORMATION: 5OHdC

<400> SEQUENCE: 90
tctgangttc ttctgangtt ct                                              22

<210> SEQ ID NO 91
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(17)
<223> OTHER INFORMATION: phosphorothioate linkage

<400> SEQUENCE: 91
ctgtctgacg ttctctg                                                    17

<210> SEQ ID NO 92
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate linkage

<400> SEQUENCE: 92
ctgtctgacg ttctctggaa cagag                                           25

<210> SEQ ID NO 93
```

```
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(31)
<223> OTHER INFORMATION: phosphorothioate linkage

<400> SEQUENCE: 93
ctgtctgacg ttctctggaa cagagaacgt c                              31

<210> SEQ ID NO 94
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(37)
<223> OTHER INFORMATION: phosphorothioate linkage

<400> SEQUENCE: 94
ctgtctgacg ttctctggaa cagagaacgt cagacag                        37

<210> SEQ ID NO 95
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate linkage

<400> SEQUENCE: 95
gacaggaact gtctgacgtt ctctg                                     25

<210> SEQ ID NO 96
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(32)
<223> OTHER INFORMATION: phosphorothioate linkage

<400> SEQUENCE: 96
aacgtcagac aggaactgtc tgacgttctc tg                             32

<210> SEQ ID NO 97
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(37)
<223> OTHER INFORMATION: phosphorothioate linkage
```

<400> SEQUENCE: 97
cagagaacgt cagacaggaa ctgtctgacg ttctctg        37

<210> SEQ ID NO 98
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: phosphorothioate linkage

<400> SEQUENCE: 98
ctatctgacg ttctctgt        18

<210> SEQ ID NO 99
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(18)
<223> OTHER INFORMATION: phosphorothioate linkage
<220> FEATURE:
<221> NAME/KEY: misc_feature
<222> LOCATION: (19)..(26)
<223> OTHER INFORMATION: phosphodiester linkage

<400> SEQUENCE: 99
ctatctgacg ttctctgtgt gatcac        26

<210> SEQ ID NO 100
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphodiester linkage
<220> FEATURE:
<221> NAME/KEY: misc_feature
<222> LOCATION: (9)..(26)
<223> OTHER INFORMATION: phosphorothioate linkage

<400> SEQUENCE: 100
gtgatcacct atctgacgtt ctctgt        26

<210> SEQ ID NO 101
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(17)
<223> OTHER INFORMATION: phosphorothioate linkage

<400> SEQUENCE: 101
ctgtctgtcg ttctctg        17

```
<210> SEQ ID NO 102
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate linkage

<400> SEQUENCE: 102
ctgtctgtcg ttctctggaa cagag                                           25

<210> SEQ ID NO 103
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(31)
<223> OTHER INFORMATION: phosphorothioate linkage

<400> SEQUENCE: 103
ctgtctgtcg ttctctggaa cagagaacga c                                    31

<210> SEQ ID NO 104
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(37)
<223> OTHER INFORMATION: phosphorothioate linkage

<400> SEQUENCE: 104
ctgtctgtcg ttctctggaa cagagaacga cagacag                              37

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate linkage

<400> SEQUENCE: 105
gacaggaact gtctgtcgtt ctctg                                           25

<210> SEQ ID NO 106
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
```

```
<222> LOCATION: (1)..(32)
<223> OTHER INFORMATION: phosphorothioate linkage

<400> SEQUENCE: 106
aacgacagac aggaactgtc tgacgttctc tg                                32

<210> SEQ ID NO 107
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(37)
<223> OTHER INFORMATION: phosphorothioate linkage

<400> SEQUENCE: 107
cagagaacga cagacaggaa ctgtctgtcg ttctctg                           37

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate linkage

<400> SEQUENCE: 108
tcgtcgttga gctctgaaag agctc                                        25

<210> SEQ ID NO 109
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: phosphorothioate linkage

<400> SEQUENCE: 109
tcgtcgttgt gagctctgtg aaacagagct cac                               33

<210> SEQ ID NO 110
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(41)
<223> OTHER INFORMATION: phosphorothioate linkage

<400> SEQUENCE: 110
tcgtcgttgc acagagctct gctgaaagca gagctctgtg c                      41

<210> SEQ ID NO 111
<211> LENGTH: 49
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(49)
<223> OTHER INFORMATION: phosphorothioate linkage

<400> SEQUENCE: 111
tcgtcgttgc tgacagagct ctgctatgaa atagcagagc tctgtcagc            49

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate linkage

<400> SEQUENCE: 112
tcgtcgttgt gctctgaact tgctc                                      25

<210> SEQ ID NO 113
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(33)
<223> OTHER INFORMATION: phosphorothioate linkage

<400> SEQUENCE: 113
tcgtcgttgt gtgctctgtg aacatcagtc tac                             33

<210> SEQ ID NO 114
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphorothioate linkage
<220> FEATURE:
<221> NAME/KEY: misc_feature
<222> LOCATION: (9)..(15)
<223> OTHER INFORMATION: phosphodiester linkage
<220> FEATURE:
<221> NAME/KEY: misc_feature
<222> LOCATION: (16)..(18)
<223> OTHER INFORMATION: phosphorothioate linkage
<220> FEATURE:
<221> NAME/KEY: misc_feature
<222> LOCATION: (19)..(25)
<223> OTHER INFORMATION: phosphodiester linkage

<400> SEQUENCE: 114
tcgtcgttga gctctgaaag agctc                                      25

<210> SEQ ID NO 115
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphorothioate linkage
<220> FEATURE:
<221> NAME/KEY: misc_feature
<222> LOCATION: (9)..(19)
<223> OTHER INFORMATION: phosphodiester linkage
<220> FEATURE:
<221> NAME/KEY: misc_feature
<222> LOCATION: (20)..(22)
<223> OTHER INFORMATION: phosphorothioate linkage
<220> FEATURE:
<221> NAME/KEY: misc_feature
<222> LOCATION: (23)..(33)
<223> OTHER INFORMATION: phosphodiester linkage

<400> SEQUENCE: 115
tcgtcgttgt gagctctgtg aaacagagct cac                                33

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(25)
<223> OTHER INFORMATION: 2'-O-methyl-ribonucleotide
<220> FEATURE:
<221> NAME/KEY: misc_feature
<222> LOCATION: (1)..(25)
<223> OTHER INFORMATION: phosphorothioate linkage

<400> SEQUENCE: 116
tcgtcgttga gctctgaaag agctc                                         25

<210> SEQ ID NO 117
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(33)
<223> OTHER INFORMATION: 2'-O-methyl-ribonucleotide
<220> FEATURE:
<221> NAME/KEY: misc_feature
<222> LOCATION: (1)..(33)
<223> OTHER INFORMATION: phosphorothioate linkage

<400> SEQUENCE: 117
tcgtcgttgt gagctctgtg aaacagagct cac                                33

<210> SEQ ID NO 118
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
```

```
<223> OTHER INFORMATION: 2'-deoxy-7-deaza-G
<220> FEATURE:
<221> NAME/KEY: modified_base
<222> LOCATION: (6)
<223> OTHER INFORMATION: 2'-deoxy-7-deaza-G
<220> FEATURE:
<221> NAME/KEY: misc_feature
<222> LOCATION: (1)..(25)
<223> OTHER INFORMATION: phosphorothioate linkage

<400> SEQUENCE: 118
tcntcnttga gctctgaaag agctc                                                25

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: AraG
<220> FEATURE:
<221> NAME/KEY: modified_base
<222> LOCATION: (6)
<223> OTHER INFORMATION: AraG
<220> FEATURE:
<221> NAME/KEY: misc_feature
<222> LOCATION: (1)..(25)
<223> OTHER INFORMATION: phosphorothioate linkage

<400> SEQUENCE: 119
tcntcnttga gctctgaaag agctc                                                25

<210> SEQ ID NO 120
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate linkage

<400> SEQUENCE: 120
tgctgcttga gctctgaaag agctc                                                25

<210> SEQ ID NO 121
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: phosphorothioate linkage

<400> SEQUENCE: 121
tcttgacgtt ctctct                                                          16

<210> SEQ ID NO 122
<211> LENGTH: 25
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate linkage

<400> SEQUENCE: 122
tcttgacgtt ctctctgaaa gagag                                          25

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(19)
<223> OTHER INFORMATION: phosphorothioate linkage
<220> FEATURE:
<221> NAME/KEY: misc_feature
<222> LOCATION: (20)..(25)
<223> OTHER INFORMATION: phosphodiester linkage

<400> SEQUENCE: 123
tcttgacgtt ctctctgaaa gagag                                          25

<210> SEQ ID NO 124
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: phosphodiester linkage
<220> FEATURE:
<221> NAME/KEY: misc_feature
<222> LOCATION: (17)..(25)
<223> OTHER INFORMATION: phosphorothioate linkage

<400> SEQUENCE: 124
tcttgacgtt ctctctgaaa gagag                                          25

<210> SEQ ID NO 125
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: phosphodiester linkage
<220> FEATURE:
<221> NAME/KEY: misc_feature
<222> LOCATION: (17)..(19)
<223> OTHER INFORMATION: phosphorothioate linkage
<220> FEATURE:
<221> NAME/KEY: misc_feature
<222> LOCATION: (20)..(25)
<223> OTHER INFORMATION: phosphodiester linkage

<400> SEQUENCE: 125
tcttgacgtt ctctctgaaa gagag                                          25

```
<210> SEQ ID NO 126
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphodiester linkage

<400> SEQUENCE: 126
tcttgacgtt ctctctgaaa gagag                                            25

<210> SEQ ID NO 127
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: phosphorothioate linkage

<400> SEQUENCE: 127
tcttgacgtt ctctct                                                      16

<210> SEQ ID NO 128
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: phosphodiester linkage

<400> SEQUENCE: 128
tcttgacgtt ctctct                                                      16

<210> SEQ ID NO 129
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(8)
<223> OTHER INFORMATION: phosphorothioate linkage

<400> SEQUENCE: 129 tcgtcgtt                                                               8

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(9)
<223> OTHER INFORMATION: phosphorothioate linkage
```

```
<220> FEATURE:
<221> NAME/KEY: misc_feature
<222> LOCATION: (10)..(21)
<223> OTHER INFORMATION: phosphodiester linkage

<400> SEQUENCE: 130
tcgtcgttgt gcatcgatgc a                                                    21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(9)
<223> OTHER INFORMATION: phosphodiester linkage
<220> FEATURE:
<221> NAME/KEY: misc_feature
<222> LOCATION: (10)..(21)
<223> OTHER INFORMATION: phosphorothioate linkage

<400> SEQUENCE: 131
tcgtcgttgt gcatcgatgc a                                                    21

<210> SEQ ID NO 132
<211> LENGTH: 25
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(25)
<223> OTHER INFORMATION: 2'-OMe-nucleoside
<220> FEATURE:
<221> NAME/KEY: misc_feature
<222> LOCATION: (1)..(25)
<223> OTHER INFORMATION: phosphorothioate linkage

<400> SEQUENCE: 132
tcgtcgttga gcucugaaag agcuc                                                25

<210> SEQ ID NO 133
<211> LENGTH: 29
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(29)
<223> OTHER INFORMATION: 2'-OMe-nucleoside
<220> FEATURE:
<221> NAME/KEY: misc_feature
<222> LOCATION: (1)..(29)
<223> OTHER INFORMATION: phosphorothioate linkage

<400> SEQUENCE: 133
tcgtcgttga gcucucugaa agagagcuc                                            29
```

```
<210> SEQ ID NO 134
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(33)
<223> OTHER INFORMATION: 2'-OMe-nucleoside
<220> FEATURE:
<221> NAME/KEY: misc_feature
<222> LOCATION: (1)..(33)
<223> OTHER INFORMATION: phosphorothioate linkage

<400> SEQUENCE: 134
tcgtcgttga gcucucugug aaacagagag cuc                             33

<210> SEQ ID NO 135
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: misc_feature
<222> LOCATION: (1)..(33)
<223> OTHER INFORMATION: phosphorothioate linkage

<400> SEQUENCE: 135
tcntcnttgt gagctctgtg aaacagagct cac                             33

<210> SEQ ID NO 136
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: misc_feature
<222> LOCATION: (1)..(8)
<223> OTHER INFORMATION: phosphorothioate linkage

<400> SEQUENCE: 136 tcntcntt                                                          8

<210> SEQ ID NO 137
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: misc_feature
<222> LOCATION: (1)..(25)
<223> OTHER INFORMATION: phosphorothioate linkage

<400> SEQUENCE: 137
gtgagctctg tgaaacagag ctcac                                              25

<210> SEQ ID NO 138
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: modified_base
<222> LOCATION: (20)..(33)
<223> OTHER INFORMATION: 2'-OMe-nucleoside
<220> FEATURE:
<221> NAME/KEY: misc_feature
<222> LOCATION: (1)..(33)
<223> OTHER INFORMATION: phosphorothioate linkage

<400> SEQUENCE: 138
tcntcnttgt gagctctgtg aaacagagcu cac                                     33

<210> SEQ ID NO 139
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphorothioate linkage

<400> SEQUENCE: 139
cagagctctg                                                               10

<210> SEQ ID NO 140
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: 2'-OMe-nucleoside
<220> FEATURE:
<221> NAME/KEY: misc_feature
<222> LOCATION: (1)..(10)
<223> OTHER INFORMATION: phosphorothioate linkage

<400> SEQUENCE: 140
```
cagagcucug                                                          10

<210> SEQ ID NO 141
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanoise
<220> FEATURE:
<221> NAME/KEY: modified_base
<222> LOCATION: (6)
<223> OTHER INFORMATION: 2'-deoxy-7-deazaguanoise

<400> SEQUENCE: 141 tcntcntt                                                            8

<210> SEQ ID NO 142
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: 2'-OMe-nucleoside
<220> FEATURE:
<221> NAME/KEY: misc_feature
<222> LOCATION: (1)..(10)
<223> OTHER INFORMATION: phosphodiester linkage

<400> SEQUENCE: 142
cagagcucug                                                          10

<210> SEQ ID NO 143
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(10)
<223> OTHER INFORMATION: phosphorothioate linkage

<400> SEQUENCE: 143
ctcacctctg                                                          10

<210> SEQ ID NO 144
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: 2'-OMe-nucleoside
<220> FEATURE:
<221> NAME/KEY: misc_feature
<222> LOCATION: (1)..(10)
<223> OTHER INFORMATION: phosphorothioate linkage

<400> SEQUENCE: 144
cucaccucug                                                              10

<210> SEQ ID NO 145
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: modified_base
<222> LOCATION: (20)..(33)
<223> OTHER INFORMATION: 2'-OMe-nucleoside
<220> FEATURE:
<221> NAME/KEY: misc_feature
<222> LOCATION: (1)..(33)
<223> OTHER INFORMATION: phosphorothioate linkage

<400> SEQUENCE: 145
tcntcnttgt gagctctgtg aaacagagcu cac                                    33

<210> SEQ ID NO 146
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(25)
<223> OTHER INFORMATION: 2'-OMe-nucleoside
<220> FEATURE:
<221> NAME/KEY: misc_feature
<222> LOCATION: (1)..(25)
<223> OTHER INFORMATION: phosphorothioate linkage

<400> SEQUENCE: 146
gugagcucug ugaaacagag cucac                                             25

<210> SEQ ID NO 147
<211> LENGTH: 34
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(34)
<223> OTHER INFORMATION: 2'-OMe-nucleoside
<220> FEATURE:
<221> NAME/KEY: misc_feature
<222> LOCATION: (1)..(8)
<223> OTHER INFORMATION: phosphorothioate linkage
<220> FEATURE:
<221> NAME/KEY: misc_feature
<222> LOCATION: (9)..(20)
<223> OTHER INFORMATION: phosphodiester linkage

```
<220> FEATURE:
<221> NAME/KEY: misc_feature
<222> LOCATION: (21)..(23)
<223> OTHER INFORMATION: phosphorothioate linkage
<220> FEATURE:
<221> NAME/KEY: misc_feature
<222> LOCATION: (24)..(34)
<223> OTHER INFORMATION: phosphodiester linkage

<400> SEQUENCE: 147
tcgtcgttgt gagctctgtg gaaacagagc ucac                              34

<210> SEQ ID NO 148
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 148
tcnaacnttc n                                                       11

<210> SEQ ID NO 149
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine

<400> SEQUENCE: 149
tcnaacnttc g                                                       11

<210> SEQ ID NO 150
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tctcaccttc t                                                       11

<210> SEQ ID NO 151
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (3)
<223> OTHER INFORMATION: AraG
<220> FEATURE:
<221> NAME/KEY: modified_base
<222> LOCATION: (7)
<223> OTHER INFORMATION: AraG
<220> FEATURE:
<221> NAME/KEY: modified_base
<222> LOCATION: (11)
<223> OTHER INFORMATION: AraG

<400> SEQUENCE: 151
tcnaacnttc n                                                              11

<210> SEQ ID NO 152
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: AraG
<220> FEATURE:
<221> NAME/KEY: modified_base
<222> LOCATION: (7)
<223> OTHER INFORMATION: AraG

<400> SEQUENCE: 152
tcnaacnttc g                                                              11

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: modified_base
<222> LOCATION: (10)
<223> OTHER INFORMATION: 2'-deoxy-7-deazaguanosine
<220> FEATURE:
<221> NAME/KEY: modified_base
<222> LOCATION: (14)
<223> OTHER INFORMATION: 2'-deoxy-7-deazaguanosine

<400> SEQUENCE: 153
tcntcnaacn ttcnagatga t                                                   21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
```

```
<223> OTHER INFORMATION: AraG
<220> FEATURE:
<221> NAME/KEY: modified_base
<222> LOCATION: (6)
<223> OTHER INFORMATION: AraG
<220> FEATURE:
<221> NAME/KEY: modified_base
<222> LOCATION: (10)
<223> OTHER INFORMATION: AraG
<220> FEATURE:
<221> NAME/KEY: modified_base
<222> LOCATION: (14)
<223> OTHER INFORMATION: AraG

<400> SEQUENCE: 154
tcntcnaacn ttcnagatga t                                              21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxyinosine
<220> FEATURE:
<221> NAME/KEY: modified_base
<222> LOCATION: (6)
<223> OTHER INFORMATION: 2'-deoxyinosine
<220> FEATURE:
<221> NAME/KEY: modified_base
<222> LOCATION: (10)
<223> OTHER INFORMATION: 2'-deoxyinosine
<220> FEATURE:
<221> NAME/KEY: modified_base
<222> LOCATION: (14)
<223> OTHER INFORMATION: 2'-deoxyinosine

<400> SEQUENCE: 155
tcntcnaacn ttcnagatga t                                              21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 1-(2'-deoxy-beta-D-ribofuranosyl)-2-oxo-7-
      deaza-8-methylpurine
<220> FEATURE:
<221> NAME/KEY: modified_base
<222> LOCATION: (5)
<223> OTHER INFORMATION: 1-(2'-deoxy-beta-D-ribofuranosyl)-2-oxo-7-
      deaza-8-methylpurine
<220> FEATURE:
<221> NAME/KEY: modified_base
<222> LOCATION: (9)
<223> OTHER INFORMATION: 1-(2'-deoxy-beta-D-ribofuranosyl)-2-oxo-7-
      deaza-8-methylpurine
<220> FEATURE:
<221> NAME/KEY: modified_base
<222> LOCATION: (13)
<223> OTHER INFORMATION: 1-(2'-deoxy-beta-D-ribofuranosyl)-2-oxo-7-
      deaza-8-methylpurine

<400> SEQUENCE: 156
tngtngaang ttngagatga t                                              21
```

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: AraC
<220> FEATURE:
<221> NAME/KEY: modified_base
<222> LOCATION: (5)
<223> OTHER INFORMATION: AraC
<220> FEATURE:
<221> NAME/KEY: modified_base
<222> LOCATION: (9)
<223> OTHER INFORMATION: AraC
<220> FEATURE:
<221> NAME/KEY: modified_base
<222> LOCATION: (13)
<223> OTHER INFORMATION: AraC

<400> SEQUENCE: 157
tngtngaang ttngagatga t                                          21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)
<223> OTHER INFORMATION: 2'-deoxy-5-hydroxycytidine
<220> FEATURE:
<221> NAME/KEY: modified_base
<222> LOCATION: (5)
<223> OTHER INFORMATION: 2'-deoxy-5-hydroxycytidine
<220> FEATURE:
<221> NAME/KEY: modified_base
<222> LOCATION: (9)
<223> OTHER INFORMATION: 2'-deoxy-5-hydroxycytidine
<220> FEATURE:
<221> NAME/KEY: modified_base
<222> LOCATION: (13)
<223> OTHER INFORMATION: 2'-deoxy-5-hydroxycytidine

<400> SEQUENCE: 158
tngtngaang ttngagatga t                                          21

<210> SEQ ID NO 159
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine

<400> SEQUENCE: 159 tcnaacnttc                                                       10

<210> SEQ ID NO 160
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 160
tcnttcnaac n                                                              11

<210> SEQ ID NO 161
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tccaaccttc g                                                              11

<210> SEQ ID NO 162
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 2'-deoxy-7-deazaguanosine
<220> FEATURE:
<221> NAME/KEY: modified_base
<222> LOCATION: (11)
<223> OTHER INFORMATION: 2'-deoxy-7-deazaguanosine

<400> SEQUENCE: 162
tcnttncaac n                                                              11

<210> SEQ ID NO 163
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: AraG
<220> FEATURE:
<221> NAME/KEY: modified_base
<222> LOCATION: (7)

-continued

```
<223> OTHER INFORMATION: AraG

<400> SEQUENCE: 163
tcnaacnttc t                                                            11

<210> SEQ ID NO 164
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (7)
<223> OTHER INFORMATION: AraG
<220> FEATURE:
<221> NAME/KEY: modified_base
<222> LOCATION: (11)
<223> OTHER INFORMATION: 2'-deoxy-7-deazaguanosine

<400> SEQUENCE: 164
tcnaacnttc n                                                            11

<210> SEQ ID NO 165
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2'-deoxy-7-deazaguanosine
<220> FEATURE:
<221> NAME/KEY: modified_base
<222> LOCATION: (6)
<223> OTHER INFORMATION: 1-(2'-deoxy-beta-D-ribofuranosyl)-2-oxo-7-
      deaza-8-methylpurine
<220> FEATURE:
<221> NAME/KEY: modified_base
<222> LOCATION: (11)
<223> OTHER INFORMATION: 2'-deoxy-7-deazaguanosine

<400> SEQUENCE: 165
tcnaangttc n                                                            11
```

SYNERGISTIC STIMULATION OF THE IMMUNE SYSTEM USING IMMUNOSTIMULATORY OLIGONUCLEOTIDES AND/OR IMMUNOMER COMPOUNDS IN CONJUNCTION WITH CYTOKINES AND/OR CHEMOTHERAPEUTIC AGENTS OR RADIATION THERAPY

RELATED APPLICATIONS

This Application claims priority to U.S. patent application Ser. No. 10/892,550, filed Jul. 15, 2004, which claims the benefit of U.S. Provisional Application 60/487,529, filed Jul. 15, 2003 and U.S. Provisional Application 60/503,242, filed Sep. 15, 2003. The entire teachings of the above-referenced Applications are incorporated herein by reference.

BACKGROUND OF THE INVENTION

1. Field of the Invention

The invention relates to the use of immunomer compounds and immunostimulatory oligonucleotides as therapeutic agents.

2. Summary of the Related Art

Recently, several researchers have demonstrated the validity of the use of oligonucleotides as immunostimulatory agents in immunotherapy applications. The observation that phosphodiester and phosphorothioate oligonucleotides can induce immune stimulation has created interest in developing these compounds as a therapeutic tool. These efforts have focused on phosphorothioate oligonucleotides containing the natural dinucleotide CpG. Kuramoto et al., *Jpn. J. Cancer Res.* 83:1128-1131 (1992) teaches that phosphodiester oligonucleotides containing a palindrome that includes a CpG dinucleotide can induce interferon-alpha and gamma synthesis and enhance natural killer activity. Krieg et al., *Nature* 371:546-549 (1995) discloses that phosphorothioate CpG-containing oligonucleotides are immunostimulatory. Liang et al., *J. Clin. Invest.* 98:1119-1129 (1996) discloses that such oligonucleotides activate human B cells. Moldoveanu et al., *Vaccine* 16:1216-124 (1998) teaches that CpG-containing phosphorothioate oligonucleotides enhance immune response against influenza virus. McCluskie and Davis, *J. Immunol.* 161:4463-4466 (1998) teaches that CpG-containing oligonucleotides act as potent adjuvants, enhancing immune response against hepatitis B surface antigen.

Other modifications of CpG-containing phosphorothioate oligonucleotides can also affect their ability to act as modulators of immune response. See, e.g., Zhao et al., *Biochem. Pharmacol.* (1996) 51:173-182; Zhao et al., *Biochem Pharmacol.* (1996) 52:1537-1544; Zhao et al., *Antisense Nucleic Acid Drug Dev.* (1997) 7:495-502; Zhao et al., *Bioorg. Med Chem. Lett.* (1999) 9:3453-3458; Zhao et al., *Bioorg. Med Chem. Lett.* (2000) 10:1051-1054; Yu et al., *Bioorg. Med. Chem. Lett.* (2000) 10:2585-2588; Yu et al., *Bioorg. Med. Chem. Lett.* (2001) 11:2263-2267; and Kandimalla et al., *Bioorg. Med Chem.* (2001) 9:807-813. U.S. Pat. No. 6,426,334 shows the promise of these compounds as anti-cancer agents.

Another means by which an immune response may be modulated is through the therapeutic use of cytokines. Cytokines are soluble molecules that cells of the immune system produce to control reactions between other cells. Thus, cytokines are regulators of humoral and cellular immunity. An understanding of how T cells mediate the immune response is critical in order to modulate the response. CD4+ T helper (Th) cells differentiate along either the Th1 or Th2 pathway. The Th1 pathway is important for the generation of cell-mediated immunity and is characterized by the production of, for example, γ-interferon and interleukin-2 (IL-2). The Th2 response is important for the generation of humoral immunity and is characterized by the production of, for example, IL-4 and IL-5. The Th1 response is known to be critical for immune system defense against infections, e.g., viral infections, and immune system surveillance of the body for the removal of neoplastic cells.

Krieg, A., M. et al. (U.S. Pat. No. 6,429,199) and Krieg, A., M. et al. (U.S. Pat. No. 6,218,371) purport to teach the co-administration of immunostimulatory CpG oligonucleotides and cytokines, particularly GM-CSF. Decker et al. (*Experimental Hematology* 28:558-565. (2000)), demonstrate that the co-administration of IL-2 with CpG oligonucleotides increases TNF-α and IL-6 production in B-chronic lymphocytic (B-CLL) cells but not in normal B-cells.

These reports make clear that there remains a need to be able to further optimize the therapeutic effectiveness of immunostimulatory oligonucleotides for the treatment of disease and enhance the anticancer activity of immunostimulatory oligonucleotides.

BRIEF SUMMARY OF THE INVENTION

The invention provides optimized methods, compositions and treatment regimens for enhancing the immune response caused by immunostimulatory compounds used for the treatment of disease such as, but not limited to, treatment of cancer, autoimmune disorders, asthma, respiratory allergies, food allergies and infectious diseases in a patient. The optimized methods according to the invention provide synergy between the therapeutic effects of immunostimulatory oligonucleotides in accordance with the invention, and the therapeutic effect of cytokine immunotherapy and/or chemotherapeutic agents. Modification of an immunostimulatory oligonucleotide to optimally present 5' ends dramatically enhances its anti-cancer activity. Such an oligonucleotide is referred to herein as an "immunomer", which may contain one or more immunostimulatory oligonucleotide.

In a first aspect, therefore, the invention provides methods for treating cancer in a cancer patient comprising administering to the patient an immunostimulatory oligonucleotide and/or immunomer compound in combination with a chemotherapeutic agent, wherein the immunostimulatory oligonucleotide and/or immunomer compound and the chemotherapeutic agent create a synergistic therapeutic effect.

In a further aspect, the invention provides a method for synergistically stimulating an immune response in a patient. The method comprises administering to a patient a combination of a therapeutically effective synergistic amount of at least one immunomer compound or immunostimulatory oligonucleotide in accordance with the invention and a therapeutically effective synergistic amount of IL-2 (and/or an agent that induces IL-2 production in situ, such as a DNA vaccine or expression vector expressing IL-2), wherein administration of said combination synergistically stimulates the production of cytokines in a patient. Preferred cytokines that are synergistically stimulated in accordance with the invention are selected from the group consisting of, IL-12 and interferon-γ (IFN-γ), IFN-α, IFN-β or combinations thereof.

In accordance with the invention, an "immunomer" refers to any compound comprising at least two oligonucleotides linked directly at their 3' ends, or directly via internucleoside linkages, or directly at a functionalized nucleobase or sugar, or that are indirectly linked together via a non-nucleotidic linker, wherein at least one of the oligonucleotides, in the context of the immunomer compound, is an immunostimulatory oligonucleotide having an accessible 5' end. In the context of the invention, an immunostimulatory oligonucleotide is an oligonucleotide that comprises at least one of an immunostimulatory CpG dinucleotide, an immunostimulatory domain, or other immunostimulatory moiety. As used herein, the term "accessible 5' end" means that the 5' end of the oligonucleotide is sufficiently available such that the factors that recognize and bind to immunomer compounds or immunostimulatory oligonucleotides and stimulate the immune system have access to the 5' end. Such immunostimulatory oligonucleotides may include secondary structures, provided that the 5' end remains accessible.

In some embodiments, the immunostimulatory oligonucleotide and/or immunomer compound used in the method according to the invention comprises an immunostimulatory dinucleotide selected from the group consisting of CpG, C*pG, CpG*, and C*pG*, wherein C is cytidine or 2'-deoxycytidine, C* is 2'-deoxythymidine. arabinocytidine, 2'-deoxy-2'-substituted arabinocytidine, 2'-O-substitutedarabinocytidine, 2'-deoxy-5-hydroxycytidine, 2'-deoxy-N4-alkyl-cytidine, 2'-deoxy-4-thiouridine, other non-natural pyrimidine nucleosides, or 1-(2'-deoxy-β-D-ribofuranosyl)-2-oxo-7-deaza-8-methyl-purine; G is guanosine or 2'-deoxyguanosine, G* is 2' deoxy-7-deazaguanosine, 2'-deoxy-6-thioguanosine, arabinoguanosine, 2'-deoxy-2'substituted-arabinoguanosine, 2'-O-substituted-arabinoguanosine, or other non-natural purine nucleoside, and p is an internucleoside linkage selected from the group consisting of phosphodiester, phosphorothioate, and phosphorodithioate. In certain preferred embodiments, the immunostimulatory dinucleotide is not CpG.

In some embodiments, the immunostimulatory oligonucleotide and/or immunomer compound used in the method according to the invention comprises an immunostimulatory domain of formula (III):

5'-Nn-N1-Y-Z-N1-Nn-3'        (III)

wherein:

Y is cytidine, 2'-deoxythymidine, 2'-deoxycytidine, arabinocytidine, 2'-deoxy-2'-substitutedarabinocytidine, 2'-O-substitutedarabinocytidine, 2'-deoxy-5-hydroxycytidine, 2'-deoxy-N4-alkyl-cytidine, 2'-deoxy-4-thiouridine, other non-natural pyrimidine nucleosides, or 1-(2'-deoxy-β-D-ribofuranosyl)-2-oxo-7-deaza-8-methyl-purine;

Z is guanosine or 2'-deoxyguanosine, is 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other non-natural purine nucleoside N1, at each occurrence, is preferably a naturally occurring or a synthetic nucleoside or an immunostimulatory moiety selected from the group consisting of abasic nucleosides, arabinonucleosides, 2'-deoxyuridine, α-deoxyribonucleosides, β-L-deoxyribonucleosides, and nucleosides linked by a phosphodiester or modified internucleoside linkage to the adjacent nucleoside on the 3' side, the modified internucleotide linkage being selected from, without limitation, a linker having a length of from about 2 angstroms to about 200 angstroms, C2-C18 alkyl linker, poly(ethylene glycol) linker, 2-aminobutyl-1,3-propanediol linker, glyceryl linker, 2'-5' internucleoside linkage, and phosphorothioate, phosphorodithioate, or methylphosphonate internucleoside linkage;

Nn, at each occurrence, is independently a naturally occurring nucleoside or an immunostimulatory moiety, preferably selected-from the group-consisting of abasic nucleosides, arabinonucleosides, 2'-deoxyuridine, a-deoxyribonucleosides, 2'-O-substituted ribonucleosides, and nucleosides linked by a modified internucleoside linkage to the adjacent nucleoside on the 3' side, the modified internucleotide linkage being selected from the group consisting of amino linker, C2-C18 alkyl linker, poly(ethylene glycol) linker, 2-aminobutyl-1,3-propanediol linker, glyceryl linker, 2'-5' internucleoside linkage, and methylphosphonate internucleoside linkage;

provided that at least one N1 or Nn is an immunostimulatory moiety;

wherein n is a number from 0-30;

wherein the 3'nucleoside is optionally linked directly or via a non-nucleotidic linker to another oligonucleotide, which may or may not be immunostimulatory.

In a second aspect, the invention provides a method for treating cancer in a cancer patient comprising administering an immunostimulatory oligonucleotide and/or immunomer conjugate, which comprises an immunostimulatory oligonucleotide and/or immunomer compound, as described above, and a cancer antigen conjugated to the immunostimulatory oligonucleotide and/or immunomer compound at a position other than the accessible 5' end, in combination with a chemotherapeutic agent.

In a third aspect, the invention provides pharmaceutical formulations comprising an immunostimulatory oligonucleotide or immunostimulatory oligonucleotide conjugate and/or an immunomer compound or immunomer conjugate according to the invention, a chemotherapeutic agent and a physiologically acceptable carrier.

In a fourth aspect, the invention provides a method for sensitizing cancer cells to ionizing radiation. The method according to this aspect of the invention comprises administering to a mammal an immunostimulatory oligonucleotide or an immunomer compound according to the invention and treating the animal with ionizing radiation.

In a fifth aspect, the invention provides a method for synergistically stimulating an immune response in a patient comprising administering to a patient a therapeutically effective synergistic amount of at least one immunomer compound or immunostimulatory oligonucleotide in combination with a therapeutically effective synergistic amount of IL-2, (and optionally an antigen), wherein administration of said combination synergistically stimulates the production cytokines in a patient. Preferred cytokines that are synergistically stimulated in accordance with the invention are selected from the group consisting of IL-12 and interferon-γ, IFN-α, IFN-β or combinations thereof. In certain embodiments of this second aspect of the invention, the antigen is operationally associated with the immunomer compound at a position other than the accessible 5' end.

In a sixth aspect of the invention, at least one immunostimulatory oligonucleotide that is not an immunomer compound is used in combination with a therapeutically effective amount of IL-2 to selectively and synergistically stimulate the production cytokines in a patient. Preferred cytokines that are synergistically stimulated in accordance with the invention are selected from the group consisting of IL-12 and IFN-γ, IFN-α, IFN-β or combinations thereof. In accordance with the present invention, preferred immunostimulatory oligonucleotides that are not immunomer compounds include those containing at least one immunostimulatory CpG dinucleotide wherein C is not cytosine or deoxycytosine and/or G is not guanosine or 2-deoxyguanosine. Other preferred immunostimulatory oligonucleotides of the invention that are not immunomer compounds are those that include alternative immunostimulatory moieties that are not CpG. Examples of such alternative immunostimulatory moieties include but are not limited to nucleosides comprising non-naturally occurring bases and/or sugar and secondary structures of the oligonucleotide itself such as hairpin structures that stabilize the oligonucleotide.

In a seventh aspect, the invention provides therapeutic compositions comprising a therapeutically-effective synergistic amount of at least one immunomer compound, or immmunostimulatory oligonucleotide, a therapeutically effective synergistic amount of IL-2 (and/or an agent that induces IL-2 production in situ, such as a DNA vaccine or expression vector expressing IL-2) and optionally an antigen wherein administration of said combination synergistically stimulates the production of cytokines in a patient. Preferred cytokines that are synergistically stimulated in accordance with the invention are selected from the group consisting of IL-12 and IFN-γ, IFN-α, IFN-β or combinations thereof.

The methods and compositions according to all aspects of the invention are useful in therapeutic approaches to human or veterinary diseases involving immune system modulation and immune-based therapies. Particularly preferred disease targets include cancer, infectious diseases, asthma and allergies.

DETAILED DESCRIPTION OF THE PREFERRED EMBODIMENTS

Figure 1:
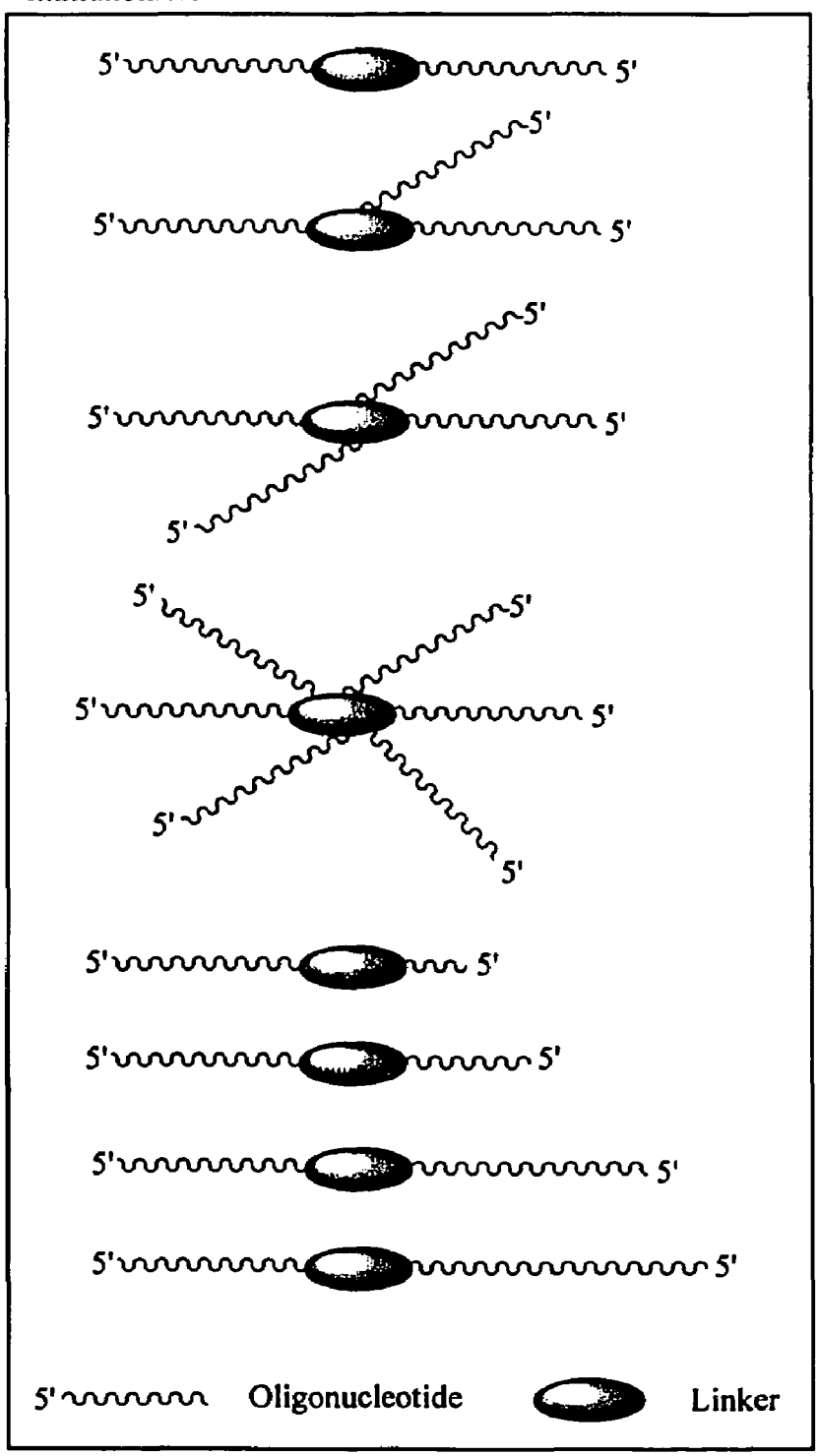
FIG. 1 is a schematic representation of representative immunomer compounds of the invention.
Figure 2:
FIG. 2 depicts several representative immunomer compounds of the invention (all oligonucleotides shown are SEQ ID NO: 4).
Figure 3:
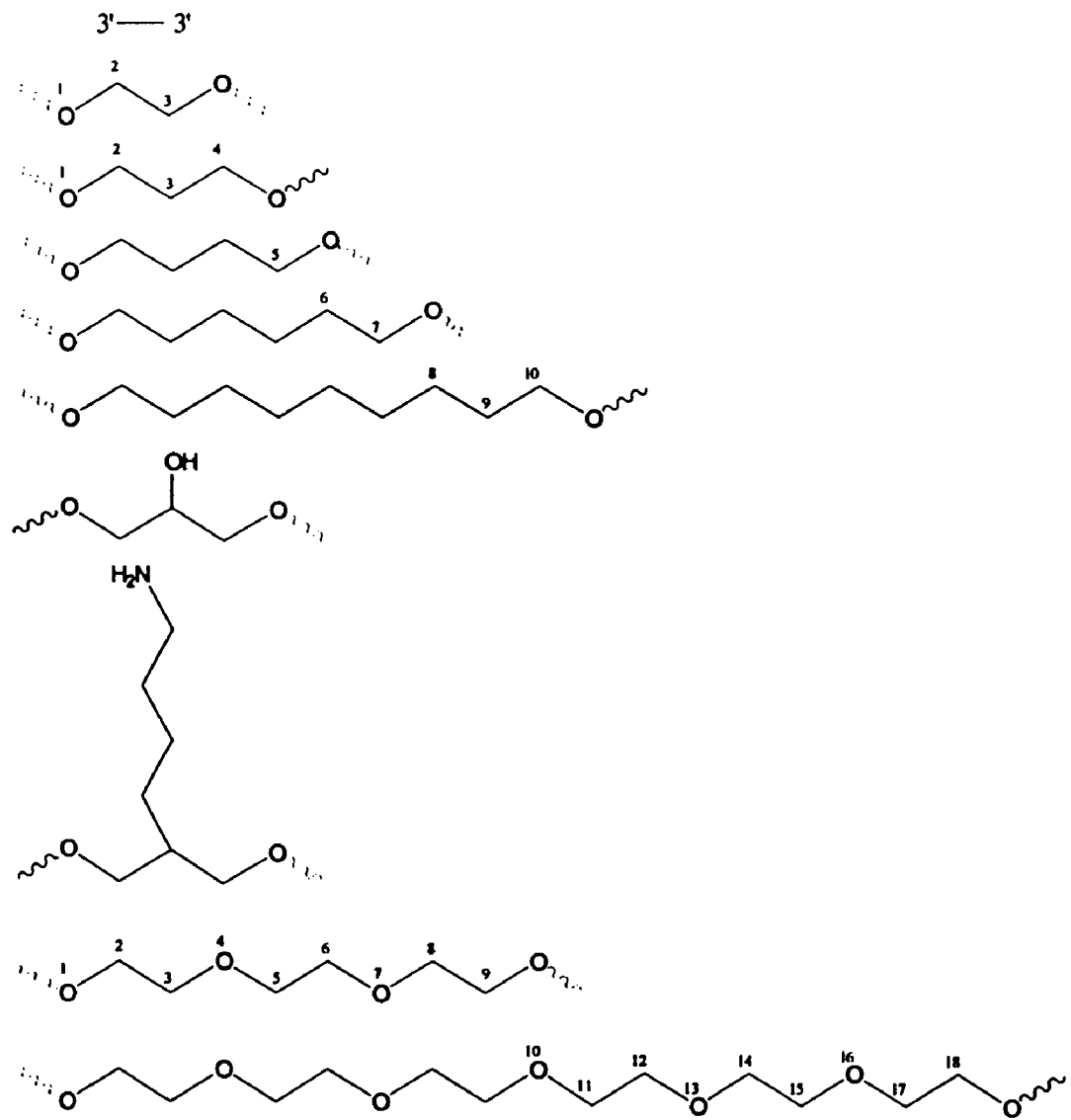
FIG. 3 depicts a group of representative small molecule linkers suitable for linear synthesis of immumomers of the invention.
Figure 4:
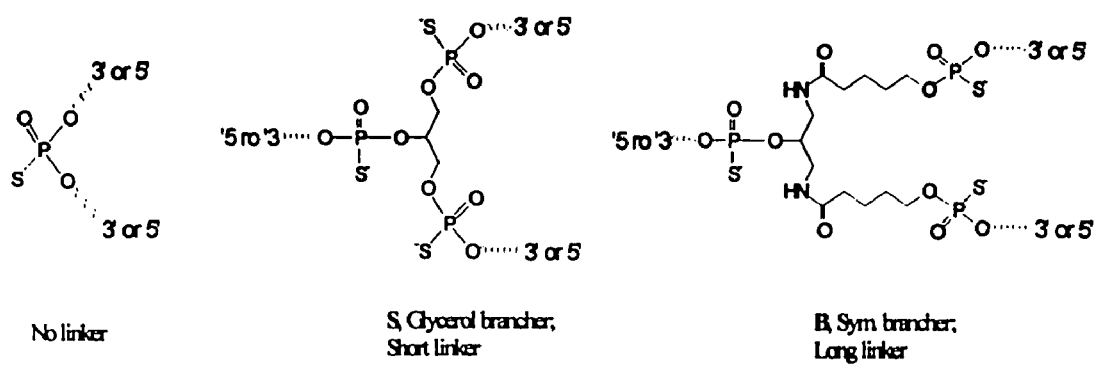
FIG. 4 depicts a group of representative small molecule linkers suitable for parallel synthesis of immunomer compounds of the invention.

The invention relates to optimized methods and compositions for enhancing the immune response caused by immunostimulatory compounds used in immune-based therapies. The optimized methods according to the invention result in synergy between the therapeutic effect of immunostimulatory compounds such as immunostimulatory oligonucleotides and immunomer compounds and the therapeutic effect of cytokine immunotherapy and/or chemotherapeutic agents. The issued patents, patent applications, and references that are cited herein are hereby incorporated by reference to the same extent as if each was specifically and individually indicated to be incorporated by reference. In the event of inconsistencies between any teaching of any reference cited herein and the present specification, the latter shall prevail for purposes of the invention.

The invention provides methods for enhancing the anticancer effect caused by immunostimulatory compounds used for immunotherapy applications for the treatment of cancer. In the methods according to the invention, immunostimulatory oligonucleotides and/or immunomer compounds provide a synergistic therapeutic effect when use in combination with chemotherapeutic agents. This result is surprising in view of the fact that immunostimulatory oligonucleotides and immunomer compounds cause cell division of immune system cells, whereas chemotherapeutic agents normally kill actively dividing cells.

In a first aspect, the invention provides a method for treating cancer in a cancer patient comprising administering, in combination with chemotherapeutic agents, immunostimulatory oligonucleotides and/or immunomer compounds, the latter comprising at least two oligonucleotides linked together, such that the immunomer compound has more than one accessible 5' end, wherein at least one of the oligonucleotides is an immunostimulatory oligonucleotide. As used herein, the term "accessible 5' end" means that the 5' end of the oligonucleotide is sufficiently available such that the factors that recognize and bind to immunomer compounds and stimulate the immune system have access to it. Optionally, the 5' OH can be linked to a phosphate, phosphorothioate, or phosphorodithioate moiety, an aromatic or aliphatic linker, cholesterol, or another entity which does not interfere with accessibility. Immunostimulatory oligonucleotides and immunomer compounds induce an immune response when administered to a vertebrate. When used in combination with chemotherapeutic agents, a synergistic therapeutic effect is obtained.

Preferred chemotherapeutic agents used in the method according to the invention include, without limitation Gemcitabine, methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Placlitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate.

In the methods according to this aspect of the invention, administration of immunostimulatory oligonucleotides and/or immunomer compounds can be by any suitable route, including, without limitation, parenteral, oral, sublingual, transdermal, topical, intranasal, aerosol, intraocular, intratracheal, intrarectal, vaginal, by gene gun, dermal patch or topical cream or in eye drop or mouthwash form. Administration of the therapeutic compositions of immunostimulatory oligonucleotides and/or immunomer compounds can be carried out using known procedures at dosages and for periods of time effective to reduce symptoms or surrogate markers of the disease. When administered systemically, the therapeutic composition is preferably administered at a sufficient dosage to attain a blood level of immunostimulatory oligonucleotide and/or immunomer compound from about 0.0001 micromolar to about 10 micromolar. For localized administration, much lower concentrations than this may be effective, and much higher concentrations may be tolerated. Preferably, a total dosage of immunostimulatory oligonucleotide and/or immunomer compound ranges from about 0.0001 mg per patient per day to about 200 mg per kg body weight per day. It may be desirable to administer simultaneously, or sequentially a therapeutically effective amount of one or more of the therapeutic compositions of the invention to an individual as a single treatment episode.

For purposes of this aspect of the invention, the term "in combination with" means in the course of treating the same disease in the same patient, and includes administering the immunostimulatory oligonucleotide and/or immunomer compound and/or the chemotherapeutic agent in any order, including simultaneous administration, as well as temporally spaced order of up to several days apart. Such combination treatment may also include more than a single administration of the immunostimulatory oligonucleotide and/or immunomer compound, and/or independently the chemotherapeutic agent. The administration of the immunostimulatory oligonucleotide and/or immunomer compound and/or chemotherapeutic agent may be by the same or different routes.

In some embodiments, the immunomer compound used in the method according to the invention comprises two or more immunostimulatory oligonucleotides, (in the context of the immunomer) which may be the same or different. Preferably, each such immunostimulatory oligonucleotide has at least one accessible 5' end.

In certain embodiments of the method according to the invention, in addition to the immunostimulatory oligonucleotide(s), the immunomer compound also comprises at least one oligonucleotide that is complementary to a gene. As used herein, the term "complementary to" means that the oligonucleotide hybridizes under physiological conditions to a region of the gene. In some embodiments, the oligonucleotide downregulates expression of a gene. Such downregulatory oligonucleotides preferably are selected from the group consisting of antisense oligonucleotides, ribozyme oligonucleotides, small inhibitory RNAs and decoy oligonucleotides. As used herein, the term "downregulate a gene" means to inhibit the transcription of a gene or translation of a gene product. Thus, the immunomer compounds used in the method according to the invention can be used to target one or more specific disease targets, while also stimulating the immune system.

In certain embodiments, the immunostimulatory oligonucleotide and/or immunomer compound used in the method according to the invention includes a ribozyme or a decoy oligonucleotide. As used herein, the term "ribozyme" refers to an oligonucleotide that possesses catalytic activity. Preferably, the ribozyme binds to a specific nucleic acid target and cleaves the target. As used herein, the term "decoy oligonucleotide" refers to an oligonucleotide that binds to a transcription factor in a sequence-specific manner and arrests transcription activity. Preferably, the ribozyme or decoy oligonucleotide exhibits secondary structure, including, without limitation, stem-loop or hairpin structures. In certain embodiments, at least one oligonucleotide comprises poly(I)-poly (dC). In certain embodiments, at least one set of Nn includes a string of 3 to 10 dGs and/or Gs or 2'-substituted ribo or arabino Gs.

For purposes of the invention, the term "oligonucleotide" refers to a polynucleoside formed from a plurality of linked nucleoside units. Such oligonucleotides can be obtained from existing nucleic acid sources, including genomic or cDNA, but are preferably produced by synthetic methods. In preferred embodiments each nucleoside unit includes a heterocyclic base and a pentofuranosyl, trehalose, arabinose, 2'-deoxy-2'-substituted arabinose, 2'-O-substituted arabinose or hexose sugar group. The nucleoside residues can be coupled to each other by any of the numerous known internucleoside linkages. Such internucleoside linkages include, without limitation, phosphodiester, phosphorothioate, phosphorodithioate, alkylphosphonate, alkylphosphonothioate, phosphotriester, phosphoramidate, siloxane, carbonate, carboalkoxy, acetamidate, carbamate, morpholino, borano, thioether, bridged phosphoramidate, bridged methylene phosphonate, bridged phosphorothioate, and sulfone internucleoside linkages. The term "oligonucleotide" also encompasses polynucleosides having one or more stereospecific internucleoside linkage (e.g., $(R_P)$- or $(S_P)$-phosphorothioate, alkylphosphonate, or phosphotriester linkages). As used herein, the terms "oligonucleotide" and "dinucleotide" are expressly intended to include polynucleosides and dinucleosides having any such internucleoside linkage, whether or not the linkage comprises a phosphate group. In certain preferred embodiments, these internucleoside linkages may be phosphodiester, phosphorothioate, phosphorodithioate, methylphosphonate linkages, or combinations thereof.

In some embodiments, the immunomer compound comprises oligonucleotides each having from about 3 to about 35 nucleoside residues, preferably from about 4 to about 30 nucleoside residues, more preferably from about 4 to about 20 nucleoside residues. In some embodiments, the oligonucleotides have from about 5 or 6 to about 18, or from about 5 or 6 to about 14, nucleoside residues. As used herein, the term "about" implies that the exact number is not critical. Thus, the number of nucleoside residues in the oligonucleotides is not critical, and oligonucleotides having one or two fewer nucleoside residues, or from one to several additional nucleoside residues are contemplated as equivalents of each of the embodiments described above, for purposes of this invention. In some embodiments, one or more of the oligonucleotides have 11 nucleotides.

The term "oligonucleotide" also encompasses polynucleosides having additional substituents including, without limitation, protein groups, lipophilic groups, intercalating agents, diamines, folic acid, cholesterol and adamantane. The term "oligonucleotide" also encompasses any other nucleobase containing polymer, including, without limitation, peptide nucleic acids (PNA), peptide nucleic acids with phosphate groups (PHONA), locked nucleic acids (LNA), morpholino-backbone oligonucleotides, and oligonucleotides having backbone sections with alkyl linkers or amino linkers.

The immunostimulatory oligonucleotides and/or immunomer compounds used in the method according to the invention can include naturally occurring nucleosides, modified nucleosides, or mixtures thereof. As used herein, the term "modified nucleoside" is a nucleoside that includes a modified heterocyclic base, a modified sugar moiety, or a combination thereof. In some embodiments, the modified nucleoside is a non-natural -pyrimidine or purine nucleoside, as herein described. In some embodiments, the modified nucleoside is a 2'-substituted ribonucleoside an arabinonucleoside or a 2'-deoxy-2'-fluoroarabinoside.

For purposes of the invention, the term "2'-substituted ribonucleoside" includes ribonucleosides in which the hydroxyl group at the 2' position of the pentose moiety is substituted to produce a 2'-O-substituted ribonucleoside. Preferably, such substitution is with a lower alkyl group containing 1-6 saturated or unsaturated carbon atoms, or with an aryl group having 6-10 carbon atoms, wherein such alkyl, or aryl group may be unsubstituted or may be substituted, e.g., with halo, hydroxy, trifluoromethyl, cyano, nitro, acyl, acyloxy, alkoxy, carboxyl, carboalkoxy, or amino groups. Examples of such 2'-O-substituted ribonucleosides include, without limitation 2'-O-methylribonucleosides and 2'-O-methoxyethylribonucleosides.

The term "2'-substituted ribonucleoside" also includes ribonucleosides in which the 2'-hydroxyl group is replaced with a lower alkyl group containing 1-6 saturated or unsaturated carbon atoms, or with an amino or halo group. Examples of such 2'-substituted ribonucleosides include, without limitation, 2'-amino, 2'-fluoro, 2'-allyl, and 2'-propargyl ribonucleosides.

The term "oligonucleotide" includes hybrid and chimeric oligonucleotides. A "chimeric oligonucleotide" is an oligonucleotide having more than one type of internucleoside linkage. One preferred example of such a chimeric oligonucleotide is a chimeric oligonucleotide comprising a phosphorothioate, phosphodiester or phosphorodithioate region and non-ionic linkages such as alkylphosphonate or alkylphosphonothioate linkages (see e.g., Pederson et al. U.S. Pat. Nos. 5,635,377 and 5,366,878).

A "hybrid oligonucleotide" is an oligonucleotide having more than one type of nucleoside. One preferred example of such a hybrid oligonucleotide comprises a ribonucleotide or 2'-substituted ribonucleotide region, and a deoxyribonucleotide region (see, e.g., Metelev and Agrawal, U.S. Pat. Nos. 5,652,355, 6,346,614 and 6,143,881).

For purposes of the invention, the term "immunostimulatory oligonucleotide" refers to an oligonucleotide as described above that induces an immune response when administered to a vertebrate, such as a fish, bird, or mammal. As used herein, the term "mammal" includes, without limitation rats, mice, cats, dogs, horses, cattle, cows, pigs, rabbits, non-human primates, and humans. Useful immunostimulatory oligonucleotides can be found described in Agrawal et al., WO 98/49288, published Nov. 5, 1998; WO 01/12804, published Feb. 22, 2001; WO 01/55370, published Aug. 2, 2001; PCT/US01/13682, filed Apr. 30, 2001; and PCT/US01/30137, filed Sep. 26, 2001. Preferably, the immunostimulatory oligonucleotide comprises at least one phosphodiester, phosphorothioate, methylphosphonate, or phosphordithioate internucleoside linkage.

In a further aspect, the invention provides a method for synergistically stimulating an immune response in a patient. The method comprises administering to a patient, a combination of a therapeutically effective synergistic amount of at least one immunomer compound or immunostimulatory oligonucleotide in accordance with the invention and a therapeutically effective synergistic amount of IL-2 (and/or an agent that induces IL-2 production in situ, such as a DNA vaccine or expression vector expressing IL-2), wherein administration of said combination synergistically stimulates the production of cytokines in a patient. Preferably, the cytokines that are synergistically stimulated in accordance with the invention are selected from the group consisting of, IL-12 and interferon-γ (IFN-γ), IFN-α, IFN-β or combinations thereof.

The term "effective synergistic amount" is used herein to denote known concentrations of immunomer compound or immunostimulatory oligonucleotide and of IL-2 administered for an effective period of time such that the combined stimulatory effect of the immunomer compound or immunostimulatory oligonucleotide and IL-2 are more than additive, i.e. the combined stimulatory effect is greater than the expected-total stimulatory effect calculated on the basis of the sum of the individual stimulatory effects.

As used herein, the term "cytokine" refers to any of many soluble molecules that cells of the immune system produce to control reactions between other cells. The term "cytokine" includes, for example, interleukins (e.g., IL-1, IL-2, IL-3, IL-6, IL-10, IL12, etc.), interferons (e.g., IFN-.alpha., IFN-.beta., IFN-.gamma.), chemokines, hematopoietic growth factors (e.g. erythropoietin), tumor necrosis factors, colony stimulating factors (e.g., G-CSF, M-CSF, GM-CSF) and transforming growth factors (TGF-alpha).

In accordance with the invention, an "immunomer" refers to any compound comprising at least two oligonucleotides linked directly at their 3' ends, or directly via internucleoside linkages, or directly at a functionalized nucleobase or sugar, or that are indirectly linked together via a non-nucleotidic linker, wherein at least one of the oligonucleotides, in the context of the immunomer compound, is an immunostimulatory oligonucleotide having an accessible 5' end. In the context of the invention, an immunostimulatory oligonucleotide is an oligonucleotide that comprises at least one of an immunostimulatory "CpG" dinucleotide, an immunostimulatory domain, or other immunostimulatory moiety. As used herein, the term "accessible 5' end" means that the 5' end of the oligonucleotide is sufficiently available such that the factors that recognize and bind to immunomer compounds and immunostimulatory oligonucleotides and stimulate the immune system have access to the 5' end.

In some embodiments, at least one immunostimulatory oligonucleotide of the immunomer compound comprises an immunostimulatory dinucleotide of formula 5'-Pyr-Pur-3', wherein Pyr is a natural or synthetic pyrimidine nucleoside and Pur is a natural or synthetic purine nucleoside. As used herein, the term "pyrimidine nucleoside" refers to a nucleoside wherein the base component of the nucleoside is a pyrimidine base. Similarly, the term "purine nucleoside" refers to a nucleoside wherein the base component of the nucleoside is a purine base. For purposes of the invention, a "synthetic" pyrimidine or purine nucleoside includes a non-naturally occurring pyrimidine or purine base, a non-naturally occurring sugar moiety, or a combination thereof.

Preferred pyrimidine nucleosides in the immunostimulatory oligonucleotides and/or immunomer compounds used in the method according to the invention have the structure (I):

wherein:
D is a hydrogen bond donor;
D' is selected from the group consisting of hydrogen, hydrogen bond donor, hydrogen bond acceptor, hydrophilic group, hydrophobic group, electron withdrawing group and electron donating group;
A is a hydrogen bond acceptor or a hydrophilic group;
A' is selected from the group consisting of hydrogen bond acceptor, hydrophilic group, hydrophobic group, electron withdrawing group and electron donating group;
X is carbon or nitrogen; and
S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH₂, —SH and —OH. Preferred hydrogen bond acceptors include, without limitation, C=O, C=S, and the ring nitrogen atoms of an aromatic heterocycle, e.g., N3 of cytosine.

In some embodiments, the base moiety in (I) is a non-naturally occurring pyrimidine base. Examples of preferred non-naturally occurring pyrimidine bases include, without limitation, 5-hydroxycytosine, 5-hydroxymethylcytosine, N4-alkylcytosine, preferably N4-ethylcytosine, and 4-thiouracil. In some embodiments, the sugar moiety S' in (I) is a non-naturally occurring sugar moiety. For purposes of the present invention, a "naturally occurring sugar moiety" is a sugar moiety that occurs naturally as part of nucleic acid, e.g., ribose and 2'-deoxyribose, and a "non-naturally occurring sugar moiety" is any sugar that does not occur naturally as part of a nucleic acid, but which can be used in the backbone for an oligonucleotide, e.g, hexose. Arabinose and arabinose derivatives are examples of preferred sugar moieties.

Preferred purine nucleoside analogs in immunostimulatory oligonucleotides and/or immunomer compounds used in the method according to the invention have the structure (II):

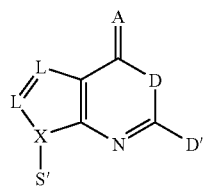

(II)

wherein:

D is a hydrogen bond donor;

D' is selected from the group consisting of hydrogen, hydrogen bond donor, and hydrophilic group;

A is a hydrogen bond acceptor or a hydrophilic group;

X is carbon or nitrogen;

each L is independently selected from the group consisting of C, O, N and S; and S' is a pentose or hexose sugar ring, or a non-naturally occurring sugar.

Preferably, the sugar ring is derivatized with a phosphate moiety, modified phosphate moiety, or other linker moiety suitable for linking the pyrimidine nucleoside to another nucleoside or nucleoside analog.

Preferred hydrogen bond donors include, without limitation, —NH—, —NH₂, —SH and —OH. Preferred hydrogen bond acceptors include, without limitation, C=O, C=S, —NO₂ and the ring nitrogen atoms of an aromatic heterocycle, e.g., N1 of guanine.

In some embodiments, the base moiety in (II) is a non-naturally occurring purine base. Examples of preferred non-naturally occurring purine bases include, without limitation, 6-thioguanine and 7-deazaguanine. In some embodiments, the sugar moiety S' in (II) is a naturally occurring sugar moiety, as described above for structure (I).

In preferred embodiments, the immunostimulatory dinucleotide in the immunostimulatory oligonucleotides and/or immunomer compound used in the method according to the invention is selected from the group consisting of CpG, C*pG, CpG*, and C*pG*, wherein C is cytidine or 2'-deoxycytidine, C* is 2'-deoxythymidine, arabinocytidine, 2'-deoxythymidine, 2'-deoxy-2'-substitutedarabinocytidine, 2'-O-substitutedarabinocytidine, 2'-deoxy-5-hydroxycytidine, 2'-deoxy-N4-alkyl-cytidine, 2'-deoxy-4-thiouridine, other non-natural pyrimidine nucleosides, or 1-(2'-deoxy-β-D-ribofuranosyl)-2-oxo-7-deaza-8-methyl-purine; G is guanosine or 2'-deoxyguanosine, G* is 2' deoxy-7-deazaguanosine, 2'-deoxy-6-thioguanosine, arabinoguanosine, 2'-deoxy-2' substituted-arabinoguanosine, 2'-O-substituted-arabinoguanosine, 2'-deoxyinosine, or other non-natural purine nucleoside, and p is an internucleoside linkage selected from the group consisting of phosphodiester, phosphorothioate, and phosphorodithioate. In certain preferred embodiments, the immunostimulatory dinucleotide is not CpG.

The immunostimulatory oligonucleotides may include immunostimulatory moieties on one or both sides of the immunostimulatory dinucleotide. Thus, in some embodiments, the immunostimulatory oligonucleotide comprises an immunostimulatory domain of structure (III):

$$5'-Nn-N1-Y-Z-N1-Nn-3' \qquad (III)$$

wherein:

Y is cytidine, 2'deoxythymidine, 2' deoxycytidine arabinocytidine, 2'-deoxy-2'-substitutedarabinocytidine, 2'-deoxythymidine, 2'-O-substitutedarabinocytidine, 2'-deoxy-5-hydroxycytidine, 2'-deoxy-N4-alkyl-cytidine, 2'-deoxy-4-thiouridine, other non-natural pyrimidine nucleosides, or 1-(2'-deoxy-β-D-ribofuranosyl)-2-oxo-7-deaza-8-methyl-purine;

Z is guanosine or 2'-deoxyguanosine, 2' deoxy-7-deazaguanosine, 2'-deoxy-6-thioguanosine, arabinoguanosine, 2'-deoxy-2'substituted-arabinoguanosine, 2'-O-substituted-arabinoguanosine, 2'deoxyinosine, or other non-natural purine nucleoside;

N1, at each occurrence, is preferably a naturally occurring or a synthetic nucleoside or an immunostimulatory moiety selected from the group consisting of abasic nucleosides, arabinonucleosides, 2'-deoxyuridine, a-deoxyribonucleosides, P-L-deoxyribonucleosides, and nucleosides linked by a phosphodiester or modified internucleoside linkage to the adjacent nucleoside on the 3' side, the modified internucleotide linkage being selected from, without limitation, a linker having a length of from about 2 angstroms to about 200 angstroms, C2-C18 alkyl linker, poly(ethylene glycol) linker, 2-aminobutyl-1,3-propanediol linker, glyceryl linker, 2'-5' internucleoside linkage, and phosphorothioate, phosphorodithioate, or methylphosphonate internucleoside linkage;

Nn, at each occurrence, is preferably a naturally occurring nucleoside or an immunostimulatory moiety selected from the group consisting of abasic nucleosides, arabinonucleosides, 2'-deoxyuridine, α-deoxyribonucleosides, 2'-O-substituted ribonucleosides, and nucleosides linked by a modified internucleoside linkage to the adjacent nucleoside on the 3' side, the modified internucleoside linkage preferably being selected from the group consisting of amino linker, C2-C18 alkyl linker, poly(ethylene glycol) linker, 2-aminobutyl-1,3-propanediol linker, glyceryl linker, 2'-5' internucleoside linkage, and methylphosphonate internucleoside linkage;

provided that at least one N1 or Nn is an immunostimulatory moiety;

wherein each n is independently a number from 0 to 30; and wherein, in the case of an immunomer compound, the 3'end is linked directly or via a non-nucleotidic linker to another oligonucleotide, which may or may not be immunostimulatory.

In some preferred embodiments, YZ is arabinocytidine or 2'-deoxy-2'-substituted arabinocytidine and arabinoguanosine or 2'deoxy-2'-substituted arabinoguanosine. Preferred immunostimulatory moieties include modifications in the phosphate backbones, including, without limitation, methylphosphonates, methylphosphonothioates, phosphotriesters, phosphothiotriesters, phosphorothioates, phosphorodithioates, triester prodrugs, sulfones, sulfonamides, sulfamates, formacetal, N-methylhydroxylamine, carbonate, carbamate, morpholino, boranophosphonate, phosphoramidates, especially primary amino-phosphoramidates, N3 phosphoramidates and N5 phosphoramidates, and stereospecific linkages (e.g., $(R_P)$- or $(S_P)$-phosphorothioate, alkylphosphonate, or phosphotriester linkages).

Preferred immunostimulatory moieties according to the invention further include nucleosides having sugar modifications, including, without limitation, 2'-substituted pentose sugars including, without limitation, 2'-O-methylribose, 2'-O-methoxyethylribose, 2'-O-propargylribose, and 2'-deoxy-2'-fluororibose; 3'-substituted pentose sugars, including, without limitation, 3'-O-methylribose; 1',2'-dideoxyribose; arabinose; substituted arabinose sugars, including, without limitation, 1'-methylarabinose, 3'-hydroxymethylarabinose, 4'-hydroxymethyl-arabinose, and 2'-substituted arabinose sugars; hexose sugars, including, without limitation, 1,5-anhydrohexitol; and alpha-anomers. In embodiments in which the modified sugar is a 3'-deoxyribonucleoside or a 3'-O-substituted ribonucleoside, the immunostimulatory moiety is attached to the adjacent nucleoside by way of a 2'-5' internucleoside linkage.

Preferred immunostimulatory moieties in immunostimulatory oligonucleotides and/or immunomer compounds used in the method according to the invention further include oligonucleotides having other carbohydrate backbone modifications and replacements, including peptide nucleic acids (PNA), peptide nucleic acids with phosphate groups (PHONA), locked nucleic acids (LNA), morpholino backbone oligonucleotides, and oligonucleotides having backbone linker sections having a length of from about 2 angstroms to about 200 angstroms, including without limitation, alkyl linkers or amino linkers. The alkyl linker may be branched or unbranched, substituted or unsubstituted, and chirally pure or a racemic mixture. Most preferably, such alkyl linkers have from about 2 to about 18 carbon atoms. In some preferred embodiments such alkyl linkers have from about 3 to about 9 carbon atoms. Some alkyl linkers include one or more functional groups selected from the group consisting of hydroxy, amino, thiol, thioether, ether, amide, thioamide, ester, urea, and thioether. Some such functionalized alkyl linkers are poly(ethylene glycol) linkers of formula —O—($CH_2$—$CH_2$—O—)$_n$ (n=1-9). Some other functionalized alkyl linkers are peptides or amino acids.

Preferred immunostimulatory moieties in immunostimulatory oligonucleotides and/or immunomer compounds used in the method according to the invention further include DNA isoforms, including, without limitation, β-L-deoxyribonucleosides and α-deoxyribonucleosides. Preferred immunostimulatory moieties incorporate 3' modifications, and further include nucleosides having unnatural internucleoside linkage positions, including, without limitation, 2'-5', 2'-2', 3'-3' and 5'-5' linkages.

Preferred immunostimulatory moieties in immunostimulatory oligonucleotides and/or immunomer compounds used in the method according to the invention further include nucleosides having modified heterocyclic bases, including, without limitation, 5-hydroxycytosine, 5-hydroxymethylcytosine, N4-alkylcytosine, preferably N4-ethylcytosine, 4-thiouracil, 6-thioguanine, 7-deazaguanine, inosine, nitropyrrole, C5-propynylpyrimidine, and diaminopurines, including, without limitation, 2,6-diaminopurine.

By way of specific illustration and not by way of limitation, for example, in the immunostimulatory domain of structure (III), a methylphosphonate internucleoside linkage at position Ni or Nn is an immunostimulatory moiety, a linker having a length of from about 2 angstroms to about 200 angstroms, C2-C18 alkyl linker at position X1 is an immunostimulatory moiety, and a β-L-deoxyribonucleoside at position X1 is an immunostimulatory moiety. See Table 1 below for representative positions and structures of immunostimulatory moieties. It is to be understood that reference to a linker as the immunostimulatory moiety at a specified position means that the nucleoside residue at that position is substituted at its 3'-hydroxyl with the indicated linker, thereby creating a modified internucleoside linkage between that nucleoside residue and the adjacent nucleoside on the 3' side. Similarly, reference to a modified internucleoside linkage as the-immunostimulatory moiety at a specified position means that the nucleoside residue at that position is linked to the adjacent nucleoside on the 3' side by way of the recited linkage.

TABLE 1

| Position | TYPICAL IMMUNOSTIMULATORY MOIETIES |
|---|---|
| N1 | Naturally-occurring nucleosides, abasic nucleoside, arabinonucleoside, 2'-deoxyuridine, β-L-deoxyribonucleoside C2-C18 alkyl linker, poly(ethylene glycol) linkage, 2-aminobutyl-1,3-propanediol linker (amino linker), 2'-5' internucleoside linkage, methylphosphonate internucleoside linkage |
| Nn | Naturally-occurring nucleosides, abasic nucleoside, arabinonucleosides, 2'-deoxyuridine, 2'-O-substituted ribonucleoside, 2'-5' internucleoside linkage, methylphosphonate internucleoside linkage, provided that N1 and N2 cannot both be abasic linkages |

Table 2 shows representative positions and structures of immunostimulatory moieties within an immunostimulatory oligonucleotide having an upstream potentiation domain. As used herein, the term "Spacer 9" refers to a poly(ethylene glycol) linker of formula —O—($CH_2CH_2$—O—)$_n$—, wherein n is 3. The term "Spacer 18" refers to a poly(ethylene glycol) linker of formula —O—($CH_2CH_2$—O)$_n$—, wherein n is 6. As used herein, the term "C2-C18 alkyl linker refers to a linker of formula —O—($CH_2$)$_q$—O—, where q is an integer from 2 to 18. Accordingly, the terms "C3-linker" and "C3-alkyl linker" refer to a linker of formula —O—($CH_2$)$_3$—O—. For each of Spacer 9, Spacer 18, and C2-C18 alkyl linker, the linker is connected to the adjacent nucleosides by way of phosphodiester, phosphorothioate, phosphorodithioate or methylphosphonate linkages.

TABLE 2

| Position | TYPICAL IMMUNOSTIMULATORY MOIETY |
|---|---|
| 5' N2 | Naturally-occurring nucleosides, 2-aminobutyl-1,3-propanediol linker |
| 5' N1 | Naturally-occurring nucleosides, β-L-deoxyribonucleoside, C2-C18 alkyl linker, poly(ethylene glycol), abasic linker, 2-aminobutyl-1,3-propanediol linker |
| 3' N1 | Naturally-occurring nucleosides, 1',2'-dideoxyribose, 2'-O-methyl-ribonucleoside, C2-C18 alkyl linker, Spacer 9, Spacer 18 |

TABLE 2-continued

| Position | TYPICAL IMMUNOSTIMULATORY MOIETY |
|---|---|
| 3' N2 | Naturally-occurring nucleosides, 1',2'-dideoxyribose, 3'-deoxyribonucleoside, β-L-deoxyribonucleoside, 2'-O-propargyl-ribonucleoside, C2-C18 alkyl linker, Spacer 9, Spacer 18, methylphosphonate internucleoside linkage |
| 3' N3 | Naturally-occurring nucleosides, 1',2'-dideoxyribose, C2-C18 alkyl linker, Spacer 9, Spacer 18, methylphosphonate internucleoside linkage, 2'-5' internucleoside linkage, d(G)n, polyI-polydC |
| 3' N2 + 3' N3 | 1',2'-dideoxyribose, β-L-deoxyribonucleoside, C2-C18 alkyl linker, d(G)n, polyI-polydC |
| 3' N3 + 3' N4 | 2'-O-methoxyethyl-ribonucleoside, methylphosphonate internucleoside linkage, d(G)n, polyI-polydC |
| 3' N5 + 3' N6 | 1',2'-dideoxyribose, C2-C18 alkyl linker, d(G)n, polyI-polydC |
| 5' N1 + 3' N3 | 1',2'-dideoxyribose, d(G)n, polyI-polydC |

Table 3 shows representative positions and structures of immunostimulatory moieties within an immunostimulatory oligonucleotide having a downstream potentiation domain.

TABLE 3

| Position | TYPICAL IMMUNOSTIMULATORY MOIETY |
|---|---|
| 5' N2 | methylphosphonate internucleoside linkage |
| 5' N1 | methylphosphonate internucleoside linkage |
| 3' N1 | 1',2'-dideoxyribose, methylphosphonate internucleoside linkage, 2'-O-methyl |
| 3' N2 | 1',2'-dideoxyribose, β-L-deoxyribonucleoside, C2-C18 alkyl linker, Spacer 9, Spacer 18, 2-aminobutyl-1,3-propanediol linker, methylphosphonate internucleoside linkage, 2'-O-methyl |
| 3' N3 | 3'-deoxyribonucleoside, 3'-O-substituted ribonucleoside, 2'-O-propargyl-ribonucleoside |
| 3' N2 + 3' N3 | 1',2'-dideoxyribose, β-L-deoxyribonucleoside |

The immunomer compounds used in the method according to the invention comprise at least two oligonucleotides linked directly or via a non-nucleotidic linker. For purposes of the invention, a "non-nucleotidic linker" is any moiety that can be linked to the oligonucleotides by way of covalent or non-covalent linkages. Preferably such linker is from about 2 angstroms to about 200 angstroms in length. Several examples of preferred linkers are set forth below. Non-covalent linkages include, but are not limited to, electrostatic interaction, hydrophobic interactions, π-stacking interactions, and hydrogen bonding. The term "non-nucleotidic linker" is not meant to refer to an internucleoside linkage, as described above, e.g., a phosphodiester, phosphorothioate, or phosphorodithioate functional group, that directly connects the 3'-hydroxyl groups of two nucleosides. For purposes of this invention, such a direct 3'-3' linkage is considered to be a "nucleotidic linkage."

In some embodiments, the non-nucleotidic linker is a metal, including, without limitation, gold particles. In some other embodiments, the non-nucleotidic linker is a soluble or insoluble biodegradable polymer bead.

In yet other embodiments, the non-nucleotidic linker is an organic moiety having functional groups that permit attachment to the oligonucleotide. Such attachment preferably is by any stable covalent linkage.

In some embodiments, the non-nucleotidic linker is a biomolecule, including, without limitation, polypeptides, antibodies, lipids, antigens, allergens, and oligosaccharides. In some other embodiments, the non-nucleotidic linker is a small molecule. For purposes of the invention, a small molecule is an organic moiety having a molecular weight of less than 1,000 Da. In some embodiments, the small molecule has a molecular weight of less than 750 Da.

In some embodiments, the small molecule is an aliphatic or aromatic hydrocarbon, either of which optionally can include, either in the linear chain connecting the oligonucleotides or appended to it, one or more functional groups selected from the group consisting of hydroxy, amino, thiol, thioether, ether, amide, thioamide, ester, urea, and thiourea. The small molecule can be cyclic or acyclic. Examples of small molecule linkers include, but are not limited to, amino acids, carbohydrates, cyclodextrins, adamantane, cholesterol, haptens and antibiotics. However, for purposes of describing the non-nucleotidic linker, the term "small molecule" is not intended to include a nucleoside.

In some embodiments, the small molecule linker is glycerol or a glycerol homolog of the formula HO—$(CH_2)_o$—CH(OH)—$(CH_2)_p$—OH, wherein o and p independently are integers from 1 to about 6, from 1 to about 4, or from 1 to about 3. In some other embodiments, the small molecule linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6, or from 2 to about 4.

Some non-nucleotidic linkers in immunomer compounds used in the method according to the invention permit attachment of more than two oligonucleotides, as schematically depicted in FIG. 1. For example, the small molecule linker glycerol has three hydroxyl groups to which oligonucleotides may be covalently attached. Some immunomer compounds according to the invention, therefore, comprise more than two oligonucleotides linked at their 3' ends to a non-nucleotidic linker. Some such immunomer compounds comprise at least two immunostimulatory oligonucleotides, each having an accessible 5' end.

Figure 5:
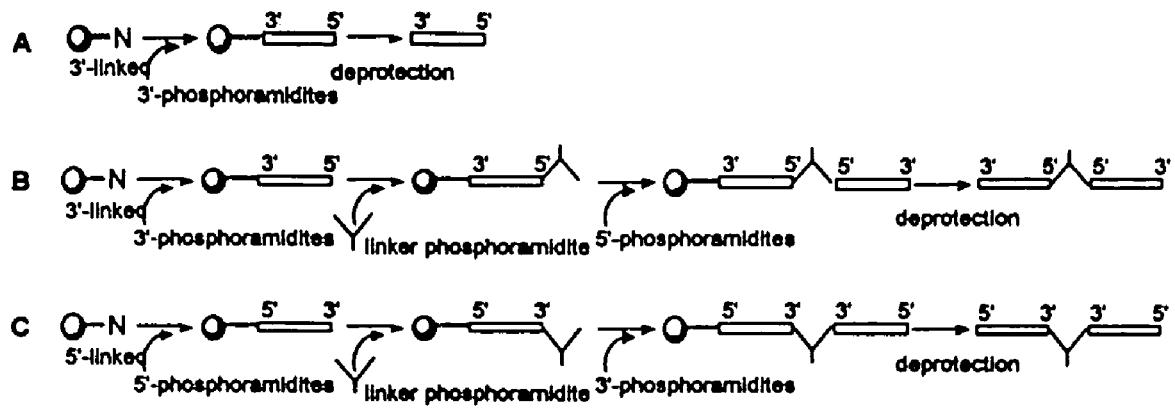
FIG. 5 is a synthetic scheme for the linear synthesis of immunomer compounds of the invention. DMTr=4,4'-dimethoxytrityl; CE=cyanoethyl.
Figure 5:
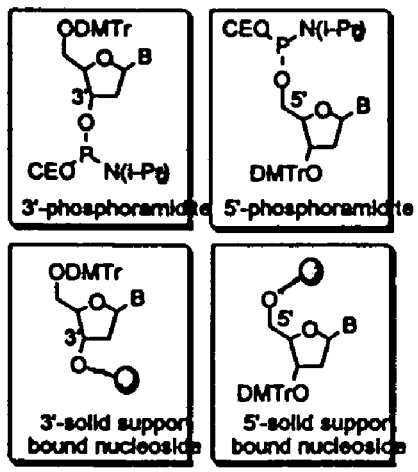
Figure 6:
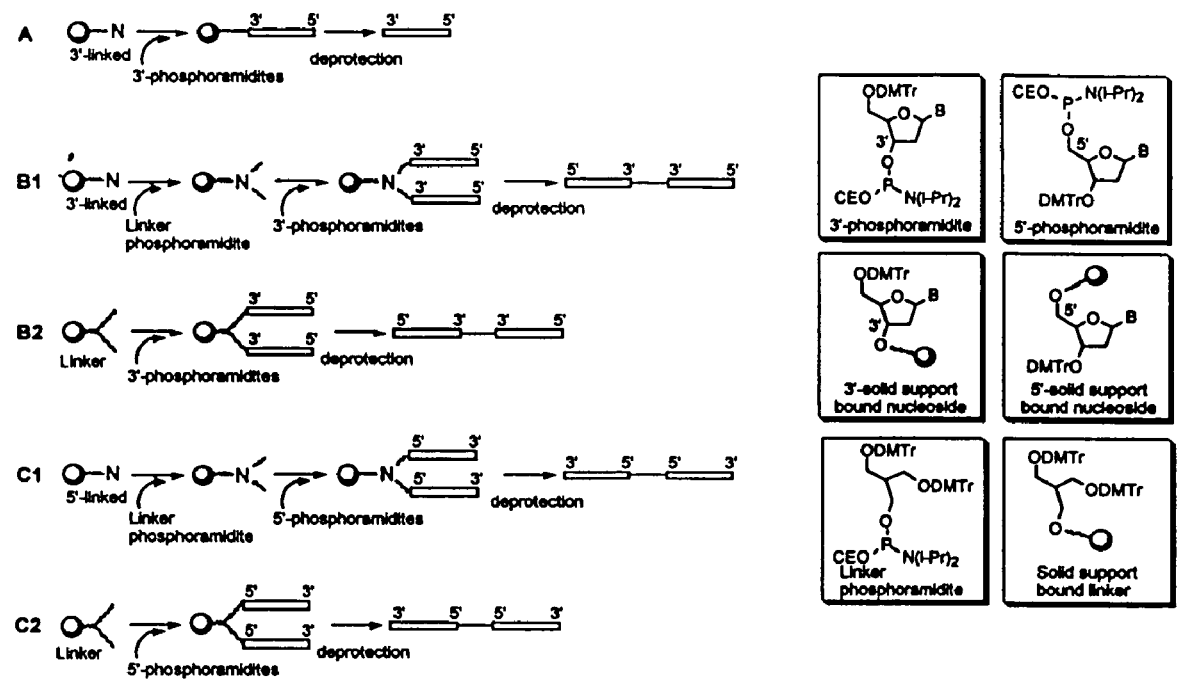
FIG. 6 is a synthetic scheme for the parallel synthesis of immunomer compounds of the invention. DMTr=4,4'-dimethoxytrityl; CE=cyanoethyl.

The immunostimulatory oligonucleotides and/or immunomer compounds used in the method according to the invention may conveniently be synthesized using an automated synthesizer and phosphoramidite approach as schematically depicted in FIGS. 5 and 6, and further described in the Examples. In some embodiments, the immunostimulatory oligonucleotides and/or immunomer compounds are synthesized by a linear synthesis approach (see FIG. 5). As used herein, the term "linear synthesis" refers to a synthesis that starts at one end of the immunomer compound and progresses linearly to the other end. Linear synthesis permits incorporation of either identical or un-identical (in terms of length, base composition and/or chemical modifications incorporated) monomeric units into the immunostimulatory oligonucleotides and/or immunomer compounds.

An alternative mode of synthesis for immunomer compounds is "parallel synthesis", in which synthesis proceeds outward from a central linker moiety (see FIG. 6). A solid support attached linker can be used for parallel synthesis, as is described in U.S. Pat. No. 5,912,332. Alternatively, a universal solid support, such as phosphate attached to controlled pore glass support, can be used.

Parallel synthesis of immunomer compounds has several advantages over linear synthesis: (1) parallel synthesis permits the incorporation of identical monomeric units; (2) unlike in linear synthesis, both (or all) the monomeric units are synthesized at the same time, thereby the number of synthetic steps and the time required for the synthesis is the same as that of a monomeric unit; and (3) the reduction in synthetic steps improves purity and yield of the final immunomer product.

At the end of the synthesis by either linear synthesis or parallel synthesis protocols, the immunostimulatory oligonucleotides or immunomer compounds used in the method according to the invention may conveniently be deprotected with concentrated ammonia solution or as recommended by the phosphoramidite supplier, if a modified nucleoside is incorporated. The product immunostimulatory oligonucleotides and/or immunomer compound is preferably purified by reversed phase HPLC, detritylated, desalted and dialyzed.

Immunostimulatory oligonucleotides suitable for use as a component of an immunomer compound, or in accordance with the fourth aspect of the invention, are described in the following U.S. patents and pending U.S. patent applications and are incorporated herein by reference: U.S. Pat. Nos. 6,426,334 and 6,476,000; and U.S. patent application Ser. Nos. 09/770,602, 09/845,623, 09/965,116, 60/440,587, 10/361,111, 60/471,247, 60/477. Preferred immunostimulatory oligonucleotides and immunomer compounds of the invention are described in pending U.S. patent application Ser. No. 10/279,684. Table 4 shows representative immunomer compounds used in the method according to the invention. Additional immunomer compounds are found described in the Examples and in U.S. patent application Ser. No. 10/279,684.

TABLE 4

Examples of Immunomer Sequences

| Oligo or Immunomer No. | Sequences and Modification (5'-3') |
|---|---|
| 1 | 5'-GAGAACGCTCGACCTT-3' (SEQ ID NO: 1) |
| 2 | 5'-GAGAACGCTCGACCTT-3'-3'-TTCCAGCTCGCAAGAG-5' (SEQ ID NO: 2) |
| 3 | 3'-TTCCAGCTCGCAAGAG-5'-5'-GAGAACGCTCGACCTT-3' (SEQ ID NO: 3) |
| 4 | 5'-CTATCTGACGTTCTCTGT-3' (SEQ ID NO: 4) |
| 5 | 5'-T-3' branched to two HNCO—$C_4H_8$-5'-CTATLTGACGTTCTCTGT-3' (SEQ ID NOS 39 and 5) |
| 6 | 5'-CTATLTGACGTTCTCTGT-3'-$C_4H_8$—CONH— and 5'-CTATLTGACGTTCTCTGT-3'-$C_4H_8$—CONH— joined to 3'-C-5' (SEQ ID NOS 39 and 6) |
| 7 | 5'-CTATCTGACGTTCTCTGT-3'-$C_4H_8$—CONH— and 5'-CTATCTGACGTTCTCTGT-3'-$C_4H_8$—CONH— joined to 3'-C-5' (SEQ ID NO: 7) |
| 8 | 5'-CTATCTGACGTTCTCTGT-3' and 5'-CTATCTGACGTTCTCTGT-3' joined to 3'-C-5' (SEQ ID NO: 8) |
| 9 | 5'-CTATCTGAYGTTCTCTGT-3' and 5'-CTATCTGAYGTTCTCTGT-3' joined to 3'-C-5' (SEQ ID NO: 9) |
| 10 | 5'-CTATCTGACRTTCTCTGT-3' and 5'-CTATCTGACRTTCTCTGT-3' joined to 3'-C-5' (SEQ ID NO: 10) |

TABLE 4-continued

Examples of Immunomer Sequences

| Oligo or Immunomer No. | Sequences and Modification (5'-3') |
|---|---|
| 11 | 5'-CTALCTGAYGTTCTCTGT-3'⎯⎤<br>⎯⎯⎯⎯⎯⎯⎯⎯⎯⎯⎯⎯⎯⎯⎯⎯⎯⎯⎯├─3'-C-5'<br>5'-CTALCTGAYGTTCTCTGT-3'⎯⎦<br>(SEQ ID NOS 40 and 11) |
| 12 | 5'-CTALCTGACRTTCTCTGT-3'⎯⎤<br>⎯⎯⎯⎯⎯⎯⎯⎯⎯⎯⎯⎯⎯⎯⎯⎯⎯⎯⎯├─3'-C-5'<br>5'-CTALCTGACRTTCTCTGT-3'⎯⎦<br>(SEQ ID NOS 40 and 12) |
| 13 | 5'-CTGACGTTCTCTGT-3'<br>(SEQ ID NO: 13) |
| 14 | 5'-CTGACGTTCTCTGT-3'⎯⎤<br>⎯⎯⎯⎯⎯⎯⎯⎯⎯⎯⎯⎯⎯⎯⎯├─3'-C-5'<br>5'-CTGACGTTCTCTGT-3'⎯⎦<br>(SEQ ID NO: 14) |
| 15 | 5'-CTGAYGTTCTCTGT-3'⎯⎤<br>⎯⎯⎯⎯⎯⎯⎯⎯⎯⎯⎯⎯⎯⎯⎯├─3'-C-5'<br>5'-CTGAYGTTCTCTGT-3'⎯⎦<br>(SEQ ID NO: 15) |
| 16 | 5'-CTGACRTTCTCTGT-3'⎯⎤<br>⎯⎯⎯⎯⎯⎯⎯⎯⎯⎯⎯⎯⎯⎯⎯├─3'-C-5'<br>5'-CTGACRTTCTCTGT-3'⎯⎦<br>(SEQ ID NO: 16) |
| 17 | 5'-XXTGACGTTCTCTGT-3'<br>(SEQ ID NO: 17) |
| 18 | 5'-XXXTGACGTTCTCTGT-3'⎯⎤<br>⎯⎯⎯⎯⎯⎯⎯⎯⎯⎯⎯⎯⎯⎯⎯⎯⎯├─3'-C-5'<br>5'-XXXTGACGTTCTCTGT-3'⎯⎦<br>(SEQ ID NO: 18) |
| 19 | 5'-XXXTGAYGTTCTCTGT-3'⎯⎤<br>⎯⎯⎯⎯⎯⎯⎯⎯⎯⎯⎯⎯⎯⎯⎯⎯⎯├─3'-C-5'<br>5'-XXXTGAYGTTCTCTGT-3'⎯⎦<br>(SEQ ID NO: 19) |
| 20 | 5'-XXXTGACRTTCTCTGT-3'⎯⎤<br>⎯⎯⎯⎯⎯⎯⎯⎯⎯⎯⎯⎯⎯⎯⎯⎯⎯├─3'-C-5'<br>5'-XXXTGACRTTCTCTGT-3'⎯⎦<br>(SEQ ID NO: 20) |
| 21 | 5'-TCTGACGTTCT-3'<br>(SEQ ID NO: 21) |
| 22 | 5'-XXXTCTGACGTTCT-3'⎯⎤<br>⎯⎯⎯⎯⎯⎯⎯⎯⎯⎯⎯⎯⎯⎯⎯├─3'-C-5'<br>5'-XXXTCTGACGTTCT-3'⎯⎦<br>(SEQ ID NO: 22) |

TABLE 4-continued

Examples of Immunomer Sequences

| Oligo or Immunomer No. | Sequences and Modification (5'-3') |
|---|---|
| 23 | 5'-XXXTCTGAYGTTCT-3'⎤<br>　　　　　　　　　　　　　├─3'-C-5'<br>5'-XXXTCTGAYGTTCT-3'⎦<br>(SEQ ID NO: 23) |
| 24 | 5'-XXXTCTGACRTTCT-3'⎤<br>　　　　　　　　　　　　　├─3'-C-5'<br>5'-XXXTCTGACRTTCT-3'⎦<br>(SEQ ID NO: 24) |
| 191 | 5'-CTGTCRTTCTC-X₁-CTCTTRCTGTC-5'<br>(SEQ ID NO: 41) |
| 192 | 5'-TCRTCRTTG-X₁-GTTRCTRCT-5'<br>(SEQ ID NO: 42) |
| 193 | 5'-TCRTCRTTCTG-X₁-GTCTTRCTRCT-5'<br>(SEQ ID NO: 43) |
| 194 | 5'-TCGTTG-Y₁-X₂-Y₁-GTTGCT-5'<br>(SEQ ID NO: 44) |
| 195 | 5'-TCGTT-Y₁-X₂-Y₁-TTGCT-5'<br>(SEQ ID NO: 45) |

```
   ┌─NHCOC₄H₈⁻
───┤                = Symmetric longer branches;
   └─NHCOC₄H₈⁻

┌─
───┤                = Symmetric glycerol (short) branches
   └─
```

L = C3-alkyl linker;
X = 1',2'-dideoxyriboside;
Y = $^{5OH}$dC; R = 7-deaza-dG
R = arabinoguanosine;
X₁ = glycerol linker;

A further aspect of the invention provides an immunostimulatory nucleic acid comprising at least two oligonucleotides, wherein the immunostimulatory nucleic acid has a secondary structure. In certain embodiments, the immunostimulatory nucleic acid has a 3'-end stem loop secondary structure by way of hydrogen bonding with a complementary sequence. In certain embodiments the nucleic acid that has reduced immunostimulatory activity forms a 5'-end stem loop secondary structure by way of hydrogen bonding with a complementary sequence. In this aspect, immunostimulatory nucleic acid comprises a structure as detailed in formula (I).

Domain A-Domain B-Domain C　　　　　　　　　(I)

Domains may be from about 2 to about 12 nucleotides in length. Domain A may be 5'-3' or 3'-5' or 2'-5' DNA, RNA, RNA-DNA, DNA-RNA having or not having a palindromic or self-complementary domain containing or not containing at least one dinucleotide selected from the group consisting of CpG, C*pG, C*pG* and CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2'-dideoxy-5-halocytosine, 2'-deoxy-5-nitrocytosine, arabinocytidine, 2'-deoxy-2'-substitutedarabinocytidine, 2'-O-substituted arabinocytidine, 2'-deoxy-5-hydroxycytidine, 2'-deoxy-N4-alkyl-cytidine, 2'-deoxy-4-thiouridine, or other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate. In certain preferred embodiments, the immunostimulatory dinucleotide is not CpG.

In certain embodiments, Domain A will have more than one dinucleotide selected from the group consisting of CpG, C*pG, C*pG* and CpG*.

Domain B, as depicted by an "X" below, is a linker joining Domains A and C that may be a 3'-'5' linkage, a 2'-5' linkage, a 3'-3' linkage, a phosphate group, a nucleoside, or a non-nucleoside linker that may be aliphatic, aromatic, aryl, cyclic, chiral, achiral, a peptide, a carbohydrate, a lipid, a fatty acid, mono- tri- or hexapolyethylene glycol, or a heterocyclic moiety.

Domain C may be 5'-3' or 3'-5', 2'-5' DNA, RNA, RNA-DNA, DNA-RNA Poly I-Poly C having or not having a palindromic or self-complementary sequence, which can or cannot have a dinucleotide selected from the group consisting of CpG, C*pG, C*pG*, CpG*, wherein C is cytidine or 2'-deoxycytidine, G is guanosine or 2'-deoxyguanosine, C* is 2'-deoxythymidine, 1-(2'-deoxy-β-D-ribofuranosyl)-2-oxo-7-deaza-8-methyl-purine, 2' dideoxy-5-halocytosine, 2'-deoxy-5-halocytosine, arabinocytidine, 2'-deoxy-2'-substituted arabinocytidine, 2'-O-substituted arabinocytidine, 2'-deoxy-5-hydroxycytidine, 2'-deoxy-N4-alkyl-cytidine, 2'-deoxy-4-thiouridine, other pyrimidine nucleoside analogs, G* is 2'-deoxy-7-deazaguanosine, 2'-deoxy-6-thioguanosine, arabinoguanosine, 2'-deoxy-2'substituted-arabinoguanosine, 2'-O-substituted-arabinoguanosine, 2'-deoxyinosine, or other purine nucleoside analogs, and p is an internucleoside linkage selected from the group consisting of phosphodiester, phosphorothioate, and phosphorodithioate. In certain preferred embodiments, the immunostimulatory dinucleotide is not CpG. In some embodiments, Domain B is preferably a non-nucloetidic linker connecting oligonucleotides of Domain A and Domain C, which are referred to as "immunomers." In certain preferred embodiments, Domain C does not have the dinucleotide CpG, C*pG, C*pG* or CpG*.

By way of non-limiting example, in certain embodiments of this aspect the immunostimulatory nucleic acid will have a structure as detailed in formula (II).

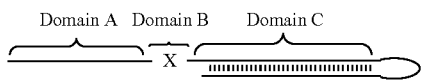
(II)

As one skilled in the art would recognize, there is a secondary structure element in the terminal end of the molecule in the form of an intramolecular stem-loop.

By way of non-limiting example, in certain embodiments of this aspect the immunostimulatory nucleic acid will have a structure as detailed in formula (III)

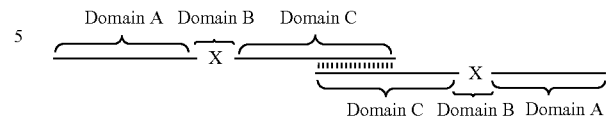
(III)

The structure depicted in formula (III) is referred to herein as a "terminal dimmer," since the ends of the two molecules are blocked because the sequences of the two ends are complementary allowing for intermolecular hydrogen bonding. In addition, domains A and A' may or may not be identical, domains B and B' may or may not be identical and domains C and C' may or may not be identical.

By way of non-limiting example, in certain embodiments of this aspect the immunostimulatory nucleic acid will have a structure as detailed in formula (IV).

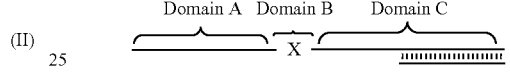
(IV)

As would be recognized by one skilled in the art, the terminal end of the depicted molecule has a secondary structure because the complementary sequence of its end is hydrogen bonded to this region. In certain embodiments, a molecule such as a ligand may be attached to the terminal end in order to facilitate cellular uptake or improve stability of the molecule.

Non-limiting examples of some nucleic acid molecules of the invention are presented in Table 5.

TABLE 5

| SEQ ID NO: | Sequence* | Structure |
|---|---|---|
| 91 | 5'-CTGTCTGACGTTCTCTG-3' | 5'━━━━━━3' |
| 92 | 5'-CTGTCTGACGTTCTCTG-GAA-CAGAG-3' | 5'━━━━━━◠<br>3'━━━━━━◡ |
| 93 | 5'-CTGTCTGACGTTCTCTG-GAA-CAGAGAACGTC-3' | 5'━━━━━━◠<br>3'━━━━━━◡ |
| 94 | 5'-CTGTCTGACGTTCTCTG-GAA-CAGAGAACGTCAGACAG-3' | 5'━━━━━━◠<br>3'━━━━━━◡ |
| 95 | 5'-GACAG-GAA-CTGTCTGACGTTCTCTG-3' | ◠━━━━━━3'<br>◡━━━━━━5' |

TABLE 5-continued

| SEQ ID NO: | Sequence* | Structure |
|---|---|---|
| 96 | 5'-AACGTCAGACAG-GAA-CTGTCTGACGTTCTCTG-3' | 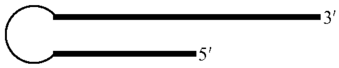 |
| 97 | 5'-CAGAGAACGTCAGACAG-GAA-CTGTCTGACGTTCTCTG-3' | 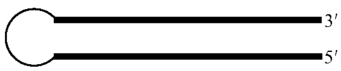 |
| 98 | 5'-CTATCTGACGTTCTCTGT-3' | 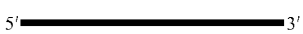 |
| 99 | 5'-CTATCTGACGTTCTCTGT-gtgatcac-3' | 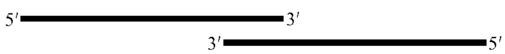 |
| 100 | 5'-gtgatcac-CTATCTGACGTTCTCTGT-3' | 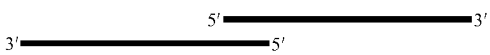 |
| 101 | 5'-CTGTCTGTCGTTCTCTG-3' | 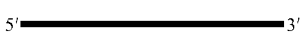 |
| 102 | 5'-CTGTCTGTCGTTCTCTG-GAA-CAGAG-3' | 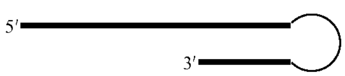 |
| 103 | 5'-CTGTCTGTCGTTCTCTG-GAA-CAGAGAACGAC-3' | 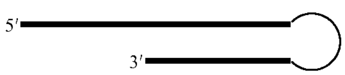 |
| 104 | 5'-CTGTCTGTCGTTCTCTG-GAA-CAGAGAACGACAGACAG-3' | 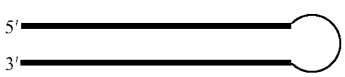 |
| 105 | 5'-GACAG-GAA-CTGTCTGTCGTTCTCTG-3' | 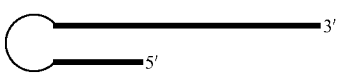 |
| 106 | 5'-AACGACAGACAG-GAA-CTGTCTGACGTTCTCTG-3' | 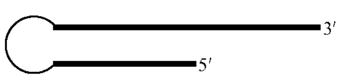 |
| 107 | 5'-CAGAGAACGACAGACAG-GAA-CTGTCTGTCGTTCTCTG-3' | 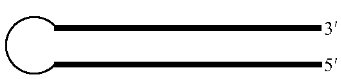 |
| 108 | 5'-TCGTCGTT-GAGCTCT-GAA-AGAGCTC-3' | 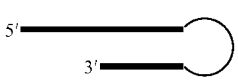 |
| 109 | 5'-TCGTCGTT-GTGAGCTCTGT-GAA-ACAGAGCTCAC-3' | 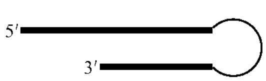 |
| 110 | 5'-TCGTCGTT-GCACAGAGCTCTGCT-GAA-AGCAGAGCTCTGTGC-3' | 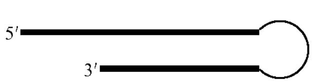 |

TABLE 5-continued

| SEQ ID NO: | Sequence* | Structure |
|---|---|---|
| 111 | 5'-TCGTCGTT-GCTGACAGAGCTCTGCTAT-GAA-ATAGCAGAGCTCTGTCAGC-3' | 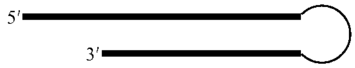 |
| 112 | 5'-TCGTCGTT-GTGCTCT-GAA-CTTGCTC-3' | 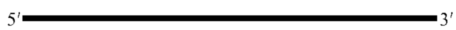 |
| 113 | 5'-TCGTCGTT-GTGTGCTCTGT-GAA-CATCAGTCTAC-3' | 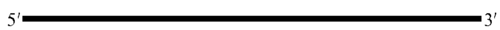 |
| 114 | 5'-TCGTCGTT-gagctct-GAA-agagctc-3' | 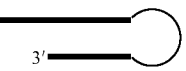 |
| 115 | 5'-TCGTCGTT-gtgagctctgt-GAA-acagagctcac-3' | 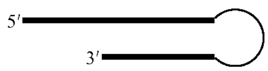 |
| 116 | 5'-TCGTCGTT-GAGCTCT-GAA AGAGCTC-3' | 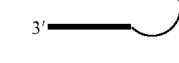 |
| 117 | 5'-TCGTCGTT-GTGAGCTCTGT-GAA-ACAGAGCTCAC-3' | 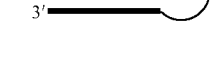 |
| 118 | 5'-TCGTCGTT-GAGCTCT-GAA-AGAGCTC-3' | 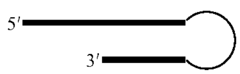 |
| 119 | 5'-TCGTCGTT-GAGCTCT-GAA-AGAGCTC-3' | 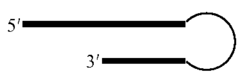 |
| 120 | 5'-TGCTGCTT-GAGCTCT-GAA-AGAGCTC-3' | 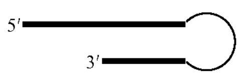 |
| 121 | 5'-TCTTGACGTTCTCTCT-3' | 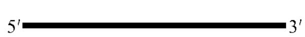 |
| 122 | 5'-TCTTGACGTTCTCTCT-GAA-AGAGAG-3' | 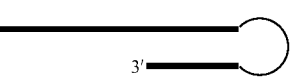 |
| 123 | 5'-TCTTGACGTTCTCTCT-GAA-agagag-3' | 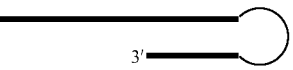 |
| 124 | 5'-tcttgacgttctctct-GAA-AGAGAG-3' | 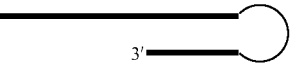 |
| 125 | 5'-tcttgacgttctctct-GAA-agagag-3' | 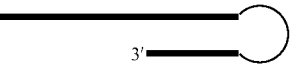 |
| 126 | 5'-tcttgacgttctctct-gaa-agagag-3' | 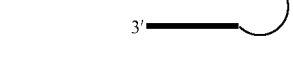 |
| 127 and 46 | 5'-TCTTGACGTTCTCTCT-X-AGAGAG-3' | 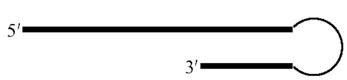 |

TABLE 5-continued

| SEQ ID NO: | Sequence* | Structure |
|---|---|---|
| 128 and 47 | 5'-tcttgacgttctctct-X-agagag-3' | (hairpin loop structure) |

*upper case-PS;
lower case-PO;
Bold-2'-O-methyl-ribonucleotides (in 116 and 117);
G-2'-deoxy-7-deaza-G (in 118);
G-araG (in 119);
X-C3-linker (in 127 and 128).

Alternatively, the nucleic acid molecule of the invention can be two immunomers linked by way of a non-nucleotidic linker. Non-limiting representative examples of these molecules are presented in Table 6.

TABLE 6

| Immunomer No: | Sequence*/ (SEQ ID NO:) | Structure |
|---|---|---|
| 129 | 5'-TCGTCGTT-X-GTCTCGAGAC-5' (129 and 49) | 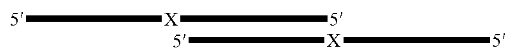 |
| 130 | 5'-TCGTCGTT-XX-GTCTCGAGAC-5' (129 and 49) | 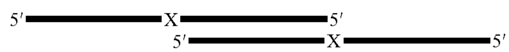 |
| 131 | 5'-TCGTCGTT-XXX-GTCTCGAGAC-5' (129 and 49) | 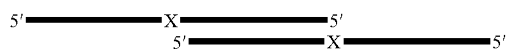 |
| 132 | 5'-TCGTCGTT-Y-GTCTCGAGAC-5' (129 and 49) | 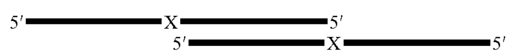 |
| 133 | 5'-TCGTCGTT-Z-GTCTCGAGAC-5' (129 and 49) | 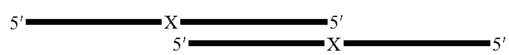 |
| 134 | 5'-TCGTCGTT-XXX-GUCUCGAGAC-5' (129 and 50) | 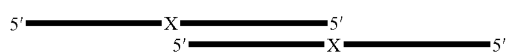 |
| 135 | 5'-TCGTCGTT-XXX-GTCTCGAGAC-5' (56 and 49) | 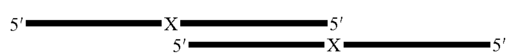 |
| 136 | 5'-TTGTGCTT-XXX-GTCTCGAGAC-5' (52 and 49) | 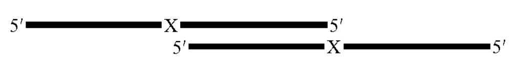 |
| 137 | 5'-TCGTCGTT-XXX-GTCTCCACAC-5' (129 and 49) | 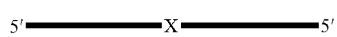 |
| 138 | 5'-TCGTCGTT-XXX-ccgtagctacGG-5' (129 and 49) | 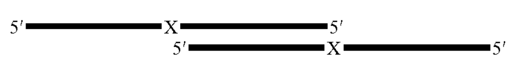 |
| 139 | 5'-TCGTCGTT-XX-ccgtagctacGG-5' (129 and 53) | 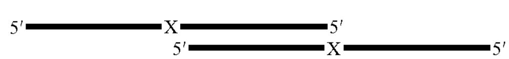 |
| 140 | 5'-TCGTCGTT-X-ccgtagctacGG-5' (129 and 53) | 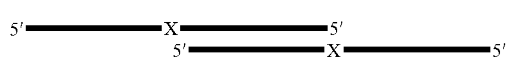 |
| 141 | 5'-TCGTCGTT-3'-3'-ccgtagctacGG-5' (129 and 53) | 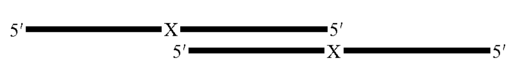 |
| 142 | 5'-TCGTCGTT-Y-ccgtagctacGG-5' (129 and 53) | 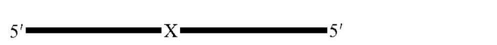 |

TABLE 6-continued

| Immunomer No: | Sequence*/ (SEQ ID NO:) | Structure |
|---|---|---|
| 143 | 5'-TCGTCGTT-Z-ccgtagctacGG-5' (129 and 53) | 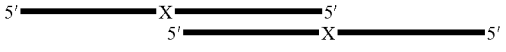 |
| 144 | 5'-TCGTCGTT-XXX-ctcgag-5' (129 and 54) | 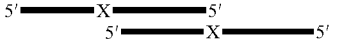 |
| 145 | 5'-TCGTCGTT-XXX-ctgtctcgagacag-5' (129 and 55) | 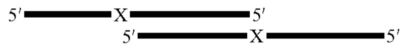 |
| 146 | 5'-TCGTCGTT-XXX-cgactgtctcgagacagtcg-5' (129 and 74) | 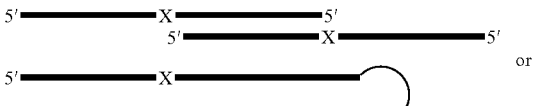 or |
| 147 | 5'-TCGTCGTT-XXX-gucucgagac-5' (129 and 75) | 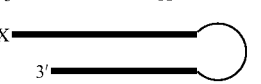 |
| 148 | 5'-TCGTCGTTG-X-tgcatcgatgca-3'-X-3'-GTTGCTGCT-5' (76, 77, and 76) | 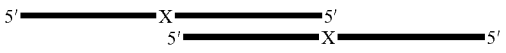 |
| 149 | 5'-TCGTCGTTG-3'-X-3'-tgcatcgatgca-X-GTTGCTGCT-5' (76, 78, and 76) | 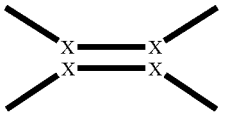 |
| 150 | 5'-TCGTCGTTG-X-TGCATCGATGCA-3'-X-3'-GTTGCTGCT-5' (76, 79, and 76) | 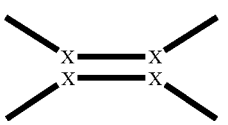 |
| 151 | 5'-TCGTCGTTG-3'-X-3'-TGCATCGATGCA-X-GTTGCTGCT-5' (76, 80, and 76) | 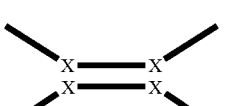 |
| 152 | 5'-tcgtcgttg-X-TGCATCGATGCA-3'-X-3'-gttgctgct-5' (81, 79, and 81) | 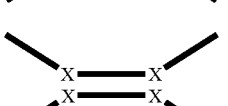 |
| 153 | 5'-tcgtcgttg-3'-X-3'-TGCATCGATGCA-X-gttgctgct-5' (81, 80, and 81) | 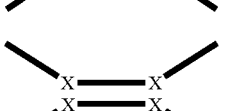 |
| 154 | 5'-tcgtcgtt-XXX-gtctcgagac-5' (82 and 83) | 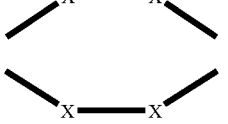 |
| 155 | 5'-TCGTCGTT-XXX-gtctcgagac-5' (129 and 83) | 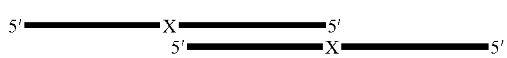 |
| 156 | 5'-TCGTCGTTG-X-tgcatcgatgca-3' (76 and 77) | 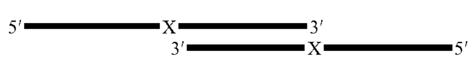 |
| 157 | 5'-TCGTCGTTGtgcatcgatgca-3' (SEQ ID NO: 130) | 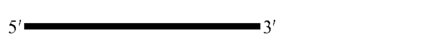 |

TABLE 6-continued

| Immunomer No: | Sequence*/ (SEQ ID NO:) | Structure |
|---|---|---|
| 158 | 5'-tcgtcgttgTGCATCG-ATGCA-3' (SEQ ID NO: 131) | 5'▬▬▬▬▬3' <br> 3'▬▬▬▬▬5' |

*Upper case-PS;
lower case-PO, X-C3-linker;
Y-tetraethyleneglycol linker;
Z-hexaethyleneglycol linker, bold-2'-O-methylribonucleotides (in immunomers 134 and 147);
G-2'-deoxy-7-deaza-G (in immunomer 135).

Alternatively, further, non-limiting, representatives are presented in Table 7.

TABLE 7

| Immunomer No. | |
|---|---|
| 159 | 5'-TCGTCGTT-GAGCUCU-G <br> ‖‖‖‖‖‖ \ <br> ............A <br> 3'-CUCGAGA-A / <br> (SEQ ID NO: 132) |
| 160 | 5'-TCGTCGTT-GAGCUCUCU-G <br> ‖‖‖‖‖‖‖‖ \ <br> ............A <br> 3'-CUCGAGAGA-A / <br> (SEQ ID NO: 133) |
| 161 | 5'-TCGTCGTT-GAGCUCUCUGU-G <br> ‖‖‖‖‖‖‖‖‖‖ \ <br> ............A <br> 3'-CUCGAGAGACA-A / <br> (SEQ ID NO: 134) |
| 162 | 5'-TCRTCRTT-GTGAGCTCTGT-G <br> ‖‖‖‖‖‖‖‖‖‖ \ <br> ............A <br> 3'-CACTCGAGACA-A / <br> (SEQ ID NO: 135) |
| 163 | 5'-TCRTCRTT-X-GTGAGCTCTGT-G <br> ‖‖‖‖‖‖‖‖‖‖ \ <br> ............A <br> 3'-CACTCGAGACA-A / <br> (SEQ ID NOS 136 and 137) |
| 164 | 5'-TCRTCRTT-GTGAGCTCTGT-G <br> ‖‖‖‖‖‖‖‖‖‖ \ <br> ............A <br> 3'-CACUCGAGACA-A / <br> (SEQ ID NO: 138) |
| 165 | 5'-TCRTCRTT-XXX-GTCTCGAGAC-5' <br> (SEQ ID NOS 136 and 139) |
| 166 | 5'-TCRTCRTT-XXX-GUCUCGAGAC-5' <br> (SEQ ID NOS 136 and 140) |
| 167 | 5'-TCG₁TCG₁TT-XXX-*GUCUCGAGAC*-5' <br> (SEQ ID NOS 141 and 142) |
| 168 | 5'-TCG₁TCG₁TT-XXX-GTCTCCACTC-5 <br> (SEQ ID NOS 141 and 143) |
| 169 | 5'-TCG₁TCG₁TT-XXX-GUCUCCACUC-5' <br> (SEQ ID NOS 141 and 144) |
| 170 | 5'-TCRTCRTT-GTGAGCTCTGT-G <br> ‖‖‖‖‖‖‖‖‖‖ \ <br> ............A <br> 3'-CACUCGAGACA-A / <br> (SEQ ID NO: 145) |
| 171 | 5'-TCRTCRTT-X-GUGAGCUCUGU-G <br> ‖‖‖‖‖‖‖‖‖‖ \ <br> ............A <br> 3'-CACUCGAGACA-A / <br> (SEQ ID NOS 136 and 146) |
| 172 | TCGTCGTT-gtgagctctgtg-GAA-acagagcucac <br> (SEQ ID NO: 147) |

Italic phase represents a phosphodiester linkage, other linkages are phosphorothioate unless otherwise indicated
Inderline = 2'-OMe-nucleoside; X = C3 linker
R = 2'-deoxy-7-deazaguanosine
$G_1$ = 2'-deoxy-7-deazaguanoise Another aspect of the invention provides an immunostimulatory nucleic acid wherein the sequence of the immunostimulatory oligonucleotide and/or immunomer is at least partially self-complementary. A self-complementary sequence as used herein refers to a base sequence which, upon suitable alignment, may form intramolecular or, more typically, intermolecular basepairing between G-C, A-T, A-U and/or G-U wobble pairs. In one embodiment the extent of self-complementarity is at least 50 percent. For example an 8-mer that is at least 50 percent self-complementary may have a sequence capable of forming 4, 5, 6, 7, or 8 G-C, A-T, A-U and/or G-U wobble basepairs. Such basepairs may but need not necessarily involve bases located at either end of the self-complementary immunostimulatory oligonucleotide and/or immunomer. Where nucleic acid stabilization may be important to the immunostimulatory oligonucleotide and/or immunomer, it may be advantageous to "clamp" together one or both ends of a double-stranded nucleic acid, either by basepairing or by any other suitable means. The degree of self-complementarity may depend on the alignment between immunostimulatory oligonucleotide and/or immunomer, and such alignment may or may not include single- or multiple-nucleoside overhangs. In other embodiments, the degree of self-complementarity is at least 60 percent, at least 70 percent, at least 80 percent, at least 90 percent, or even 100 percent.

By way of non-limiting example, in certain embodiments of this aspect the immunostimulatory nucleic acid will have a structure as detailed in formula (V)

(V)

As would be recognized by one skilled in the art, the depicted immunomer compounds have secondary structure because the sequences of the domains are complementary allowing for intermolecular hydrogen bonding. Domains A and A' may or may not be identical, domains A and C may or may not be identical, domains A and C' may or may not be identical, domains A' and C may or may not be identical, domains A' and C' may or may not be identical, domains B and B' may or may not be identical and domains C and C' may or may not be identical. Moreover, additional immunomers can bind through intermolecular hydrogen bonding thereby creating a chain, or multimers, of immunomers according to the invention. n can be any number of continuous self complementary immunomer compounds.

As used herein, the term "complementary" means having the ability to hybridize to a nucleic acid. Such hybridization is ordinarily the result of hydrogen bonding between complementary strands, preferably to form Watson-Crick or Hoogsteen base pairs, although other modes of hydrogen bonding, as well as base stacking can also lead to hybridization.

As used herein, the term "secondary structure" refers to intermolecular hydrogen bonding. Intermolecular hydrogen bonding results in the formation of a duplexed nucleic acid molecule.

Non-limiting representative nucleic acid molecules are presented in Table 8.

TABLE 8

| Immunomer | |
|---|---|
| 173 | 5'-TCG$_1$AACG$_1$TTCG$_1$-X-G$_1$CTTG$_1$CAAG$_1$CT-5' (SEQ ID NO: 148) |
| 174 | 5'-TCG$_1$AACG$_1$TTCG-X-GCTTG$_1$CAAG$_1$CT-5' (SEQ ID NO: 149) |
| 175 | 5'-TCTCACCTTCT-X-TCTTCCACTCT-5' (SEQ ID NO: 150) |
| 176 | 5'-TCG$_2$AACG$_2$TTCG$_2$-X-G$_2$CTTG$_2$CAAG$_2$CT-5' (SEQ ID NO: 151) |
| 177 | 5'-TCG$_2$AACG$_2$TTCG-X-GCTTG$_2$CAAG$_2$CT-5' (SEQ ID NO: 152) |
| 178 | 5'-TCG$_1$TCG$_1$AACG$_1$TTCG$_1$AGATGAT-3' (SEQ ID NO: 153) |
| 179 | 5'-TCG$_2$TCG$_2$AACG$_2$TTCG$_2$AGATGAT-3' (SEQ ID NO: 154) |
| 180 | 5'-TCG$_3$TCG$_3$AACG$_3$TTCG$_3$AGATGAT-3' (SEQ ID NO: 155) |
| 181 | 5'-TC$_1$GTC$_1$GAAC$_1$GTTC$_1$GAGATGAT-3' (SEQ ID NO: 156) |
| 182 | 5'-TC$_2$GTC$_2$GAAC$_2$GTTC$_2$GAGATGAT-3' (SEQ ID NO: 157) |
| 183 | 5'-TC$_3$GTC$_3$GAAC$_3$GTTC$_3$GAGATGAT-3' (SEQ ID NO: 158) |

TABLE 8-continued

| Immunomer | |
|---|---|
| 184 | 5'-TCG$_1$AACG$_1$TTC-X-CTTG$_1$CAAG$_1$CT-5' (SEQ ID NO: 159) |
| 185 | 5'-TCG$_1$TTCG$_1$AACG$_1$-X-G$_1$CAAG$_1$CTTG$_1$CT-5' (SEQ ID NO: 160) |
| 186 | 5'-TCCAACCTTCG-X-GCTTCCAACCT-5' (SEQ ID NO: 161) |
| 187 | 5'-TCG$_1$TTG$_1$CAACG$_1$-X-G$_1$CAACG$_1$TTG$_1$CT-5' (SEQ ID NO: 162) |
| 188 | 5'-TCG$_2$AACG$_2$TTCT-X-TCTTG$_2$CAAG$_2$CT-5' (SEQ ID NO: 163) |
| 189 | 5'-TCG$_1$AACG$_2$TTCG$_1$-XG$_1$CTTG$_2$CAAG$_1$CT-5' (SEQ ID NO: 164) |
| 190 | 5'-TCG$_1$AAC$_1$GTTCG$_1$-X-G$_1$CTTGC$_1$AAG$_1$CT-5' (SEQ ID NO: 165) |

Normal phase represents a phosphorothioate linkage
$G_1$=2'-deoxy-7-deazaguanosine
$G_2$=Arabinoguanosine
$G_3$=2'-deoxyinosine
$C_1$=1-(2'-deoxy-β-D-ribofuranosyl)-2-oxo-7-deaza-8-methylpurine
$C_2$=Arabinocytidine
$C_3$=2'-deoxy-5-hydroxycytidine
X=C3 Linker A particularly preferred immunomer compound for use in the methods of the invention has the following structure (SEQ ID NO: 48).

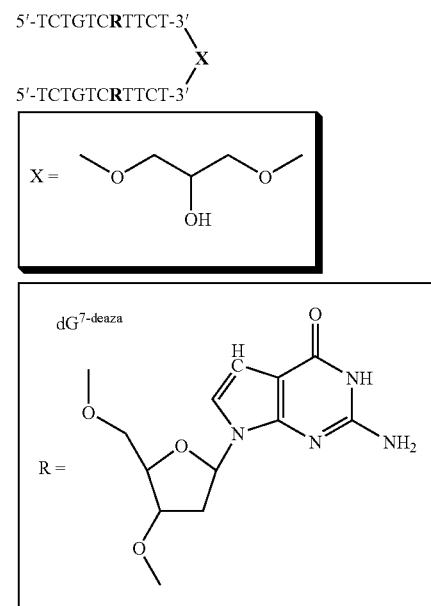

The methods and compositions according to all aspects of the invention are useful in therapeutic approaches to treating diseases wherein the treatment involves immune system modulation and immune-based therapies. Particularly preferred disease targets include cancer, infectious diseases and allergies.

In certain embodiments, the therapeutic method is for the treatment of cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreatic cancer; prostate cancer; rectal cancer; sarcomas; skin cancer; testicular cancer; thyroid cancer; and renal cancer, as well as other carcinomas and sarcomas.

In some embodiments, the therapeutic method is for the treatment of an infection. By way of non-limiting example, viruses that have been found to infect humans include but are not limited to: Retroviridae (e.g. human immunodeficiency viruses, such as HIV-1 (also referred to as HTLV-III, LAV or HTLV-III/LAV, or HIV-III), and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxviridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

In certain embodiments, therapeutic methods of the invention are directed to the treatment of an allergy. An "allergen" refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: Canine (*Canis familiaris*); Dermatophagoides (e.g. *Dermatophagoides farinae*); Felis (*Felis domesticus*); Ambrosia (*Ambrosia artemuisfolia*); Lolium (e.g. *Lolium perenne* or *Lolium multiflorum*); Cryptomeria (*Cryptomeria japonica*); Alternaria (*Alternaria alternata*); Alder; Alnus (*Alnus gultinoasa*); Betula (*Betula verrucosa*); Quercus (*Quercus alba*); Olea (*Olea europa*); Artemisia (*Artemisia vulgaris*); Plantago (e.g. *Plantago lanceolata*); Parietaria (e.g. *Parietaria officinalis* or *Parietaria judaica*); Blattella (e.g. *Blattella germanica*); Apis (e.g. *Apis multiflorum*); Cupressus (e.g. *Cupressus sempervirens, Cupressus arizonica* and *Cupressus macrocarpa*); Juniperus (e.g. *Juniperus sabinoides, Juniperus virginiana, Juniperus communis* and *Juniperus ashei*); Thuya (e.g. *Thuya orientalis*); Chamaecyparis (e.g. *Chamaecyparis obtusa*); Periplaneta (e.g. *Periplaneta americana*); *Agropyron* (e.g. *Agropyron repens*); Secale (e.g. *Secale cereale*); Triticum (e.g. *Triticum aestivum*); Dactylis (e.g. *Dactylis glomerata*); Festuca (e.g. *Festuca elatior*); Poa (e.g. *Poa pratensis* or *Poa compressa*); Avena (e.g. *Avena sativa*); Holcus (e.g. *Holcus lanatus*); Anthoxanthum (e.g. *Anthoxanthum odoratum*); Arrhenatherum (e.g. *Arrhenatherum elatius*); Agrostis (e.g. *Agrostis alba*); Phleum (e.g. *Phleum pratense*); Phalaris (e.g. *Phalaris arundinacea*); Paspalum (e.g. *Paspalum notatum*); Sorghum (e.g. *Sorghum halepensis*); and Bromus (e.g. *Bromus inermis*). Specific allergens may be purchased commercially (e.g., INDOOR Biotechnologies Inc., Charlottesville, Va. 22903).

In a second aspect, the invention provides a method for treating cancer in a cancer patient comprising administering to the patient a chemotherapeutic agent in combination with an immunostimulatory oligonucleotide and/or immunomer conjugate, which comprises an immunostimulatory oligonucleotide and/or immunomer compound, as described above, and an antigen conjugated to the immunostimulatory oligonucleotide and/or immunomer compound at a position other than the accessible 5' end. In some embodiments, the non-nucleotidic linker comprises an antigen associated with cancer, which is conjugated to the oligonucleotide. In some other embodiments, the antigen is conjugated to the oligonucleotide at a position other than its 3' end. In some embodiments, the antigen produces a vaccine effect. For purposes of the invention, the term "associated with" means that the antigen is present when the cancer, is present, but either is not present, or is present in reduced amounts, when the cancer is absent.

The immunostimulatory oligonucleotides and/or immunomer compound is covalently linked to the antigen, or it is otherwise operatively associated with the antigen. As used herein, the term "operatively associated with" refers to any association that maintains the activity of both immunostimulatory oligonucleotide and/or immunomer compound and antigen. Nonlimiting examples of such operative associations include being part of the same liposome or other such delivery vehicle or reagent. Additionally, a nucleic acid molecule encoding the antigen can be cloned into an expression vector and administered in combination with the immunostimulatory oligonucleotide and/or immunomer compound. As used herein, the term "vector" refers to a nucleic acid molecule capable of transporting another nucleic acid to which it has been linked. Preferred vectors are those capable of autonomous replication and expression of nucleic acids to which they are linked (e.g., an episome). Vectors capable of directing the expression of genes to which they are operatively linked are referred to herein as "expression vectors." In general, expression vectors of utility in recombinant DNA techniques are often in the form of "plasmids" which refer generally to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

In embodiments wherein the immunostimulatory oligonucleotide and/or immunomer compound is covalently linked to the antigen, such covalent linkage preferably is at any position on the immunostimulatory oligonucleotide and/ or immunomer compound other than an accessible 5' end of an immunostimulatory oligonucleotide. For example, the antigen may be attached at an internucleoside linkage or may be attached to the non-nucleotidic linker. Alternatively, the antigen may itself be the non-nucleotidic linker.

In a third aspect, the invention provides pharmaceutical formulations comprising an immunostimulatory oligonucleotide and/or immunostimulatory oligonucleotide conjugate and/or immunomer compound or immunomer conjugate according to the invention, a chemotherapeutic agent and a physiologically acceptable carrier. As used herein, the term "physiologically acceptable" refers to a material that does not interfere with the effectiveness of the immunomer compound and is compatible with a biological system such as a cell, cell culture, tissue, or organism. Preferably, the biological system is a living organism, such as a vertebrate. Preferred chemotherapeutic agents include, without limitation Gemcitabine methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP470, Hycamtin/Topotecan, PKC412, Valspodar/PSC833, Novantrone/ Mitroxantrone, Metaret/Suramin, Batimastat, E7070, BCH-4556, CS-682, 9-AC, AG3340, AG3433, Incel/VX-710, VX-853, ZD0101, IS1641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Placlitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/ 776C85/5FU enhancer, Campto/Levamisole, Camptosar/ Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/ Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, Iodine seeds, CDK4 and CDK2 inhibitors, PARP inhibitors, D4809/ Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'deoxycoformycin), Semustine (methyl-CCNU), Teniposide (VM-26) and Vindesine sulfate.

In yet another embodiment, the formulations include a cancer vaccine selected from the group consisting of EFG, Anti-idiotypic cancer vaccines, Gp75 antigen, GMK melanoma vaccine, MGV ganglioside conjugate vaccine, Her2/ new, Ovarex, M-Vax, O-Vax, L-Vax, STn-KHL theratope, BLP25 (MUC-1), liposomal idiotypic vaccine, Melacine, peptide antigen vaccines, toxin/antigen vaccines, MVAvased vaccine, PACIS, BCG vaccine, TA-HPV, TA-CIN, DISC-virus and ImmunCyst/TheraCys.

In a further aspect, the invention provides a method for treating cancer in a cancer patient comprising administering to the patient a monoclonal antibody in combination with an immunostimulatory oligonucleotide and/or immunomer compound, as described herein. Passive immunotherapy in the form of antibodies, and particularly monoclonal antibodies, has been the subject of considerable research and development as anti-cancer agents. The term "monoclonal antibody" as used herein refers to an antibody molecule of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. Examples of anti-cancer agents include, but are not limited to, Panorex (Glaxo-Welcome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech) and Herceptin (Genentech/Hoffman la Roche). Antibodies may also be employed in active immunotherapy utilising anti-idiotype antibodies which appear to mimic (in an immunological sense) cancer antigens. Monoclonal antibodies can be generated by methods known to those skilled in the art of recombinant DNA technology.

As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington's Pharmaceutical Sciences,* 18th Edition, ed. A. Gennaro, Mack Publishing Co., Easton, Pa., 1990.

Toll-like receptors (TLRs) function as sensors of infection and induce the activation of innate and adaptive immune responses. TLRs recognize a wide variety of ligands, called pathogen-associated molecular patterns (PAMPs). Upon recognizing conserved pathogen-associated molecular products, TLRs activate host defense responses through their intracellular signalling domain, the Toll/interleukin-1 receptor (TIR) domain, and the downstream adaptor protein MyD88. Dendritic cells and macrophages normally respond to Toll-like receptor (TLR) ligands and cytokines (for example, interleukin-1β; IL-6 and tumour necrosis factor, TNF), which they also produce; natural killer (NK) cells and T cells are also involved. After TLR stimulation by bacterial compounds, innate immune cells release a range of cytokines. Some examples of TLR ligands include, but are not limited to, lipoproteins; peptidoglycan, zymosan (TLR2), doublestranded RNA, polyI:polyc (TLR3), lipopolysaccharide, heat shock proteins, taxol (TLR4), flagellin (TLR5), and imidazoquinolines-R848, resiquimod, imiquimod; ssRNA (TLR7/8).

In a fourth aspect, the invention provides a method for sensitizing cancer cells to ionizing radiation. The method according to this aspect of the invention comprises administering to a mammal an immunostimulatory oligonucleotide or an immunomer compound according to the invention and treating the animal with ionizing radiation. In certain preferred embodiments, γ-Irradiation is administered at 1.56 Gy/min. In certain preferred embodiments, radiation therapy is administered from about 0.1 to about 10.0 Gy, preferably from about 0.25 to about 8.0 Gy, more preferably from about 0.5 to about 5.0 Gy, or as 3.0 Gy of radiation either twice for one week, four times for one week, or three times on Days 2, 4, and 9. In certain embodiments pre-treatment with an immunostimulatory oligonucleotide or an immunomer compound is from about 2 to about 6 h prior to γ-irradiation.

In a fifth aspect, the invention provides a method for synergistically stimulating an immune response in a patient comprising administering to a patient a therapeutically effective synergistic amount of an immunomer compound in combination with a therapeutically effective synergistic amount of IL-2, and an antigen, wherein administration of said combination synergistically stimulates the production of cytokines in a patient. Preferred cytokines stimulated in accordance with the invention include but are not limited to one or more of, IL-12, interferon-γ, IFN-α and IFN-β.

In certain embodiments, the method is for the treatment of cancer and the antigen is one specific to or associated with a cancer. In some embodiments, the method is for the treatment of an infection and the antigen is an antigen associated with the infection. In certain embodiments, the method is for the treatment of an allergy and the antigen is associated with the allergy. As used herein, the term "associated with" means that the antigen is present when the cancer, allergen or infectious disease is present, but either is not present, or is present in reduced amounts, when the cancer, allergen or infectious disease is absent.

As used herein, the term "antigen" means a substance that is recognized and bound specifically by an antibody or by a T cell antigen receptor. Antigens can include peptides, proteins, glycoproteins, polysaccharides, gangliosides and lipids; portions thereof and combinations thereof. The antigens can be those found in nature or can be synthetic. Haptens are included within the scope of "antigen." A hapten is a low molecular weight compound that is not immunogenic by itself but is rendered immunogenic when conjugated with an immunogenic molecule containing antigenic determinants.

In certain embodiments, antigens useful in methods and compositions of the invention are tumor-associated and/or tumor-specific antigens. Non-limiting examples include: Prostate Specific Antigen (PSA) and Prostatic Acid Phosphatase (PAP), which are markers normally present in the blood in small amounts that can be elevated in the presence of prostate cancer; Cancer Antigen 125 (CA-125), which is at elevated levels in patients with ovarian cancer and is sometimes elevated in the presence of other cancers; CA 15-3 and CA 27-29, which are useful in following the course of breast cancer and its response to treatment; CA 19-9, which is commonly used as a check for the spread of pancreatic cancer and is also elevated in patients with colorectal, stomach and bile duct cancer; Carcinoembryonic Antigen (CEA), which is normally present in small amounts but can be elevated in the blood of patients with a wide variety of cancers; Alpha-Fetoprotein, which is a marker for hepatocellular and germ cell (nonseminoma) carcinoma; and Galactosyl Transferase II, an isozyme of galactosyl transferase, that has been shown to be elevated in a variety of malignancies, predominantly gastrointestinal. As known by one skilled in the art, tumor-associated and tumor-specific antigens are available commercially. Also contemplated by the invention are those antigens that can be made by recombinant nucleic acid technologies and/or synthetic antigens, e.g., peptides produced by methods known in the art.

In certain embodiments of the fifth aspect of the invention, the invention provides a method for treating cancer in a cancer patient comprising administering to the patient a therapeutically effective synergistic amount of IL-2 in combination with an immunomer conjugate, which comprises an immunomer compound, as described above, and an antigen. In certain embodiments, the antigen is conjugated to the immunomer compound at a position other than the accessible 5' end. In some embodiments, the non-nucleotidic linker of the immunomer compound comprises an antigen associated with cancer. In some embodiments, the antigen is conjugated to the immunomer compound at a position other than its 5' end. In some embodiments, the antigen produces a vaccine effect. For purposes of the invention, the term "associated with" means that the antigen is present when the cancer is present, but either is not present, or is present in reduced amounts, when the cancer is absent.

In some embodiments of the fifth aspect of the invention, the immunomer compound is covalently linked to the antigen, or it is otherwise operatively associated with the antigen. As used herein, the term "operatively associated with" refers to any association that maintains the activity of the immunomer compound and antigen. Nonlimiting examples of such operative associations include being part of the same liposome or other such delivery vehicle or reagent. In embodiments wherein the immunomer compound is covalently linked to the antigen, such covalent linkage preferably is at any position on the immunomer compound other than at an accessible 5' end of the immunomer compound. For example, the antigen may be attached at an internucleoside linkage or may be attached to the non-nucleotidic linker. Alternatively, the antigen may itself be the non-nucleotidic linker.

In a sixth aspect of the invention, at least one immunostimulatory oligonucleotide that is not an immunomer compound is used in combination with a therapeutically effective amount of IL-2 to selectively and synergistically stimulate the production of cytokines in a patient. Preferred cytokines synergistically stimulated in accordance with the invention are selected from the group consisting of, IL-12 and IFN-γ, IFN-α, IFN-β or combinations thereof. In accordance with the present invention, preferred immunostimulatory oligonucleotides that are not immunomer compounds include those containing at least one immunostimulatory CpG dinucleotide wherein C is not cytosine or deoxycytosine and/or G is not guanosine or 2-deoxyguanosine. Other preferred immunostimulatory oligonucleotides of the invention that are not immunomer compounds are those that include alternative immunostimulatory moieties that are not CpG. Examples of such alternative immunostimulatory moieties include but are not limited to nucleosides comprising non-naturally occurring bases and/or sugar and secondary structures of the oligonucleotide itself such as hairpin structures that stabilize the oligonucleotide, as described in the following U.S. patents and pending U.S. patent applications and are incorporated herein by reference: U.S. Pat. Nos. 6,426,334 and 6,476,000; and U.S. patent application Ser. Nos. 09/770,602, 09/845,623, 09/965,116, 60/440,587, 10/361,111, 60/471,247, 60/477,608.

In certain embodiments of the invention, each of the immunomer compound or immunostimulatory oligonucleotide and IL-2 is admixed with a pharmaceutically acceptable carrier prior to administration to the patient. In certain embodiments, the immunomer compound or immunostimulatory oligonucleotide are mixed together with a pharmaceutically acceptable carrier prior to administration, or combined as part of a pharmaceutical composition as described in the fourth aspect of the invention. As used herein, the term "carrier" encompasses any excipient, diluent, filler, salt, buffer, stabilizer, solubilizer, lipid, or other material well known in the art for use in pharmaceutical formulations. It will be understood that the characteristics of the carrier, excipient, or diluent will depend on the route of administration for a particular application. The preparation of pharmaceutically acceptable formulations containing these materials is described in, e.g., *Remington: The Science and Practice of Pharmacy*, 20th Edition, ed. A. L. Gennaro, Lippincott Williams & Wilkins Publishing Co., Philadelphia, Pa., 19106 (ISBN: 0683306472).

In a seventh aspect, the invention provides therapeutic compositions comprising a pharmaceutically acceptable carrier, a therapeutically effective synergistic amount of an immunomer compound or immunostimulotory oligonucleotide, a therapeutically effective synergistic amount of IL-2 and optionally, an antigen, wherein administration of said therapeutic composition synergistically stimulates the production of cytokines in a patient. Preferred cytokines that are synergistically stimulated in accordance with the invention are selected from the group consisting of IL-12 and interferon-γ, IFN-α, IFN-β or combinations thereof.

All aspects of the invention are useful in the treatment of disease, and are particularly useful in immune-based therapies for treating cancer, infectious diseases and allergies. As used herein the term "treating" or "treatment" of disease includes: prevention of disease; dimunition or eradication of signs or symptoms of disease after onset; and prevention of relapse of disease.

In the methods according to the invention, administration of an immunomer compound or immmunostimulatory oligonucleotide in combination with IL-2 can be by any suitable route including, without limitation, parenteral, oral, sublingual, transdermal, topical, intranasal, aerosol, intraocular, intratracheal, intrarectal, vaginal, by gene gun, dermal patch or in eye drop or mouthwash form. Administration of immunomer compounds, immunostimulatory oligonucleotides, IL-2 or therapeutic compositions thereof can be carried out using known procedures using therapeutically effective synergistic amounts and for periods of time effective to treat disease.

The term "in combination with" means in the course of treating the same disease in the same patient, and includes administering the immunomer compound and/or immunostimulatory oligonucleotide and/or IL-2 in any order, including simultaneous administration, as well as temporally spaced order of up to several days apart. Such combination treatment may also include more than a single administration of the immunomer compound and/or immunostimulatory oligonucleotide, and/or IL-2, independently. The administration of the immunomer compound and IL-2 may be by the same or different routes.

One of skill in the art will appreciate that such synergistic effect of either the immunomer compound or immunostimulatory oligonucleotide, IL-2 or both may vary considerably depending on the tissue, organ, the particular disease or the patient to be treated in accordance with the invention. Furthermore, one of skill in the art will appreciate that the therapeutically effective synergistic amount of either the immunomer compound or immunostimulatory oligonucleotide or IL-2 may be lowered or increased by fine tuning and altering the amount of the other component.

When administered systemically, the immunomer compound is preferably administered at a sufficient dosage to attain a blood level of immunomer compound from about 0.0001 micromolar to about 10 micromolar. For localized administration, much lower concentrations than this may be effective, and much higher concentrations may be tolerated. Preferably, a total dosage of immunostimulatory oligonucleotide and/or immunomer compound ranges from about 0.0001 mg per patient-per day to about 200 mg per kg body weight per day. It may be desirable to administer simultaneously, or sequentially, a therapeutically effective synergistic amount of each of the immunomer compound or IL-2 to an individual as a single treatment episode. Preferably, IL-2 is administered in an amount of about 750 to about 75,000 units.

The invention provides a kit comprising a cytokine and.or chemotherapeutic agent, and immunostimulatory oligonucleotides and/or immunomer compounds, the latter comprising at least two oligonucleotides linked together, such that the immunomer compound has more than one accessible 5' end, wherein at least one of the oligonucleotides is an immunostimulatory oligonucleotide. In another aspect, the kit comprises an immunostimulatory oligonucleotide and/or immunostimulatory oligonucleotide conjugate and/or immunomer compound or immunomer conjugate according to the invention, a cytokine and/or chemotherapeutic agent and a physiologically acceptable carrier. The kit will generally also include a set of instructions for use.

The examples below are intended to further illustrate certain preferred embodiments of the invention, and are not intended to limit the scope of the invention.

EXAMPLES

Example 1

Synthesis of Oligonucleotides Containing Immunomodulatory Moieties

Oligonucleotides were synthesized on a 1 μmol scale using an automated DNA synthesizer (Expedite 8909; PerSeptive Biosystems, Framingham, Mass.), following the linear synthesis or parallel synthesis procedures outlined in FIGS. 5 and 6.

Deoxyribonucleoside phosphoramidites were obtained from Applied Biosystems (Foster City, Calif.). 1',2'-dideoxyribose phosphoramidite, propyl-1-phosphoramidite, 2-deoxyuridine phosphoramidite, 1,3-bis-[5-(4,4'-dimethoxytrityl)pentylamidyl]-2-propanol phosphoramidite and methyl phosponamidite were obtained from Glen Research (Sterling, Va.). β-L-2'-deoxyribonucleoside phosphoramidite, α-2'-deoxyribonucleoside phosphoramidite, mono-DMT-glycerol phosphoramidite and di-DMT-glycerol phosphoramidite were obtained from ChemGenes (Ashland, Mass.). (4-Aminobutyl)-1,3-propanediol phosphoramidite was obtained from Clontech (Palo Alto, Calif.). Arabinocytidine phosphoramidite, arabinoguanosine, arabinothymidine and arabinouridine were obtained from Reliable Pharmaceutical (St. Louis, Mo.). Arabinoguanosine phosphoramidite, arabinothymidine phosphoramidite and arabinouridine phosphoramidite were synthesized at Hybridon, Inc. (Cambridge, Mass.) (Noronha et al. (2000) *Biochem.*, 39:7050-7062).

All nucleoside phosphoramidites were characterized by $^{31}P$ and $^{1}H$ NMR spectra. Modified nucleosides were incorporated at specific sites using normal coupling cycles. After synthesis, oligonucleotides were deprotected using concentrated ammonium hydroxide and purified by reverse phase HPLC, followed by dialysis. Purified oligonucleotides as sodium salt form were lyophilized prior to use. Purity was tested by CGE and MALDI-TOF MS.

Example 2

Analysis of Spleen Cell Proliferation

Figure 8A:
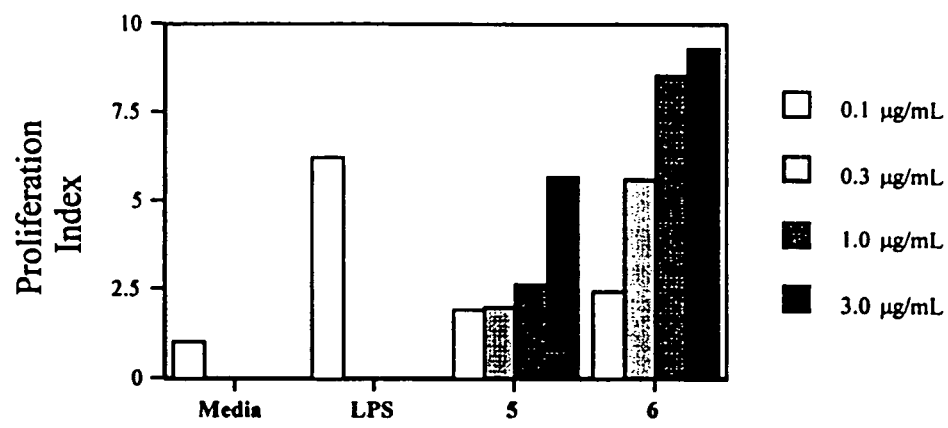
FIG. 8A is a graphic representation of the induction of BALB/c mouse spleen cell proliferation in cell cultures by different concentrations of Immunomers 5 and 6, which have inaccessible and accessible 5'-ends, respectively.

In vitro analysis of splenocyte proliferation was carried out using standard procedures as described previously (see, e.g., Zhao et al., Biochem Pharma 51:173-182 (1996)). The results are shown in FIG. 8A. These results demonstrate that at the higher concentrations, Immunomer 6, having two accessible 5' ends results in greater splenocyte proliferation than does Immunomer 5, having no accessible 5' end or Oligonucleotide 4, with a single accessible 5' end. Immunomer 6 also causes greater splenocyte proliferation than the LPS positive control.

Example 3

In vivo Splenomegaly Assays

Figure 8B:
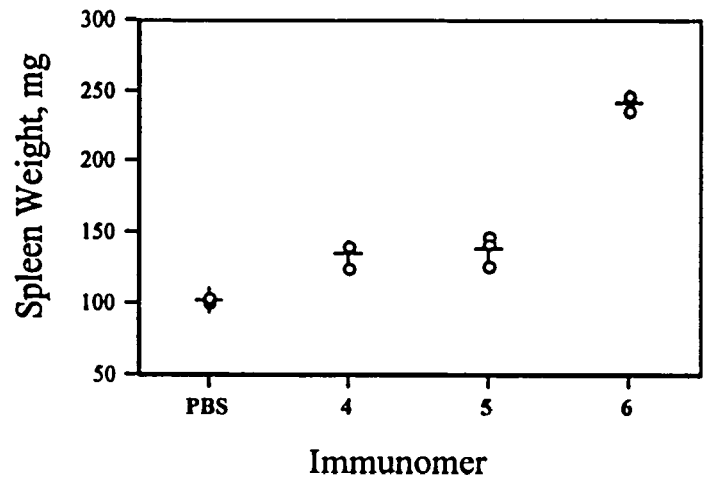
FIG. 8B is a graphic representation of BALB/c mouse spleen enlargement by Oligo 4 and Immunomers 5-6, which have an immunogenic chemical modification in the 5'-flanking sequence of the CpG motif. Again, the immunomer compound, which has accessible 5'-ends (6), has a greater ability to increase spleen enlargement compared with Immunomer 5, which does not have accessible 5'-end and with monomeric Oligo 4.
Figure 9A:
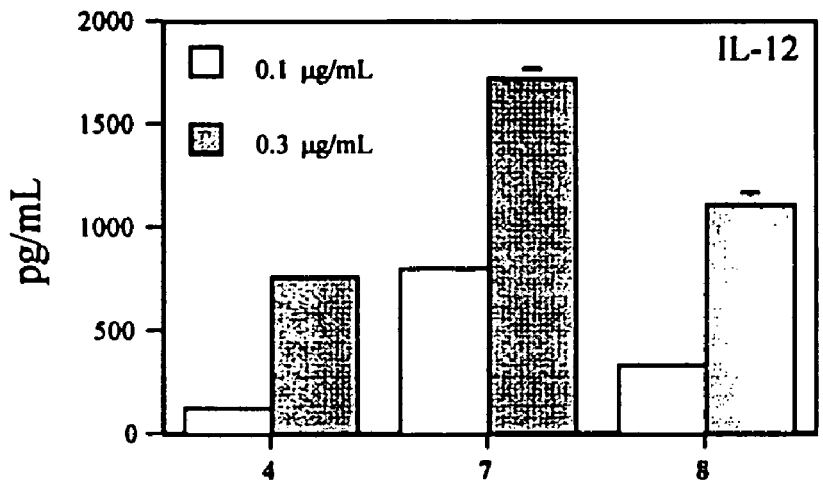
FIG. 9A is a graphic representation of induction of IL-12 by different concentrations of Oligo 4 and Immunomers 7 and 8 in BALB/c mouse spleen cell cultures.
Figure 9B:
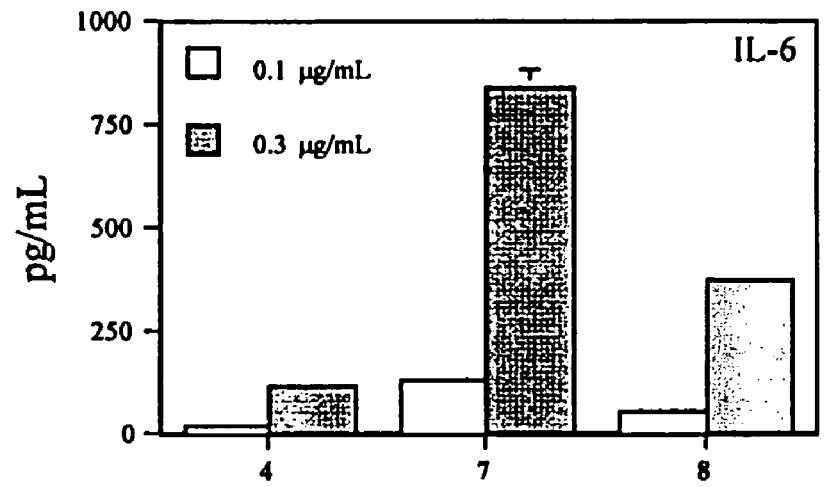
FIG. 9B is a graphic representation of induction of IL-6 by different concentrations of Oligo 4 and Immunomers 7 and 8 in BALB/c mouse spleen cell cultures.
Figure 9C:
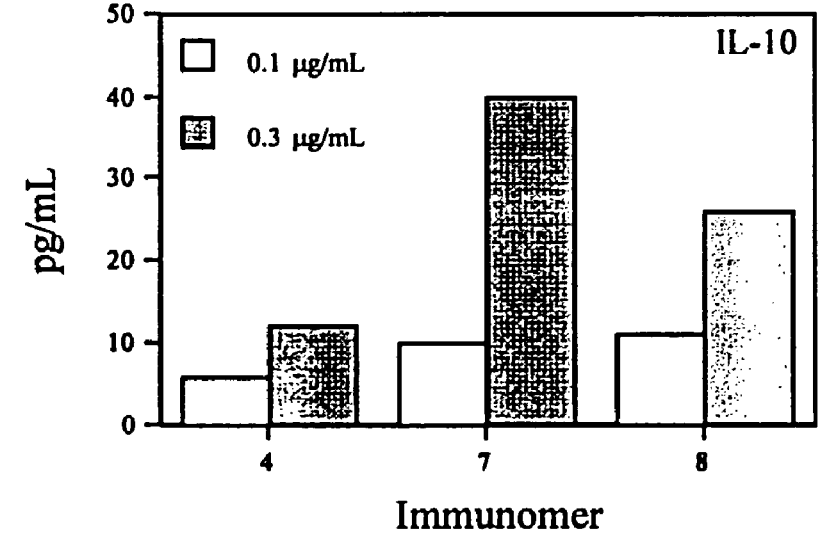
FIG. 9C is a graphic representation of induction of IL-10 by different concentrations of Oligo 4 and Immunomers 7 and 8 in BALB/c mouse spleen cell cultures.
Figure 10A:
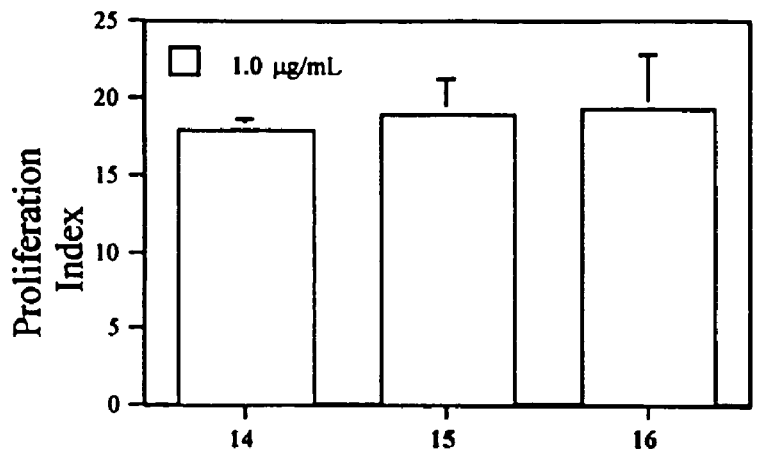
FIG. 10A is a graphic representation of the induction of cell proliferation by Immunomers 14, 15, and 16 in BALB/c mouse spleen cell cultures.
Figure 10B:
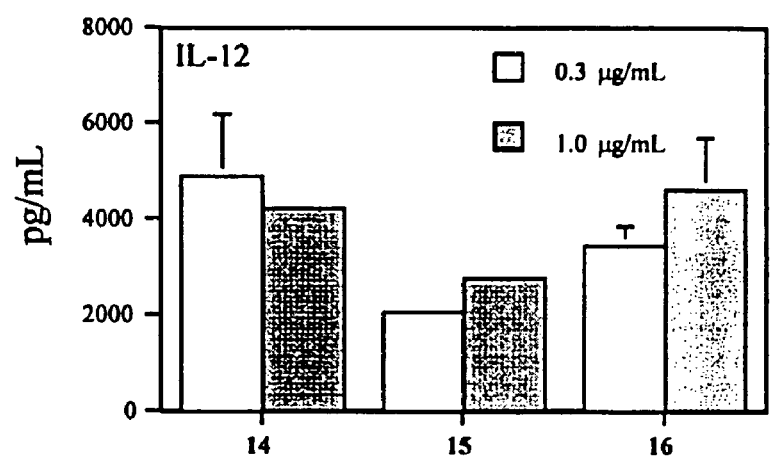
FIG. 10B is a graphic representation of the induction of cell proliferation by IL-12 by different concentrations of Immunomers 14 and 16 in BALB/c mouse spleen cell cultures.
Figure 10C:
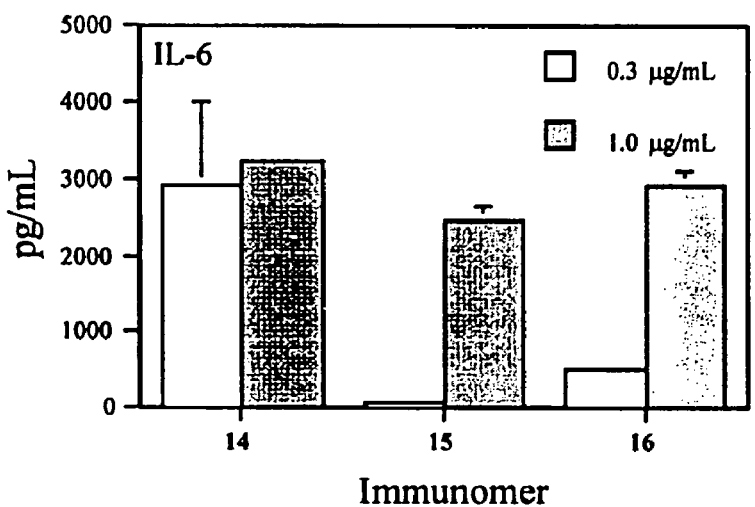
FIG. 10C is a graphic representation of the induction of cell proliferation by IL-6 by different concentrations of Immunomers 14 and 16 in BALB/c mouse spleen cell cultures.
Figure 11A:
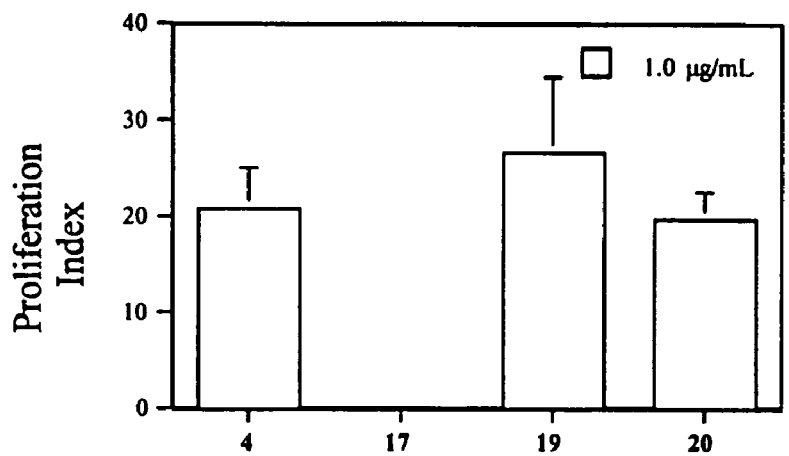
FIG. 11A is a graphic representation of the induction of cell proliferation by Oligo 4 and 17 and Immunomers 19 and 20 in BALB/c mouse spleen cell cultures.
Figure 11B:
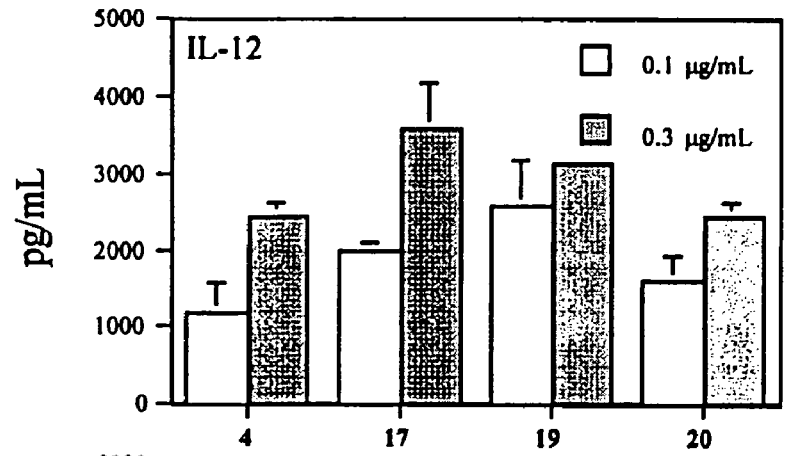
FIG. 11B is a graphic representation of the induction of cell proliferation IL-12 by different concentrations of Oligo 4 and 17 and Immunomers 19 and 20 in BALB/c mouse spleen cell cultures.
Figure 11C:
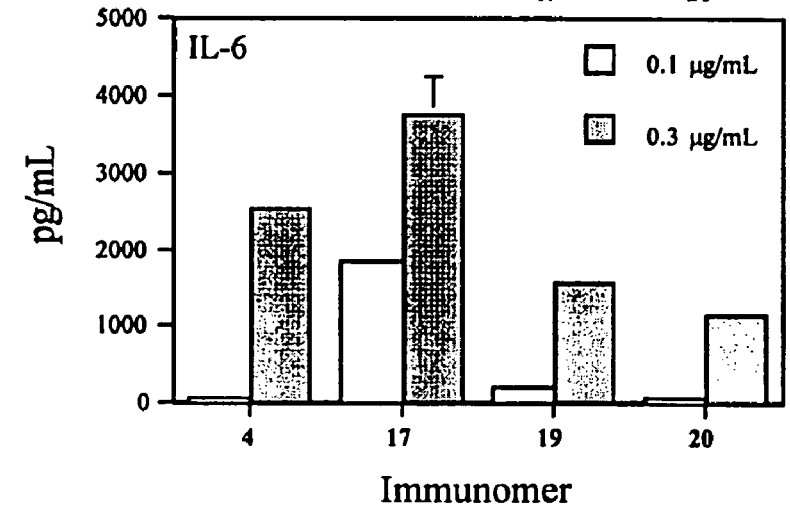
FIG. 11C is a graphic representation of the induction of cell proliferation IL-6 by different concentrations of Oligo 4 and 17 and Immunomers 19 and 20 in BALB/c mouse spleen cell cultures.
Figure 12:
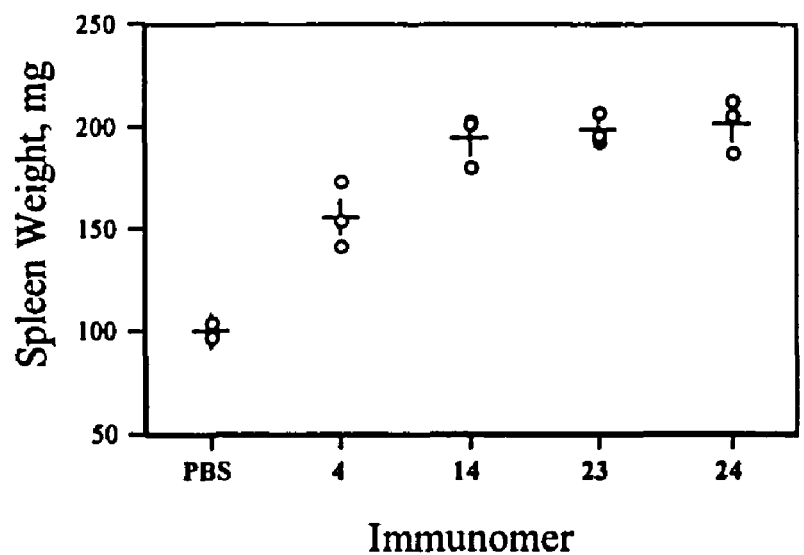
FIG. 12 is a graphic representation of BALB/c mouse spleen enlargement using Oligo 4 and Immunomers 14, 23, and 24.

To test the applicability of the in vitro results to an in vivo model, selected oligonucleotides were administered to mice and the degree of splenomegaly was measured as an indicator of the level of immunostimulatory activity. A single dose of 5 mg/kg was administered to BALB/c mice (female, 4-6 weeks old, Harlan Sprague Dawley Inc, Baltic, CT) intraperitoneally. The mice were sacrificed 72 hours after oligonucleotide administration, and spleens were harvested and weighed. The results are shown in FIG. 8B. These results demonstrate that Immunomer 6, having two accessible 5' ends, has a far greater immunostimulatory effect than do Oligonucleotide 4 or Immunomer 5.

Example 4

Cytokine Analysis

The secretion of IL-12 and IL-6 in vertebrate cells, preferably BALB/c mouse spleen cells or human PBMC, was measured by sandwich ELISA. The required reagents including cytokine antibodies and cytokine standards were purchased form PharMingen, San Diego, Calif. ELISA plates (Costar) were incubated with appropriate antibodies at 5 µg/mL in PBSN buffer (PBS/0.05% sodium azide, pH 9.6) overnight at 4° C. and then blocked with PBS/1% BSA at 37° C. for 30 minutes. Cell culture supernatants and cytokine standards were appropriately diluted with PBS/10% FBS, added to the plates in triplicate, and incubated at 25° C. for 2 hours. Plates were overlaid with 1 µg/mL appropriate biotinylated antibody and incubated at 25° C. for 1.5 hours. The plates were then washed extensively with PBS-T Buffer (PBS/0.05% Tween 20) and further incubated at 25° C. for 1.5 hours after adding streptavidin conjugated peroxidase (Sigma, St. Louis, Mo.). The plates were developed with Sure Blue™ (Kirkegaard and Perry) chromogenic reagent and the reaction was terminated by adding Stop Solution (Kirkegaard and Perry). The color change was measured on a Ceres 900 HDI Spectrophotometer (Bio-Tek Instruments). The results are shown in Table 5A below.

Human peripheral blood mononuclear cells (PBMCs) were isolated from peripheral blood of healthy volunteers by Ficoll-Paque density gradient centrifugation (Histopaque-1077, Sigma, St. Louis, Mo.). Briefly, heparinized blood was layered onto the Histopaque-1077 (equal volume) in a conical centrifuge and centrifuged at 400×g for 30 minutes at room temperature. The buffy coat, containing the mononuclear cells, was removed carefully and washed twice with isotonic phosphate buffered saline (PBS) by centrifugation at 250×g for 10 minutes. The resulting cell pellet was then resuspended in RPMI 1640 medium containing L-glutamine (MediaTech, Inc., Herndon, Va.) and supplemented with 10% heat inactivated FCS and penicillin-streptomycin (100U/ml). Cells were cultured in 24 well plates for different time periods at $1\times10^6$ cells/ml/well in the presence or absence of oligonucleotides. At the end of the incubation period, supernatants were harvested and stored frozen at −70° C. until assayed for various cytokines including IL-6 (BD Pharmingen, San Diego, Calif.), IL-10 (BD Pharmingen), IL-12 (BioSource International, Camarillo, Calif.), IFN-α (BioSource International) and -γ (BD Pharmingen) and TNF-α (BD Pharmingen) by sandwich ELISA. The results are shown in Tables 9 and 9A below.

In all instances, the levels of IL-12 and IL-6 in the cell culture supernatants were calculated from the standard curve constructed under the same experimental conditions for IL-12 and IL-6, respectively. The levels of IL-10, IFN-gamma and TNF-α in the cell culture supernatants were calculated from the standard curve constructed under the same experimental conditions for IL-10, IFN-gamma and TNF-α, respectively.

TABLE 9

Immunomer Structure and Immunostimulatory Activity in Human PBMC Cultures

| Oligo No. and SEQ ID NO: | Sequences and Modification (5'-3') | Oligo Length/ or Each Chain | IL-12 (pg/mL) D1 | IL-12 (pg/mL) D2 | IL-6 (pg/mL) D1 | IL-6 (pg/mL) D2 | IL-10 (pg/mL) D1 | IL-10 (pg/mL) D2 | IFN-γ (pg/mL) D1 | IFN-γ (pg/mL) D2 | TNF-α (pg/mL) D1 | TNF-α (pg/mL) D2 |
|---|---|---|---|---|---|---|---|---|---|---|---|---|
| 25 | 5'-CTATCTGTCGTTCTCTGT-3' | 18mer (PS) | 184 | 332 | 3077 | 5369 | 37 | 88 | 125 | 84 | 537 | nt |
| 26 | 5'-TCTGTCR$_1$TTCT-3' $\diagdown$X$_1$ 5'-TCTGTCR$_1$TTCT-3' $\diagup$ | 11mer (PS) | 237 | 352 | 3724 | 4892 | 48 | 139 | 251 | 40 | 681 | nt |

D1 and D2 are donors 1 and 2.

TABLE 9A

Immunomer Structure and Immunostimulatory Activity in BALB/c Mouse Spleen Cell Cultures

| Oligo No. and SEQ ID NO. | Sequences and Modification (5'-3') | Oligo Length/ or Each Chain | IL-12 (pg/mL) 3 µg/mL | IL-6 (pg/mL) 10 µg/mL |
|---|---|---|---|---|
| 26 | 5'-TCTGTC$R_1$TTCT-3' \\ $X_1$ / 5'-TCTGTC$R_1$TTCT-3' | 11mer (PS) | 870 | 10670 |
| 27 | 5'-TCTGTC$R_2$TTCT-3' \\ $X_1$ / 5'-TCTGTC$R_2$TTCT-3' | 11mer (PS) | 1441 | 7664 |
| 28 | 5'-TCTGT$Y_2R_2$TTCT-3' \\ $X_1$ / 5'-TCTGT$Y_2R_2$TTCT-3' | 11mer (PS) | 1208 | 1021 |
| 29 | 5'-XXTCTGTC$R_1$TTCT-3' \\ $X_1$ / 5'-XXTCTGTC$R_1$TTCT-3' | 11mer (PS) | 162 | 1013 |
| 30 | 5'-*CTGTC$R_2$TTCTCTGT*-3' \\ $X_1$ / 5'-*CTGTC$R_2$TTCTCTGT*-3' | 14mer (PO) | 264 | 251 |
| 31 | 5'-*CTGT$Y_2R_2$TTCTCTGT*-3' \\ $X_1$ / 5'-*CTGT$Y_2R_2$TTCTCTGT*-3' | 14mer (PO) | 149 | 119 |
| 32 | 5'-TCTGAC$R_1$TTCT-3' \\ $X_1$ / 5'-TCTGAC$R_1$TTCT-3' | 11mer (PS) | 2520 | 9699 |
| 33 | 5'-XXTCTGAC$R_1$TTCT-3' \\ $X_1$ / 5'-XXTCTGAC$R_1$TTCT-3' | 11mer (PS) | 2214 | 16881 |
| 34 | 5'-TCTGAC$R_2$TTCT-3' \\ $X_1$ / 5'-TCTGAC$R_2$TTCT-3' | 11mer (PS) | 3945 | 10766 |
| 35 | 5'-TCTGA$Y_2R_2$TTCT-3' \\ $X_1$ / 5'-TCTGA$Y_2R_2$TTCT-3' | 11mer (PS) | 2573 | 19411 |
| 36 | 5'-*CTGA$Y_2$GTTCTCTGT*-3' \\ $X_1$ / 5'-*CTGA$Y_2$GTTCTCTGT*-3' | 14mer (PO) | 2699 | 408 |
| 37 | 5'-*CTGAC$R_2$TTCTCTGT*-3' \\ $X_1$ / 5'-*CTGAC$R_2$TTCTCTGT*-3' | 14mer (PO) | 839 | 85 |

TABLE 9A-continued

Immunomer Structure and Immunostimulatory Activity in BALB/c Mouse Spleen Cell Cultures

| Oligo No. and SEQ ID NO. | Sequences and Modification (5'-3') | Oligo Length/ or Each Chain | IL-12 (pg/mL) 3 μg/mL | IL-6 (pg/mL) 10 μg/mL |
|---|---|---|---|---|
| 38 | 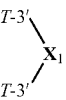 | 14mer (PO) | 143 | 160 |

Italic phase represents a phosphodiester linkage.

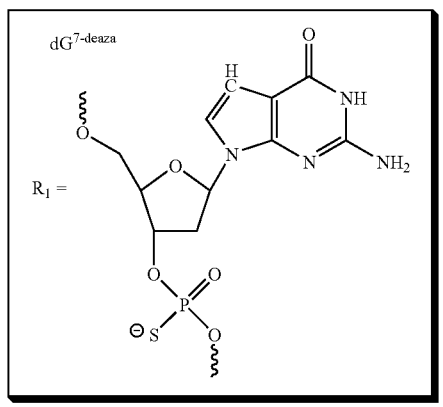

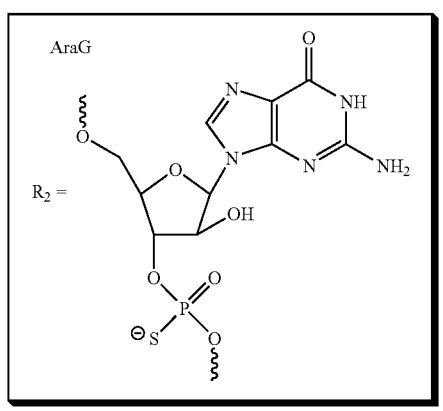

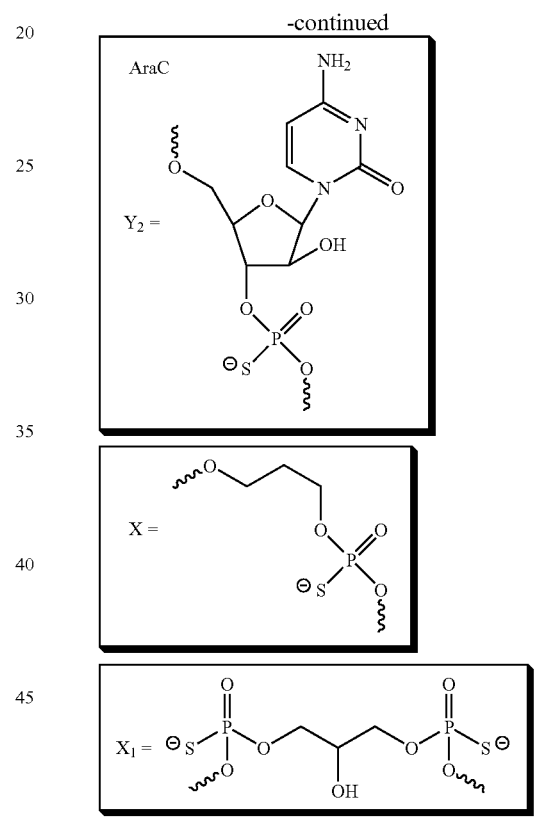

Figure 7A:
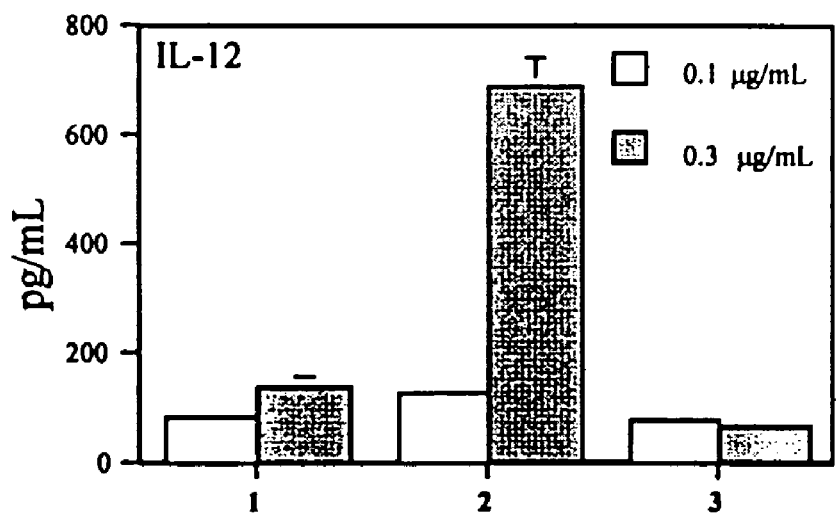
FIG. 7A is a graphic representation of the induction of IL-12 by Oligonucleotide (Oligo) 1 and Immunomers 2-3 in BALB/c mouse spleen cell cultures. These data suggest that Immunomer 2, which has accessible 5'-ends, is a stronger inducer of IL-12 than monomeric Oligo 1, and that Immunomer 3, which does not have accessible 5'-ends, has equal or weaker ability to produce immune stimulation compared with Oligo 1.
Figure 7B:
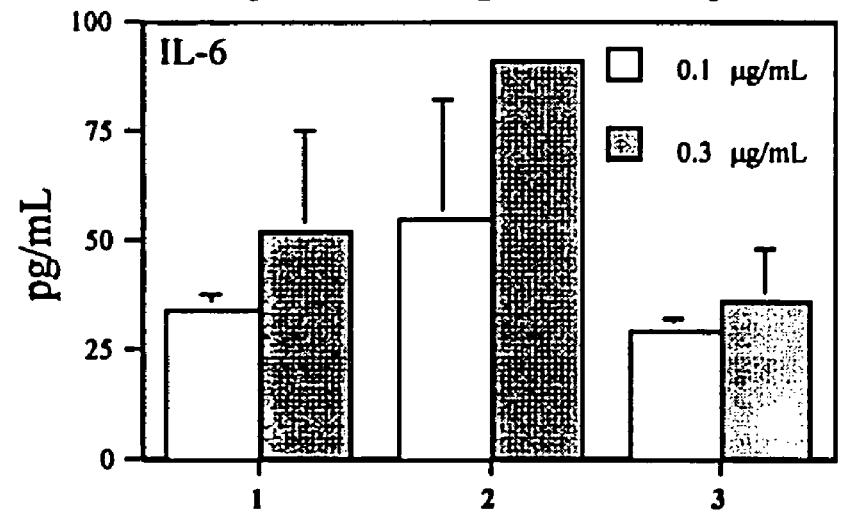
FIG. 7B is a graphic representation of the induction of IL-6 (top to bottom, respectively) by Oligo 1 and Immunomers 2-3 in BALB/c mouse spleen cells cultures. These data suggest that Immunomer 2, which has accessible 5'-ends, is a stronger inducer of IL-6 than monomeric Oligo 1, and that Immunomer 3, which does not have accessible 5'-ends, has equal or weaker ability to induce immune stimulation compared with Oligo 1.
Figure 7C:
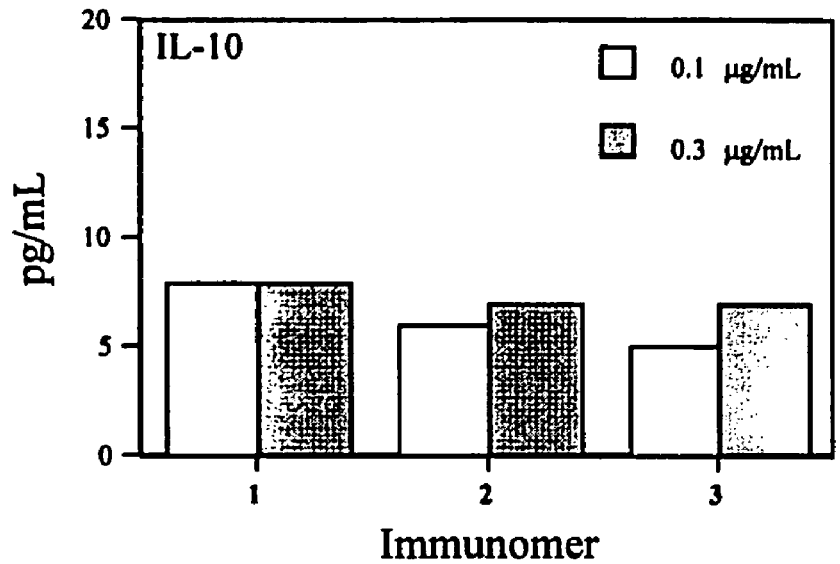
FIG. 7C is a graphic representation of the induction of IL-10 by Oligo 1 and Immunomers 2-3 (top to bottom, respectively) in BALB/c mouse spleen cell cultures.

In addition, the results shown in FIGS. 7A-C demonstrate that Immunomer 2, with two accessible 5' ends elevates IL-12 and IL-6, but not IL-10 at lower concentrations than Oligonucleotide 1 or Immunomer 3, with one or zero accessible 5' ends, respectively.

Example 5

Immunostimulatory Activity of Immunomer Compounds Containing A Non-Natural Pyrimidine or Non-Natural Purine Nucleoside As shown in Tables 10-12, immunostimulatory activity was maintained for immunomer compounds of various lengths having a non-natural pyrimidine nucleoside or non-natural purine nucleoside in the immunostimulatory dinucleotide motif.

TABLE 10

Immunomer Structure and Immunostimulatory Activity

| Immunomer No. and SEQ ID NO: | Sequences and Modification (5'-3') | Oligo Length/ or Each Chain | IL-12 (pg/mL) @3 µg/mL | IL-6 (pg/mL) @3 µg/mL |
|---|---|---|---|---|
| 51 | 5'-CTCACTTTCGTTCTCTGT-3' | 18mer | 404 | 348 |
| 57 | 5'-TCTTTYGTTCT-3'<br>⎤<br>⎥—3'-T-5'<br>⎦<br>5'-TCTTTYGTTCT-3' | 11mer | 591 | 365 |
| 58 | 5'-TCTTTCGTTCT-3'<br>⎤<br>⎥—3'-T-5'<br>⎦<br>5'-TCTTTCGTTCT-3' | 11mer | 303 | 283 |
| 59 | 5'-TTYGTTCT-3'<br>⎤<br>⎥—3'-T-5'<br>⎦<br>5'-TTYGTTCT-3' | 8mer | 55 | 66 |
| 60 | 5'-TTCRTTCT-3'<br>⎤<br>⎥—3'-T-5'<br>⎦<br>5'-TTCRTTCT-3' | 8mer | 242 | 143 |

Y = 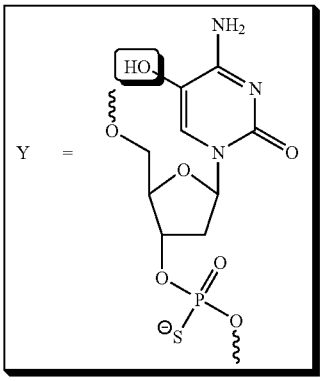

R = 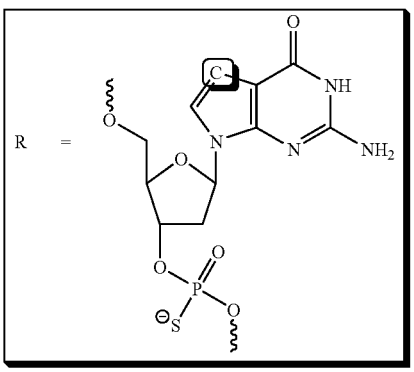

TABLE 10

Immunomer Structure and Immunostimulatory Activity

| Immunomer No. and SEQ ID NO: | Sequences and Modification (5'-3') | Oligo Length/ or Each Chain | IL-12 (pg/mL) @3 µg/mL | IL-6 (pg/mL) @3 µg/mL |
|---|---|---|---|---|
| 25 | 5'-CTATCTGTCGTTCTCTGT-3' | 18mer | 379 | 339 |
| 61 | 5'-TCTGTYGTTCT-3'⏋<br>             ├─3'-T-5'<br>5'-TCTGTYGTTCT-3'⏌ | 11mer | 1127 | 470 |
| 62 | 5'-TCTGTCRTTCT-3'⏋<br>             ├─3'-T-5'<br>5'-TCTGTCRTTCT-3'⏌ | 11mer | 787 | 296 |
| 63 | 5'-GTYGTTCT-3'⏋<br>          ├─3'-T-5'<br>5'-GTYGTTCT-3'⏌ | 8mer | 64 | 126 |
| 64 | 5'-GTCRTTCT-3'⏋<br>          ├─3'-T-5'<br>5'-GTCRTTCT-3'⏌ | 8mer | 246 | 113 |

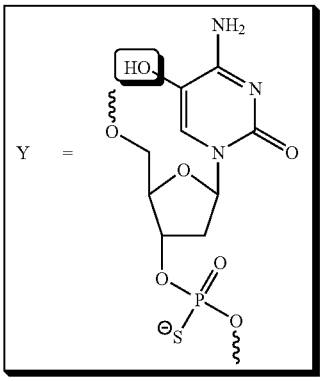

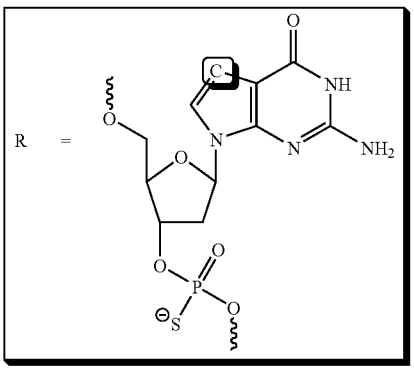

TABLE 12

Immunomer Structure and Immunostimulatory Activity

| Immunomer No. and SEQ ID NO: | Sequences and Modification (5'-3') | Oligo Length/ or Each Chain | IL-12 (pg/mL) 3 μg/mL | IL-6 (pg/mL) 3 μg/mL |
|---|---|---|---|---|
| 4 | 5'-CTATCTGACGTTCTCTGT-3' | 18mer | 1176 | 1892 |
| 65 | 5'-CTATCTGAYGTTCTCTGT-3'⏋<br>  ⎦—3'-T-5'<br>5'-CTATCTGAYGTTCTCTGT-3'⏌ | 18mer | 443 | 192 |
| 66 | 5'-CTATCTGACRTTCTCTGT-3'⏋<br>  ⎦—3'-T-5'<br>5'-CTATCTGACRTTCTCTGT-3'⏌ | 18mer | 627 | 464 |
| 67 | 5'-CTGAYGTTCTCTGT-3'⏋<br>  ⎦—3'-T-5'<br>5'-CTGAYGTTCTCTGT-3'⏌ | 14mer | 548 | 152 |
| 68 | 5'-CTGACRTTCTCTGT-3'⏋<br>  ⎦—3'-T-5'<br>5'-CTGACRTTCTCTGT-3'⏌ | 14mer | 1052 | 1020 |
| 69 | 5'-TCTGAYGTTCT-3'⏋<br>  ⎦—3'-T-5'<br>5'-TCTGAYGTTCT-3'⏌ | 11mer | 2050 | 2724 |
| 70 | 5'-TCTGACRTTCT-3'⏋<br>  ⎦—3'-T-5'<br>5'-TCTGACRTTCT-3'⏌ | 11mer | 1780 | 1741 |
| 71 | 5'-GAYGTTCT-3'⏋<br>  ⎦—3'-T-5'<br>5'-GAYGTTCT-3'⏌ | 8mer | 189 | 55 |
| 72 | 5'-GACRTTCT-3'⏋<br>  ⎦—3'-T-5'<br>5'-GACRTTCT-3'⏌ | 8mer | 397 | 212 |

Example 6

Effect of the Linker on Immunostimulatory Activity

In order to examine the effect of the length of the linker connecting the two oligonucleotides, immunomer compounds that contained the same oligonucleotides, but different linkers were synthesized and tested for immunostimulatory activity. The results shown in Table 13 suggest that linker length plays a role in the immunostimulatory activity of immunomer compounds. The-best immunostimulatory effect was achieved with C3- to C6-alkyl linkers or abasic linkers having interspersed phosphate charges.

TABLE 13

Immunomer Structure and Immunostimulatory Activity

| Immunomer No. | Sequences and Modification (5'-3') | Oligo Length/ or Each Chain | IL-12 (pg/mL) 0.3 μg/mL | IL-6 (pg/mL) 1 μg/mL |
|---|---|---|---|---|
| 4 | 5'-CTATCTGACGTTCTCTGT-3'<br>(SEQ ID NO: 4) | 18mer | 257 | 635 |

TABLE 13-continued

Immunomer Structure and Immunostimulatory Activity

| Immunomer No. | Sequences and Modification (5'-3') | Oligo Length/ or Each Chain | IL-12 (pg/mL) 0.3 µg/mL | IL-6 (pg/mL) 1 µg/mL |
|---|---|---|---|---|
| 73 | 5'-CTGACGTTCT-3'\\_$X_1$_/5'-CTGACGTTCT-3' (SEQ ID NO: 73) | 10mer | 697 | 1454 |
| 74 | 5'-CTGACGTTCT-3'\\_$X_2$_/5'-CTGACGTTCT-3' (SEQ ID NO: 73) | 10mer | 1162 | 669 |
| 75 | 5'-CTGACGTTCT-3'\\_$X_3$_/5'-CTGACGTTCT-3' (SEQ ID NO: 73) | 10mer | 1074 | 1375 |
| 76 | 5'-CTGACGTTCT-3'\\_$X_4$_/5'-CTGACGTTCT-3' (SEQ ID NO: 73) | 10mer | 563 | 705 |
| 77 | 5'-CTGACGTTCT-3'\\_$X_5$_/5'-CTGACGTTCT-3' (SEQ ID NO: 73) | 10mer | 264 | 543 |
| 78 | 5'-CTGACGTTCT-3'\\_$X_6$_/5'-CTGACGTTCT-3' (SEQ ID NO: 73) | 10mer | 1750 | 2258 |
| 79 | 5'-CTGACGTTCT-3'\\_$(X_3psX_3)$_/5'-CTGACGTTCT-3' (SEQ ID NO: 73) | 10mer | 2255 | 2034 |
| 80 | 5'-CTGACGTTCT-3'\\_$(X_3psX_3psX_3)$_/5'-CTGACGTTCT-3' (SEQ ID NO: 73) | 10mer | 1493 | 1197 |
| 81 | 5'-CTGACGTTCT-3'\\_$(X_6psX_6)$_/5'-CTGACGTTCT-3' (SEQ ID NO: 73) | 10mer | 3625 | 2642 |
| 82 | 5'-CTGACGTTCT-3'\\_$(X_6psX_6psX_6)$_/5'-CTGACGTTCT-3' (SEQ ID NO: 73) | 10mer | 4248 | 2988 |
| 83 | 5'-CTGACGTTCT-3'\\_$PO_3S$_/5'-CTGACGTTCT-3' (SEQ ID NO: 73) | 10mer | 1241 | 1964 |

TABLE 13-continued

Immunomer Structure and Immunostimulatory Activity

| Immunomer No. | Sequences and Modification (5'-3') | Oligo Length/ or Each Chain | IL-12 (pg/mL) 0.3 µg/mL | IL-6 (pg/mL) 1 µg/mL |
|---|---|---|---|---|

$X_1$ = (glycerol-type linker with positions 1, 2, and OH)

$X_2$ = (linker with positions 1, 2, 3)

$X_3$ = (linker with positions 1, 2, 3, 4)

$X_4$ = —O—$(CH_2)_{12}$—O—

$X_5$ = (linker with repeating O unit, subscript 6)

$X_6$ = (tetrahydrofuran-type linker with positions 1, 2, 3)

Example 7

Effect of Oligonucleotide Backbone on Immunostimulatory Activity

In general, immunostimulatory oligonucleotides that contain natural phosphodiester backbones are less immunostimulatory than are the same length oligonucleotides with a phosphorothioate backbones. This lower degree of immunostimulatory activity could be due in part to the rapid degradation of phosphodiester oligonucleotides under experimental conditions. Degradation of oligonucleotides is primarily the result of 3'-exonucleases, which digest the oligonucleotides from the 3' end. The immunomer compounds of this example do not contain a free 3' end. Thus, immunomer compounds with phosphodiester backbones should have a longer half life under experimental conditions than the corresponding monomeric oligonucleotides, and should therefore exhibit improved immunostimulatory activity. The results presented in Table 14 demonstrate this effect, with Immunomers 84 and 85 exhibiting immunostimulatory activity as determined by cytokine induction in BALB/c mouse spleen cell cultures.

TABLE 14

Immunomer Structure and Immunostimulatory Activity

| Immunomer No. and SEQ ID NO: | Sequences and Modification (5'-3') | Oligo Length/ or Each Chain | IL-12 (pg/mL) 0.3 µg/mL | IL-6 (pg/mL) 1 µg/mL |
|---|---|---|---|---|
| 4 | 5'-CTATCTGACGTTCTCTGT-3' | 18mer | 225 | 1462 |
| 84 | 5'-CTGACGTTCTCTGT-3'<br>      ⎤<br>      ├─3'-T-5' (PO)<br>      ⎦<br>5'-CTGACGTTCTCTGT-3' | 14mer | 1551 | 159 |

TABLE 14-continued

Immunomer Structure and Immunostimulatory Activity

| Immunomer No. and SEQ ID NO: | Sequences and Modification (5'-3') | Oligo Length/ or Each Chain | IL-12 (pg/mL) 0.3 µg/mL | IL-6 (pg/mL) 1 µg/mL |
|---|---|---|---|---|
| 85 | 5'-LLCTGACGTTCTCTGT-3'⎤<br>         ⎥—3'-T-5' (PO)<br>5'-LLCTGACGTTCTCTGT-3'⎦ | 14mer | 466 | 467 |

L = C3-Linker

Example 8

In vivo Anti-Cancer Activity of Immunomer Compounds in Combination with Chemotherapeutic Agents PC3 cells were cultured in 90% Ham's, F12K Medium with 10% Fetal Bovine Serum (FBS), in presence of 100 U/ml Penicillin and 100 µg/ml Streptomycin to establish the Human Prostate cancer model (PC3). Male athymic nude mice, 4-6 weeks old (Frederick Cancer Research and Development Center, Frederick, Md.), were accommodated for 6 days for environmental adjustment-prior to the study. Cultured PC3 cells were harvested from the monolayer cultures, washed twice with Ham's, F12K Medium (10% FBS), resuspended in FBS-free Ham's, F12K Medium: Matrigel basement membrane matrix (Becton Dickinson Labware, Bedford, Mass.) (5:1; V/V), and injected subcutaneously ($5 \times 10^6$ cells, total volume 0.2 ml) into the left inguinal area of each of the mice. The animals were monitored by general clinical observation, body weight, and tumor growth. Tumor growth was monitored by the measurement, with calipers, of two perpendicular diameters of the implant. Tumor mass (weight in grams) was calculated by the formula, $1/2a \times b^2$, where 'a' is the long diameter (cm) and 'b' is the short diameter (cm). When the mean tumor sizes reached ~80 mg, the animals bearing human cancer xenografts were randomly divided into the treatment and control groups (5 animals/group). The control group received sterile physiological saline (0.9% NaCl) only. Immunomers 26 or 194, aseptically dissolved in physiological saline, was administered by subcutaneously injection at dose of 0.5 or 1.0 mg/kg/day, 3 doses/week. Gemcitabine HCl (Eli Lilly and Company, Indianapolis, Ind.) was given twice by intraperitoneal injection at 160 mg/kg on Day 0 and 3. The detailed treatment schedule is shown as follows.

G1: Saline
G2: Gemcitabine (160 mg/kg/day, IP, Day 0 and 3)
G3: 26 (1.0 mg/kg/day, SC, 3 doses/week, for 6 weeks)
G4: 26 (0.5 mg/kg/day, SC, 3 doses/week, for 6 weeks)
G5: 194 (1.0 mg/kg/day, SC, 3 doses/week, for 6 weeks)
G6: 194 (0.5 mg/kg/day, SC, 3 doses/week, for 6 weeks)
G7: 26 (0.5 mg/kg/day, SC, 3 doses/week, for 6 weeks)+ Gemcitabine (160 mg/kg/day, Day 0 and 3)
G8: 194 (0.5 mg/kg/day, SC, 3 doses/week, for 6 weeks)+ Gemcitabine (160 mg/kg/day, Day 0 and 3)

Figure 13:
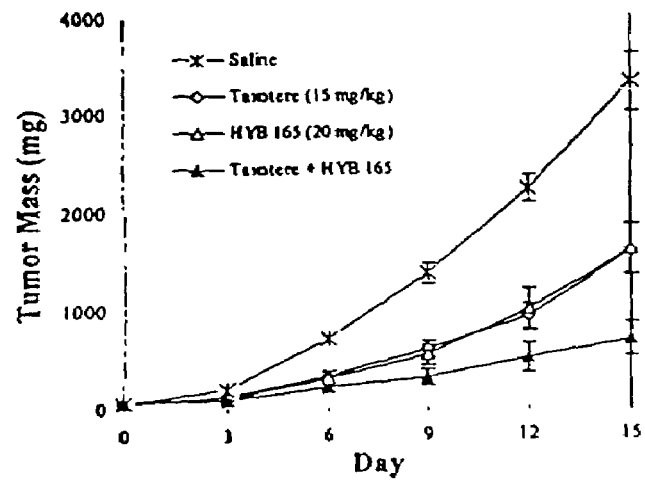
FIG. 13 shows the effect of a method according to the invention on tumor growth in a nude mouse model for prostate cancer.
Figure 13:
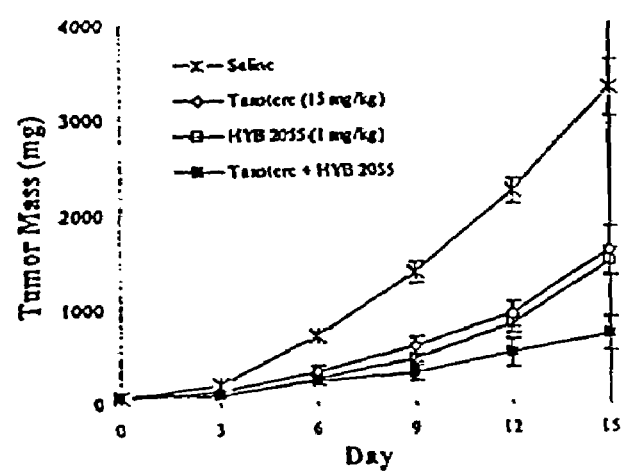
Figure 13:
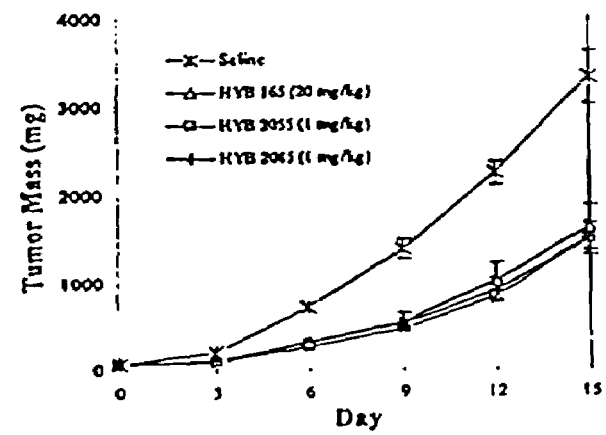

The tumor measurements after various treatments are presented in Table 15 and FIG. 13. The tumor growth in all Immunomer 26 and 194 treated animals was remarkably inhibited compared with saline control (p<0.5). There was a tendency of dose-response relationship in these treatment groups (FIG. 13). There was no significant difference between 26 and 194 (Table 15).

TABLE 15

Tumor mass of tumor-bearing mice following treatment of 26,194, Gemcitabine or combination therapy

| Day | Saline | SD | SE | Gemcitabine 160 mg/kg | SD | SE | 26 1 mg/kg | SD | SE | 26 0.5 mg/kg | SD | SE |
|---|---|---|---|---|---|---|---|---|---|---|---|---|
| 0 | 82.7 | 16.7 | 7.5 | 82.6 | 15.7 | 7.0 | 80.1 | 10.6 | 4.7 | 80.4 | 10.5 | 4.7 |
| 3 | 81.9 | 13.3 | 5.9 | 73.0 | 3.4 | 1.5 | 67.5 | 8.1 | 3.6 | 54.3 | 8.4 | 3.7 |
| 6 | 80.5 | 11.5 | 5.2 | 50.4 | 11.7 | 5.2 | 50.4 | 9.0 | 4.0 | 45.3 | 5.5 | 2.5 |
| 9 | 87.7 | 8.2 | 3.7 | 35.7 | 6.3 | 2.8 | 40.9 | 5.1 | 2.3 | 43.9 | 9.3 | 4.2 |
| 12 | 97.6 | 18.6 | 8.3 | 36.2 | 3.3 | 1.5 | 41.3 | 6.2 | 2.8 | 46.5 | 3.8 | 1.7 |
| 15 | 112.0 | 21.5 | 9.6 | 31.7 | 4.1 | 1.8 | 42.8 | 12.8 | 5.7 | 50.0 | 14.1 | 6.3 |
| 18 | 126.3 | 17.3 | 7.7 | 40.8 | 8.4 | 3.7 | 54.9 | 7.6 | 3.4 | 59.3 | 6.7 | 3.0 |
| 21 | 152.5 | 25.5 | 11.4 | 47.4 | 9.8 | 4.4 | 62.5 | 10.4 | 4.6 | 71.0 | 16.7 | 7.5 |
| 24 | 187.0 | 29.2 | 13.1 | 56.5 | 5.2 | 2.3 | 79.5 | 24.1 | 10.8 | 100.1 | 9.7 | 4.3 |
| 27 | 245.2 | 24.1 | 10.8 | 68.0 | 14.8 | 6.6 | 94.1 | 28.9 | 12.9 | 124.5 | 21.1 | 9.5 |
| 30 | 343.6 | 63.9 | 28.6 | 89.4 | 11.1 | 5.0 | 119.8 | 18.7 | 8.3 | 162.4 | 37.5 | 16.8 |
| 33 | 438.5 | 107.1 | 47.9 | 106.5 | 14.1 | 6.3 | 176.6 | 43.8 | 19.6 | 213.6 | 66.7 | 29.8 |
| 36 | 614.4 | 185.1 | 82.8 | 144.2 | 48.2 | 21.6 | 248.7 | 47.0 | 21.0 | 325.3 | 106.2 | 47.5 |
| 39 | 866.8 | 237.4 | 106.2 | 175.3 | 61.4 | 27.5 | 320.1 | 64.2 | 28.7 | 416.8 | 154.5 | 69.1 |
| 42 | 1136.9 | 205.9 | 92.1 | 269.1 | 78.8 | 35.2 | 417.8 | 78.7 | 35.2 | 546.9 | 139.1 | 62.2 |
| 45 |  |  |  | 383.8 | 146.4 | 65.5 | 550.8 | 134.2 | 60.0 | 667.6 | 284.9 | 127.4 |
| 48 |  |  |  | 538.6 | 260.1 | 116.3 | 736.0 | 197.3 | 88.2 | 852.8 | 399.3 | 178.6 |

TABLE 15-continued

Tumor mass of tumor-bearing mice following treatment of 26,194, Gemcitabine or combination therapy

| Day | 194 1 mg/kg | SD | SE | 194 0.5 mg/kg | SD | SE | 26 + GEM 0.5/160 mg/kg | SD | SE | 194 + GEM 0.5/160 mg/kg | SD | SE |
|---|---|---|---|---|---|---|---|---|---|---|---|---|
| 0 | 80.4 | 11.0 | 4.9 | 79.9 | 10.3 | 4.6 | 79.4 | 10.1 | 4.5 | 78.7 | 12.0 | 5.4 |
| 3 | 52.3 | 9.3 | 4.2 | 64.7 | 9.0 | 4.0 | 45.1 | 8.2 | 3.7 | 44.6 | 8.7 | 3.9 |
| 6 | 38.8 | 4.6 | 2.1 | 46.9 | 14.7 | 6.6 | 31.2 | 5.9 | 2.6 | 34.7 | 4.4 | 2.0 |
| 9 | 34.5 | 9.5 | 4.3 | 43.5 | 13.6 | 6.1 | 22.1 | 4.8 | 2.1 | 23.0 | 3.2 | 1.5 |
| 12 | 35.8 | 9.4 | 4.2 | 43.0 | 15.9 | 7.1 | 15.0 | 3.8 | 1.7 | 11.9 | 2.2 | 1.0 |
| 15 | 36.6 | 8.7 | 3.9 | 48.6 | 15.4 | 6.9 | 18.0 | 3.1 | 1.4 | 12.4 | 3.5 | 1.6 |
| 18 | 45.1 | 14.6 | 6.5 | 62.0 | 20.2 | 9.0 | 17.9 | 3.1 | 1.4 | 15.5 | 1.7 | 0.8 |
| 21 | 53.5 | 12.3 | 5.5 | 73.6 | 20.5 | 9.2 | 18.3 | 2.8 | 1.2 | 14.8 | 2.1 | 1.0 |
| 24 | 72.6 | 22.7 | 10.1 | 93.6 | 23.0 | 10.3 | 23.6 | 4.5 | 2.0 | 23.0 | 1.5 | 0.7 |
| 27 | 86.5 | 13.7 | 6.1 | 119.3 | 17.3 | 7.8 | 27.8 | 4.1 | 1.8 | 25.9 | 3.7 | 1.7 |
| 30 | 114.5 | 22.8 | 10.2 | 157.1 | 49.0 | 21.9 | 33.6 | 5.0 | 2.2 | 36.9 | 6.5 | 2.9 |
| 33 | 161.4 | 44.1 | 19.7 | 218.1 | 81.2 | 36.3 | 43.8 | 10.9 | 4.9 | 47.7 | 16.1 | 7.2 |
| 36 | 198.3 | 43.5 | 19.4 | 313.2 | 104.6 | 46.8 | 50.3 | 13.6 | 6.1 | 46.4 | 16.4 | 7.3 |
| 39 | 249.8 | 77.9 | 34.9 | 420.2 | 199.4 | 89.2 | 67.3 | 29.4 | 13.2 | 59.4 | 28.7 | 12.9 |
| 42 | 366.5 | 110.5 | 49.4 | 527.5 | 219.0 | 98.0 | 77.2 | 28.0 | 12.5 | 82.1 | 29.1 | 13.0 |
| 45 | 490.2 | 122.2 | 54.7 | 620.3 | 258.1 | 115.4 | 104.9 | 57.9 | 25.9 | 110.7 | 46.3 | 20.7 |
| 48 | 683.4 | 144.6 | 64.7 | 759.1 | 223.0 | 99.7 | 128.2 | 77.7 | 34.7 | 133.4 | 62.6 | 28.0 |
| 51 | | | | | | | 177.9 | 109.6 | 49.0 | 177.3 | 68.0 | 30.4 |
| 54 | | | | | | | 233.1 | 143.5 | 64.2 | 224.0 | 79.8 | 35.7 |
| 57 | | | | | | | 297.7 | 190.7 | 85.3 | 289.7 | 121.9 | 54.5 |

Figure 14:
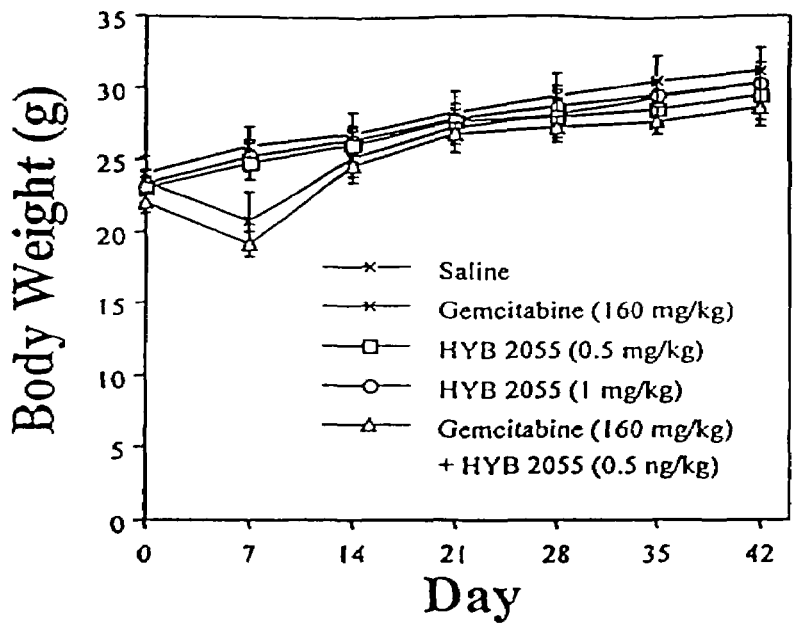
FIG. 14 shows the effect of a method according to the invention on body weight of the mice used in the study.
Figure 14:
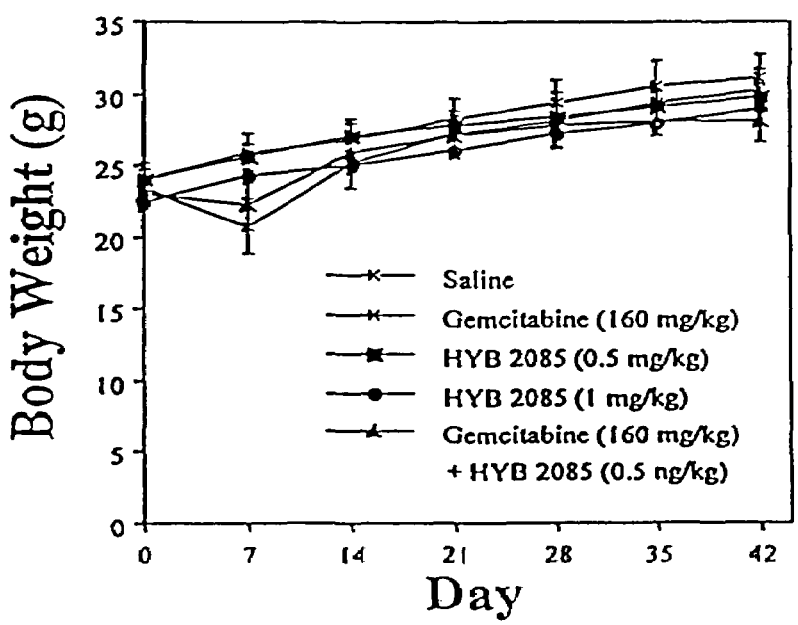
Figure 15A:
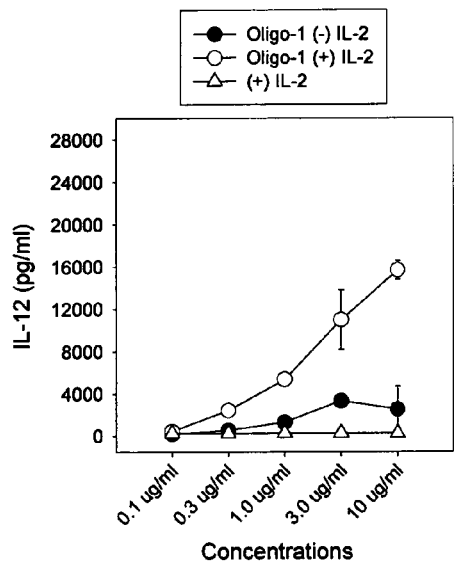
FIG. 15A is a graphic representation demonstrating the synergistic effect on IL-12 production after BALB/c spleenocytes were treated with Oligo 1 and IL-2.
Figure 15B:
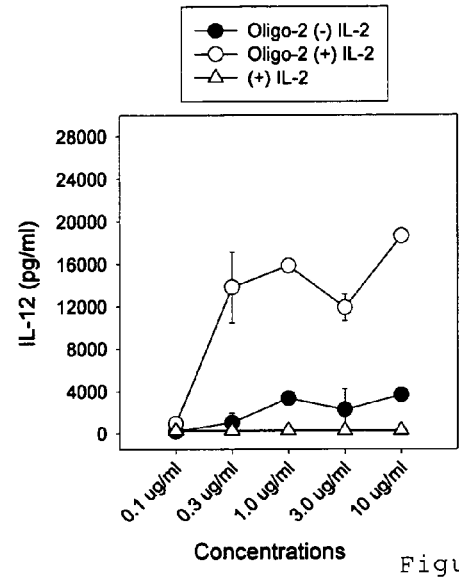
FIG. 15B is a graphic representation demonstrating the synergistic effect on IL-12 production after BALB/c spleenocytes were treated with Oligo 2 and IL-2.
Figure 15C:
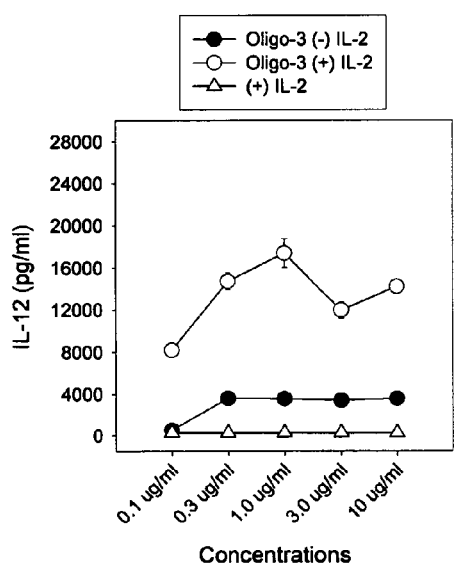
FIG. 15C is a graphic representation demonstrating the synergistic effect on IL-12 production after BALB/c spleenocytes were treated with Oligo 3 and IL-2.
Figure 15D:
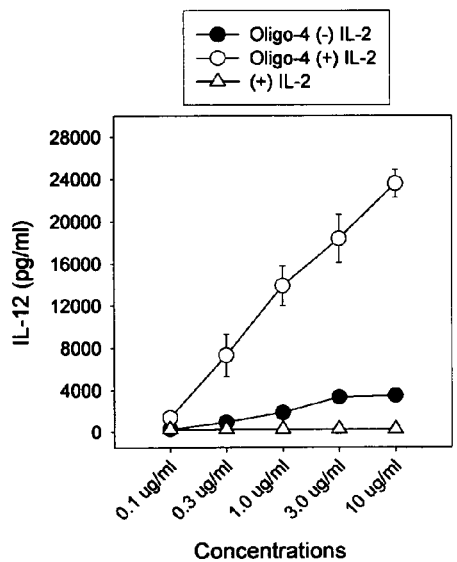
FIG. 15D is a graphic representation demonstrating the synergistic effect on IL-12 production after BALB/c spleenocytes were treated with Oligo 4 and IL-2.
Figure 16A:
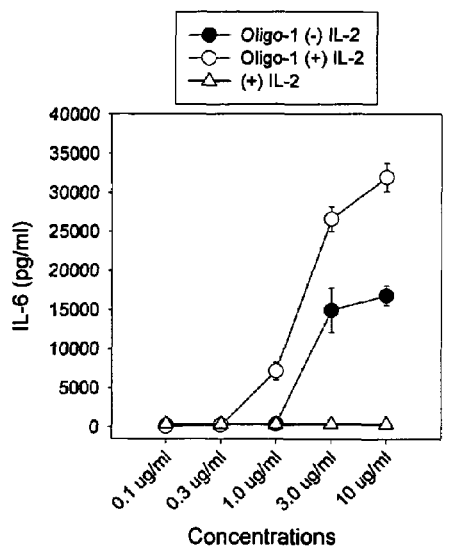
FIG. 16A is a graphic representation demonstrating the effect on IL-6 production after BALB/c spleenocytes were treated with Oligo I and IL-2.
Figure 16B:
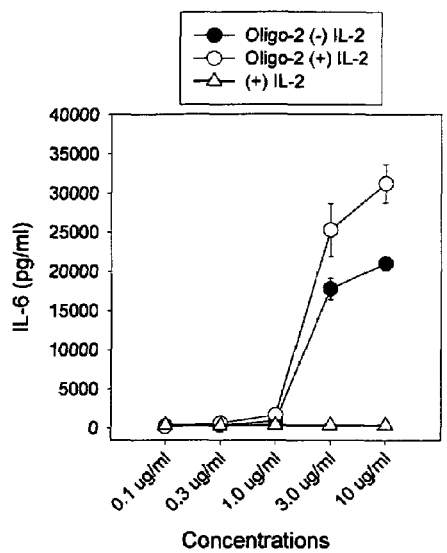
FIG. 16B is a graphic representation demonstrating the effect on IL-6 production after BALB/c spleenocytes were treated with Oligo 2 and IL-2.
Figure 16C:
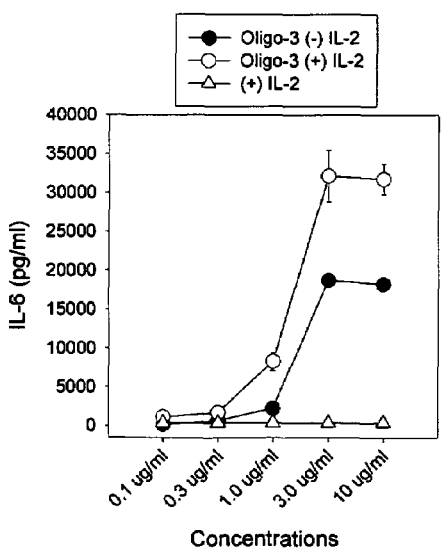
FIG. 16C is a graphic representation demonstrating the effect on IL-6 production after BALB/c spleenocytes were treated with Oligo 3 and IL-2.
Figure 16D:
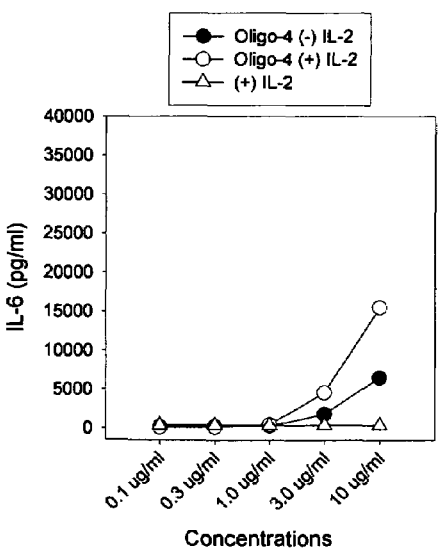
FIG. 16D is a graphic representation demonstrating the effect on IL-6 production after BALB/c spleenocytes were treated with Oligo 4 and IL-2.
Figure 17:
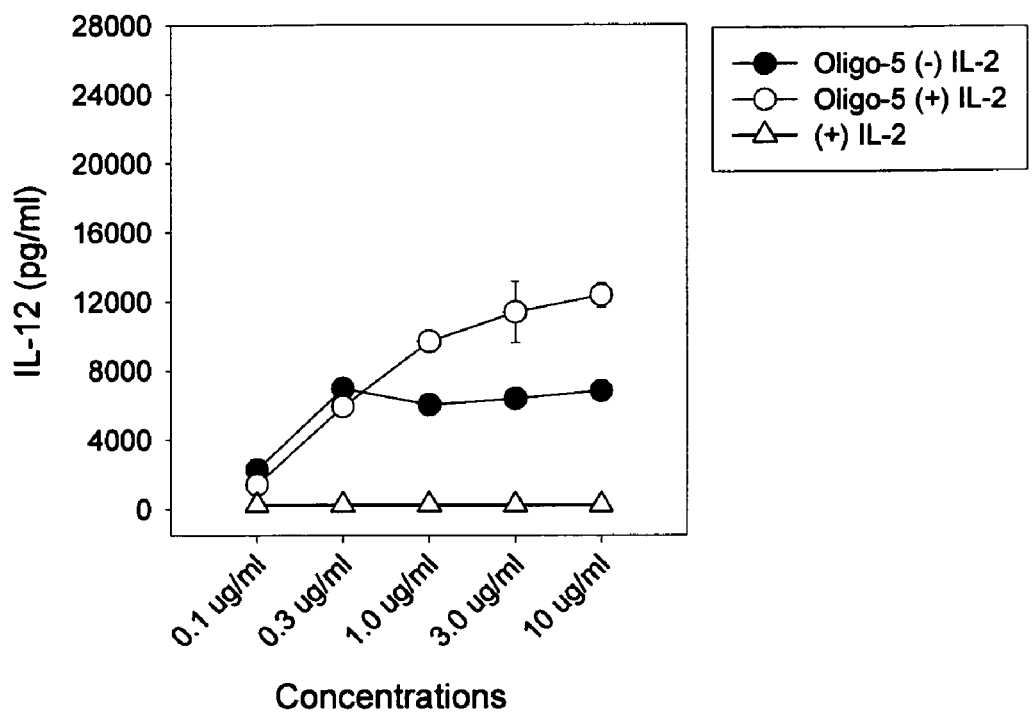
FIG. 17 is a graphic representation demonstrating the synergistic effect on IL-12 production after BALB/c spleenocytes were treated with Oligo 5 and IL-2.
Figure 18A:
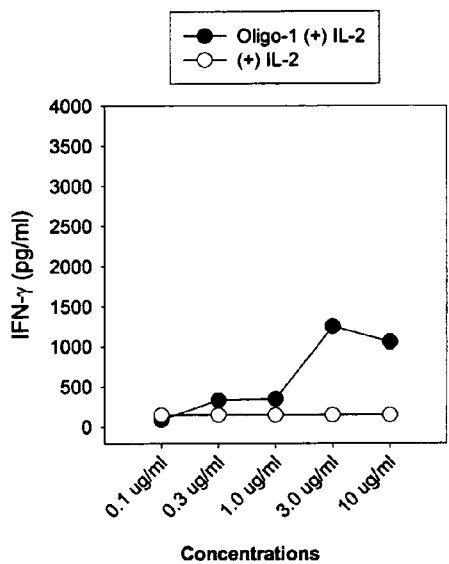
FIG. 18A is a graphic representation demonstrating the effect on IFN-γ production after BALB/c spleenocytes were treated with Oligo 1 and IL-2.
Figure 18B:
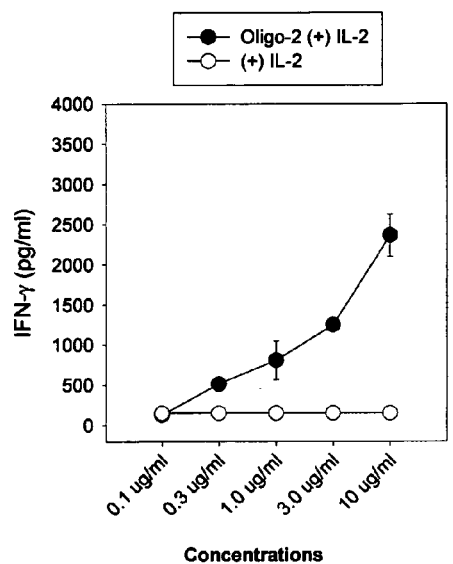
FIG. 18B is a graphic representation demonstrating the effect on IFN-γ production after BALB/c spleenocytes were treated with Oligo 2 and IL-2.
Figure 18C:
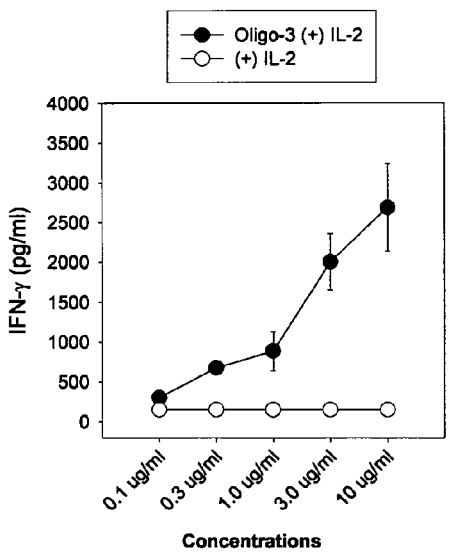
FIG. 18C is a graphic representation demonstrating the effect on IFN-γ production after BALB/c spleenocytes were treated with Oligo 3 and IL-2.
Figure 18D:
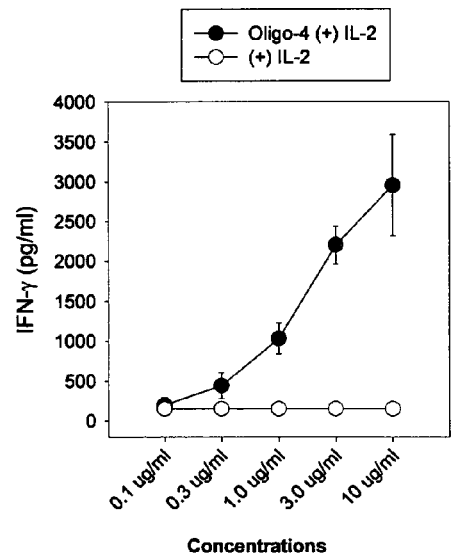
FIG. 18D is a graphic representation demonstrating the effect on IFN-γ production after BALB/c spleenocytes were treated with Oligo 4 and IL-2.
Figure 19:
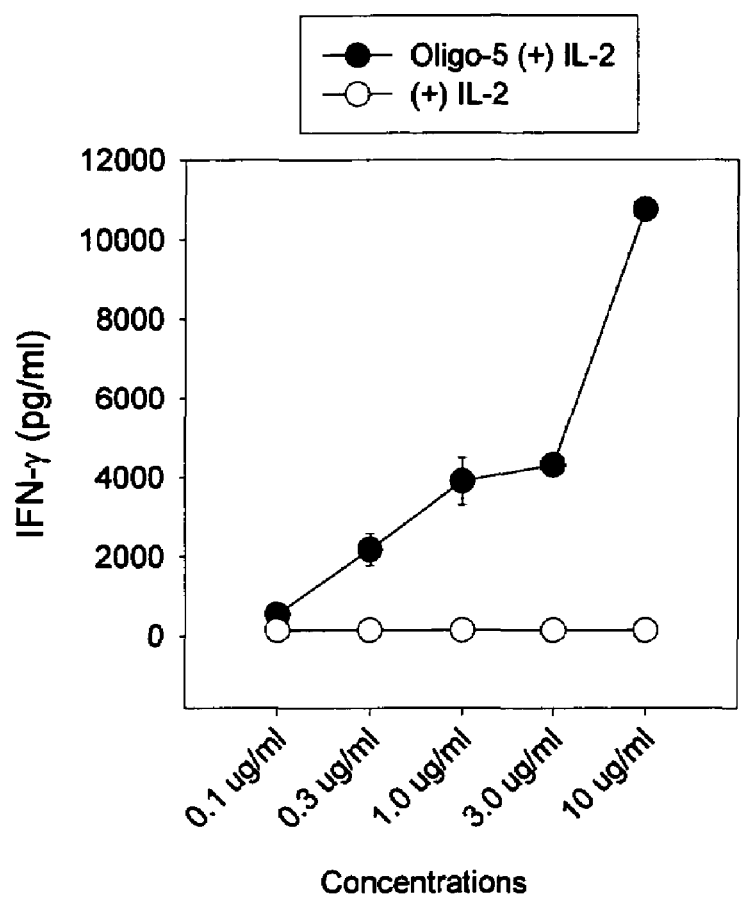
FIG. 19 is a graphic representation demonstrating the effect on IFN-γ production after BALB/c spleenocytes were treated with Oligo 5 and IL-2.

The body weight measurements after treatments at various times are presented in Table 16 and FIG. 14. There was no significant difference in body weight gains among 26 or 194 alone compared with controls. Gemcitabine treated animals had body weight loss in the first week and recovered in a week afterwards. Combination with 26 or 194 did not change the side effect profiles of Gemcitabine. No other clinical abnormality or death was observed in all the groups.

TABLE 16

Body weights of tumor-bearing mice following treatment of 26, 194 or saline.

| Day | Saline | SD | SE | Gemcitabine 160 mg/kg | SD | SE | 26 1 mg/kg | SD | SE | 26 0.5 mg/kg | SD | SE | 194 1 mg/kg |
|---|---|---|---|---|---|---|---|---|---|---|---|---|---|
| 0 | 24.1 | 2.5 | 1.1 | 23.5 | 0.9 | 0.4 | 23.2 | 1.4 | 0.6 | 23.0 | 2.4 | 1.1 | 22.5 |
| 7 | 25.8 | 3.0 | 1.3 | 20.7 | 4.4 | 2.0 | 25.2 | 2.4 | 1.1 | 24.8 | 2.8 | 1.2 | 24.3 |
| 14 | 26.8 | 3.2 | 1.4 | 25.2 | 4.0 | 1.8 | 26.3 | 2.0 | 0.9 | 26.0 | 2.9 | 1.3 | 25.1 |
| 21 | 28.2 | 3.3 | 1.5 | 27.1 | 3.9 | 1.7 | 27.8 | 2.0 | 0.9 | 27.6 | 2.8 | 1.2 | 26.1 |
| 28 | 29.4 | 3.5 | 1.6 | 28.1 | 4.3 | 1.9 | 28.6 | 2.6 | 1.1 | 28.0 | 2.7 | 1.2 | 27.2 |
| 35 | 30.6 | 3.7 | 1.6 | 29.4 | 2.9 | 1.3 | 29.5 | 2.3 | 1.0 | 28.6 | 2.8 | 1.3 | 28.0 |
| 42 | 31.1 | 3.7 | 1.7 | 30.3 | 3.0 | 1.4 | 30.2 | 2.3 | 1.0 | 29.4 | 3.9 | 1.7 | 28.9 |

| Day | SD | SE | 194 0.5 mg/kg | SD | SE | 26 + GEM 0.5/160 mg/kg | SD | SE | 194 + GEM 0.5/160 mg/kg | SD | SE |
|---|---|---|---|---|---|---|---|---|---|---|---|
| 0 | 1.3 | 0.6 | 24.1 | 1.6 | 0.7 | 21.9 | 1.7 | 0.7 | 23.0 | 0.8 | 0.4 |
| 7 | 0.9 | 0.4 | 25.6 | 2.0 | 0.9 | 19.1 | 2.0 | 0.9 | 22.3 | 3.3 | 1.5 |
| 14 | 1.3 | 0.6 | 27.0 | 2.1 | 0.9 | 24.6 | 1.6 | 0.7 | 25.9 | 2.7 | 1.2 |
| 21 | 1.3 | 0.6 | 27.8 | 1.5 | 0.7 | 26.8 | 1.6 | 0.7 | 27.1 | 2.6 | 1.2 |
| 28 | 1.5 | 0.7 | 28.3 | 2.2 | 1.0 | 27.2 | 1.6 | 0.7 | 27.7 | 3.2 | 1.4 |
| 35 | 1.4 | 0.6 | 29.1 | 2.3 | 1.0 | 27.7 | 2.1 | 1.0 | 28.0 | 2.4 | 1.1 |
| 42 | 1.5 | 0.7 | 29.8 | 2.2 | 1.0 | 28.4 | 2.8 | 1.2 | 28.1 | 3.4 | 1.5 |

In summary, 26 and 194 significantly inhibited tumor growth in nude mice bearing human prostate cancer PC3 xenografts with no significant side effects. When 26 or 194 was given in combination with Gemcitabine, each compound significantly increased the therapeutic effect of Gemcitabine without changes in side effect profiles. In addition, there was a tendency in dose dependent response of 26 or 194 treatment.

Example 9

In vivo Anti-Cancer Activity of Immunomer Compounds in Combination with Chemotherapeutic Agents The experiment of Example 8 was repeated using taxotere instead of Gemcitabine. Taxotere was administered on days 0 and 7. 165 was administered 5 days per week. 26 and 194 were administered on days 0, 2, 4, 7, 9 and 11. The results are shown in Table 17 below. These results clearly demonstrate synergy between the immunomer compounds and taxotere.

PBS/1% BSA at 37° C. for 30 min. Cell culture supernatants and cytokine standards were appropriately diluted with PBS/1% BSA, added to the plates in triplicate, and incubated at 25° C. for 2 h. Plates were washed and incubated with the appropriate biotinylated antibody and incubated at 25° C. for 1.5 h. The plates were washed extensively with PBS/0.05% Tween 20 and then further incubated at 25° C. for 1.5 h. after addition of streptavidine-conjugated peroxidase (Sigma). Plates were developed with Sure Blue™ (Kirkegaard and Perry) chromogenic reagent and the reaction was terminated by adding Stop Solution (Kirkegaard and Perry). The color change was measured on a Ceres 900 HDI Spectrophotometer (Bio-Tek Instruments) at 450nm. The levels of IL-12, IL6 and IFN-γ in the cell culture supernatants were calculated from the standard curve constructed under the same experimental conditions for IL-12, IL-6 and IFN-γ respectively.

The oligonucleotides used in this study are presented in Table 18.

TABLE 17

In vivo anti-cancer activity of immunomer compounds in combination with other chemotherapeutic agents

| Day | Saline | SD | SE | Taxotere (15 mg/kg) | SD | SE | 165 (20 mg/kg) | SD | SE | 26 (1 mg/kg) | SD | SE |
|---|---|---|---|---|---|---|---|---|---|---|---|---|
| 0.00 | 56.93 | 7.92 | 3.54 | 56.64 | 7.94 | 3.55 | 57.93 | 5.56 | 2.49 | 56.74 | 7.79 | 3.48 |
| 3.00 | 196.42 | 22.48 | 10.05 | 128.51 | 20.83 | 9.32 | 95.79 | 16.04 | 7.18 | 87.12 | 6.64 | 2.97 |
| 6.00 | 708.85 | 32.64 | 14.60 | 320.63 | 136.80 | 61.18 | 285.71 | 68.70 | 30.72 | 250.36 | 52.58 | 23.51 |
| 9.00 | 1370.95 | 239.99 | 107.33 | 598.69 | 196.60 | 87.92 | 534.93 | 225.19 | 100.71 | 450.46 | 92.25 | 41.26 |
| 12.00 | 2222.96 | 300.65 | 134.45 | 924.91 | 297.89 | 133.22 | 994.10 | 474.89 | 212.38 | 814.21 | 197.16 | 88.17 |
| 15.00 | 3303.04 | 672.86 | 300.91 | 1589.08 | 578.38 | 258.66 | 1601.73 | 576.19 | 257.68 | 1465.87 | 348.37 | 155.80 |

| Day | Taxotere + 165 | SD | SE | Taxotere + 26 (**mg/kg) | SD | SE | 194 (1 mg/kg) | SD | SE |
|---|---|---|---|---|---|---|---|---|---|
| 0.00 | 55.51 | 9.55 | 4.27 | 56.59 | 8.91 | 3.99 | 55.28 | 10.89 | 4.87 |
| 3.00 | 78.47 | 21.79 | 9.74 | 80.14 | 21.59 | 9.65 | 91.01 | 23.60 | 10.55 |
| 6.00 | 211.52 | 88.59 | 39.62 | 216.85 | 89.40 | 39.98 | 303.00 | 61.33 | 27.43 |
| 9.00 | 302.66 | 178.36 | 79.76 | 307.53 | 184.05 | 82.31 | 512.30 | 110.16 | 49.26 |
| 12.00 | 496.20 | 342.69 | 153.25 | 510.18 | 351.16 | 157.04 | 884.12 | 308.22 | 137.84 |
| 15.00 | 686.47 | 385.97 | 172.61 | 703.50 | 394.65 | 176.49 | 1479.21 | 416.64 | 186.33 |

Example 10

Administration of Immunostimulatory Oligonucleotides and IL-2

Splenocytes were isolated from BALB/c mice as described-above and were plated in 24-well dishes at a density of 5×10$^6$ cells/mL. CpG oligonucleotides were dissolved in TE buffer (10 mM Tris-HCl, pH 7.5, 1 mM EDTA) was added to a final concentration of 0.03, 0.1, 0.3, 1.0, 3.0, or 10.0 µg/mL to mouse spleen cell cultures. In order to study the role of IL-2 in CpG oligonucleotide-induced time-dependent cytokine secretion, recombinant human IL-2 (Sigma) was added at a concentration of 10 U/ml at the start of the experiment. The cells were then incubated at 37° C. for 4, 8, 24 and 48 h in the presence of test oligonucleotides and the supernatants were collected for ELISA assays. Untreated cells (only IL-2 addition) were taken as controls.

The secretion of mouse IL-12, IL-6 and IFN-γ was measured by sandwich ELISA. The required regents, including cytokine antibodies and standards were purchases from PharMingen. ELISA plates (Costar) were incubated with appropriate capture antibodies in PBSN (PBS/0.05% sodium azide, pH 9.6) buffer overnight at 4° C. and then blocked with

TABLE 18

| SEQ ID NO: | Sequence | Chemistry |
|---|---|---|
| 86 | 5'-CTATCTGACGTTCTCTGT-3' | PS-oligo |
| 87 | (5'-TCTGACRTTCT)$_2$S | R= 7-deaza-dG, PS-oligo |
| 88 | (5'-TCTGACGTTCT)$_2$S | PS-oligo |
| 89 | (5'-XXCTGACGTTCTCTGT)$_2$S | PO-oligo |
| 90 | (5'-TCTGAYGTTCT)$_2$S | Y=R*, PS-oligo |

The results are shown in FIGS. 15-19. Not shown is an assay indicating that the use of SEQ ID NOs 86-90 alone stimulate IFN-γ production only negligibly. The results demonstrate synergy between SEQ ID NOs 86-90 and IL-2 in generating secretion of IL-6, IL-12 and IFN-γ.

EQUIVALENTS

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An immunostimulatory oligonucleotide having the structure 5'-TCRTCRTTG-X-GTTRCTRCT-5'; wherein X is a glycerol linker and R is 2'-deoxy-7-deazaguanosine.

2. A pharmaceutical formulation comprising the oligonucleotide according to claim 1 and a physiologically acceptable carrier.

3. A method for generating an immune response in a vertebrate, the method comprising administering to the vertebrate an immunostimulatory oligonucleotide having the structure 5'-TCRTCRTTG-X-GTTRCTRCT-5; wherein X is a glycerol linker and R is 2'-deoxy-7-deazaguanosine.

4. The method according to claim 3, wherein the route of administration is selected from parenteral, oral, sublingual, transdermal, topical, intranasal, aerosol, intraocular, intratracheal, intrarectal, vaginal, gene gun, dermal patch, eye drop and mouthwash.

5. The oligonucleotide according to claim 1, further comprising an antibody, antisense oligonucleotide, protein, antigen, allergen, chemotherapeutic agent or adjuvant.

6. The pharmaceutical composition according to claim 2, further comprising an antibody, antisense oligonucleotide, protein, antigen, allergen, chemotherapeutic agent or adjuvant.

7. The method according to claim 3, further comprising administering an antibody, antisense oligonucleotide, protein, antigen, allergen, chemotherapeutic agent or adjuvant.

* * * * *